US012605103B2

(12) United States Patent
Fischer et al.

(10) Patent No.: US 12,605,103 B2
(45) Date of Patent: Apr. 21, 2026

(54) QRS DETECTION AND BRACKETING

(71) Applicant: Medtronic, Inc., Minneapolis, MN (US)

(72) Inventors: Trent Fischer, St. Paul, MN (US); Karen Kleckner, Minneapolis, MN (US); Daniel S. Flo, Minneapolis, MN (US); Marc C. Steckler, Circle Pines, MN (US); Subham Ghosh, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1245 days.

(21) Appl. No.: 17/320,778

(22) Filed: May 14, 2021

(65) Prior Publication Data

US 2021/0361219 A1 Nov. 25, 2021

Related U.S. Application Data

(60) Provisional application No. 63/034,397, filed on Jun. 3, 2020, provisional application No. 63/028,293, filed on May 21, 2020.

(51) Int. Cl.
| | |
|---|---|
| *A61B 5/366* | (2021.01) |
| *G16H 40/67* | (2018.01) |
| (Continued) | |

(52) U.S. Cl.
CPC ............. *A61B 5/366* (2021.01); *G16H 40/67* (2018.01); *A61B 5/282* (2021.01); *A61B 5/725* (2013.01); *A61N 1/36507* (2013.01)

(58) Field of Classification Search
CPC ......... A61B 5/366; A61B 5/282; A61B 5/725; G16H 40/67; A61N 1/36507
See application file for complete search history.

(56) References Cited

U.S. PATENT DOCUMENTS

| | | | |
|---|---|---|---|
| 3,835,864 A | 9/1974 | Rasor et al. | |
| 3,865,118 A | 2/1975 | Bures | |
| | (Continued) | | |

FOREIGN PATENT DOCUMENTS

| | | | |
|---|---|---|---|
| AU | 2008279789 B2 | 10/2011 | |
| AU | 2008329620 B2 | 5/2014 | |
| | (Continued) | | |

OTHER PUBLICATIONS

US 8,886,318 B2, 11/2014, Jacobson et al. (withdrawn)
(Continued)

*Primary Examiner* — Shirley X Jian
(74) *Attorney, Agent, or Firm* — Mueting Raasch Group

(57) ABSTRACT

Electrical activity from tissue of a patient is monitored using a plurality of external electrodes to generate a plurality of electrical signals over time. The plurality of electrical signals are filtered using a first filter having a first frequency range to generate a plurality of first filtered signals. The plurality of electrical signals are filtered using a second filter having a second frequency range different than the first frequency range to generate a plurality of second filtered signals. At least one QRS complex is detected based on the plurality of first filtered signals. A QRS peak of the at least one QRS complex is detected based on the plurality of second filtered signals and the detected at least one QRS complex.

18 Claims, 18 Drawing Sheets

(51) Int. Cl.
  A61B 5/00 (2006.01)
  A61B 5/282 (2021.01)
  A61N 1/365 (2006.01)

(56) References Cited

U.S. PATENT DOCUMENTS

| | | | |
|---|---|---|---|
| 3,943,936 A | 3/1976 | Rasor et al. |
| 3,949,757 A | 4/1976 | Sabel |
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,233,987 A | 11/1980 | Feingold |
| 4,243,045 A | 1/1981 | Mass |
| 4,250,884 A | 2/1981 | Hartlaub et al. |
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,402,323 A | 9/1983 | White |
| 4,428,378 A | 1/1984 | Anderson et al. |
| 4,440,173 A | 4/1984 | Hudziak et al. |
| 4,476,868 A | 10/1984 | Thompson |
| 4,479,500 A | 10/1984 | Smits |
| 4,497,326 A | 2/1985 | Curry |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,566,456 A | 1/1986 | Koning et al. |
| 4,574,814 A | 3/1986 | Buffet |
| 4,593,702 A | 6/1986 | Kepski et al. |
| 4,593,955 A | 6/1986 | Leiber |
| 4,630,204 A | 12/1986 | Mortara |
| 4,630,611 A | 12/1986 | King |
| 4,635,639 A | 1/1987 | Hakala et al. |
| 4,674,508 A | 6/1987 | DeCote |
| 4,674,511 A | 6/1987 | Cartmell |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,763,660 A | 8/1988 | Kroll et al. |
| 4,776,338 A | 10/1988 | Lekholm et al. |
| 4,777,955 A | 10/1988 | Brayten et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,979,507 A | 12/1990 | Heinz et al. |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,052,388 A | 10/1991 | Sivula et al. |
| 5,054,496 A | 10/1991 | Wen et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon et al. |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,311,873 A | 5/1994 | Savard et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,960 A | 7/1994 | Lavine |
| 5,331,966 A | 7/1994 | Bennett et al. |
| 5,334,220 A | 8/1994 | Sholder |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,443,492 A | 8/1995 | Stokes et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,485,849 A | 1/1996 | Panescu et al. |
| 5,514,163 A | 5/1996 | Markowitz et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,552,645 A | 9/1996 | Weng |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,620,466 A | 4/1997 | Haefner et al. |
| 5,628,778 A | 5/1997 | Kruse et al. |
| 5,634,938 A | 6/1997 | Swanson et al. |
| 5,649,968 A | 7/1997 | Alt et al. |
| 5,662,688 A | 9/1997 | Haefner et al. |
| 5,671,752 A | 9/1997 | Sinderby et al. |
| 5,674,259 A | 10/1997 | Gray |
| 5,683,426 A | 11/1997 | Greenhut et al. |
| 5,683,429 A | 11/1997 | Mehra |
| 5,683,432 A | 11/1997 | Goedeke et al. |
| 5,687,737 A | 11/1997 | Branham et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |

(56)        References Cited

U.S. PATENT DOCUMENTS

| | | | |
|---|---|---|---|
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,810,740 A | 9/1998 | Paisner |
| 5,814,089 A | 9/1998 | Stokes et al. |
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,876,336 A | 3/1999 | Swanson et al. |
| 5,891,045 A | 4/1999 | Albrecht et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,922,014 A | 7/1999 | Warman et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,448 A | 4/2000 | Anderson et al. |
| 6,055,454 A | 4/2000 | Heemels |
| 6,070,104 A | 5/2000 | Hine et al. |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,128,535 A | 10/2000 | Maarse et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,187,032 B1 | 2/2001 | Ohyu et al. |
| 6,201,993 B1 | 3/2001 | Kruse et al. |
| 6,205,357 B1 | 3/2001 | Ideker et al. |
| 6,208,894 B1 | 3/2001 | Schulman et al. |
| 6,211,799 B1 | 4/2001 | Post et al. |
| 6,221,011 B1 | 4/2001 | Bardy |
| 6,226,542 B1 | 5/2001 | Reisfeld |
| 6,236,883 B1 | 5/2001 | Ciaccio et al. |
| 6,240,316 B1 | 5/2001 | Richmond et al. |
| 6,240,317 B1 | 5/2001 | Villaseca et al. |
| 6,243,603 B1 | 6/2001 | Ideker et al. |
| 6,246,898 B1 | 6/2001 | Vesely et al. |
| 6,256,534 B1 | 7/2001 | Dahl |
| 6,256,537 B1 | 7/2001 | Stoop et al. |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,301,496 B1 | 10/2001 | Reisfeld |
| 6,307,751 B1 | 10/2001 | Bodony et al. |
| 6,311,089 B1 | 10/2001 | Mann et al. |
| 6,312,378 B1 | 11/2001 | Bardy |
| 6,315,721 B2 | 11/2001 | Schulman et al. |
| 6,330,476 B1 | 12/2001 | Ben-Haim et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,358,214 B1 | 3/2002 | Tereschouk |
| 6,361,780 B1 | 3/2002 | Ley et al. |
| 6,368,284 B1 | 4/2002 | Bardy |
| 6,371,922 B1 | 4/2002 | Baumann et al. |
| 6,377,856 B1 | 4/2002 | Carson |
| 6,381,493 B1 | 4/2002 | Stadler et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,418,346 B1 | 7/2002 | Nelson et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,442,433 B1 | 8/2002 | Linberg |
| 6,443,891 B1 | 9/2002 | Grevious |
| 6,445,953 B1 | 9/2002 | Bulkes et al. |
| 6,453,200 B1 | 9/2002 | Koslar |
| 6,456,867 B2 | 9/2002 | Reisfeld |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,473,638 B2 | 10/2002 | Ferek-Petric |
| 6,480,745 B2 | 11/2002 | Nelson et al. |
| 6,484,118 B1 | 11/2002 | Govari |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,756 B1 | 1/2003 | Heynen et al. |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,532,379 B2 | 3/2003 | Stratbucker |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |

(56)                     References Cited

U.S. PATENT DOCUMENTS

| | | | |
|---|---|---|---|
| 6,561,975 | B1 | 5/2003 | Pool et al. |
| 6,564,807 | B1 | 5/2003 | Schulman et al. |
| 6,574,506 | B2 | 6/2003 | Kramer et al. |
| 6,584,343 | B1 | 6/2003 | Ransbury et al. |
| 6,584,351 | B1 | 6/2003 | Ekwall |
| 6,584,352 | B2 | 6/2003 | Combs et al. |
| 6,597,948 | B1 | 7/2003 | Rockwell et al. |
| 6,597,951 | B2 | 7/2003 | Kramer et al. |
| 6,599,250 | B2 | 7/2003 | Webb et al. |
| 6,622,046 | B2 | 9/2003 | Fraley et al. |
| 6,623,518 | B2 | 9/2003 | Thompson et al. |
| 6,625,482 | B1 | 9/2003 | Panescu et al. |
| 6,628,985 | B2 | 9/2003 | Sweeney et al. |
| 6,640,136 | B1 | 10/2003 | Helland et al. |
| 6,647,292 | B1 | 11/2003 | Bardy et al. |
| 6,650,927 | B1 | 11/2003 | Keidar |
| 6,666,844 | B1 | 12/2003 | Igo et al. |
| 6,689,117 | B2 | 2/2004 | Sweeney et al. |
| 6,690,959 | B2 | 2/2004 | Thompson |
| 6,694,189 | B2 | 2/2004 | Begemann |
| 6,704,602 | B2 | 3/2004 | Berg et al. |
| 6,718,212 | B2 | 4/2004 | Parry et al. |
| 6,721,597 | B1 | 4/2004 | Bardy et al. |
| 6,738,670 | B1 | 5/2004 | Almendinger et al. |
| 6,746,797 | B2 | 6/2004 | Benson et al. |
| 6,749,566 | B2 | 6/2004 | Russ |
| 6,754,528 | B2 | 6/2004 | Bardy et al. |
| 6,758,810 | B2 | 7/2004 | Lebel et al. |
| 6,763,269 | B2 | 7/2004 | Cox |
| 6,766,189 | B2 | 7/2004 | Yu et al. |
| 6,772,004 | B2 | 8/2004 | Rudy |
| 6,778,860 | B2 | 8/2004 | Ostroff et al. |
| 6,788,971 | B1 | 9/2004 | Sloman et al. |
| 6,788,974 | B2 | 9/2004 | Bardy et al. |
| 6,804,555 | B2 | 10/2004 | Warkentin |
| 6,804,558 | B2 | 10/2004 | Haller et al. |
| 6,807,442 | B1 | 10/2004 | Myklebust et al. |
| 6,847,836 | B1 | 1/2005 | Sujdak |
| 6,847,844 | B2 | 1/2005 | Sun et al. |
| 6,856,830 | B2 | 2/2005 | He |
| 6,869,404 | B2 | 3/2005 | Schulhauser et al. |
| 6,871,095 | B2 | 3/2005 | Stahmann et al. |
| 6,871,096 | B2 | 3/2005 | Hill |
| 6,878,112 | B2 | 4/2005 | Linberg et al. |
| 6,882,882 | B2 | 4/2005 | Struble et al. |
| 6,885,889 | B2 | 4/2005 | Chinchoy |
| 6,892,094 | B2 | 5/2005 | Ousdigian et al. |
| 6,897,788 | B2 | 5/2005 | Khair et al. |
| 6,904,315 | B2 | 6/2005 | Panken et al. |
| 6,915,149 | B2 | 7/2005 | Ben-Haim |
| 6,922,592 | B2 | 7/2005 | Thompson et al. |
| 6,931,282 | B2 | 8/2005 | Esler |
| 6,931,286 | B2 | 8/2005 | Sigg et al. |
| 6,934,585 | B1 | 8/2005 | Schloss et al. |
| 6,941,169 | B2 | 9/2005 | Pappu |
| 6,957,107 | B2 | 10/2005 | Rogers et al. |
| 6,968,237 | B2 | 11/2005 | Doan et al. |
| 6,975,900 | B2 | 12/2005 | Rudy et al. |
| 6,978,176 | B2 | 12/2005 | Lattouf |
| 6,978,184 | B1 | 12/2005 | Marcus et al. |
| 6,980,675 | B2 | 12/2005 | Evron et al. |
| 6,985,773 | B2 | 1/2006 | Von Arx et al. |
| 6,990,375 | B2 | 1/2006 | Kloss et al. |
| 6,993,389 | B2 | 1/2006 | Ding et al. |
| 7,001,366 | B2 | 2/2006 | Ballard |
| 7,003,350 | B2 | 2/2006 | Denker et al. |
| 7,006,864 | B2 | 2/2006 | Echt et al. |
| 7,013,176 | B2 | 3/2006 | Ding et al. |
| 7,013,178 | B2 | 3/2006 | Reinke et al. |
| 7,016,719 | B2 | 3/2006 | Rudy et al. |
| 7,027,871 | B2 | 4/2006 | Burnes et al. |
| 7,031,711 | B2 | 4/2006 | Brown et al. |
| 7,031,771 | B2 | 4/2006 | Brown et al. |
| 7,031,777 | B2 | 4/2006 | Hine et al. |
| 7,033,350 | B2 | 4/2006 | Bahk et al. |
| 7,035,684 | B2 | 4/2006 | Lee et al. |
| 7,050,849 | B2 | 5/2006 | Echt et al. |
| 7,058,443 | B2 | 6/2006 | Struble |
| 7,060,031 | B2 | 6/2006 | Webb et al. |
| 7,062,315 | B2 | 6/2006 | Koyrakh et al. |
| 7,063,693 | B2 | 6/2006 | Guenst |
| 7,082,336 | B2 | 7/2006 | Ransbury et al. |
| 7,085,606 | B2 | 8/2006 | Flach et al. |
| 7,092,758 | B2 | 8/2006 | Sun et al. |
| 7,092,759 | B2 | 8/2006 | Nehls et al. |
| 7,110,824 | B2 | 9/2006 | Amundson et al. |
| 7,120,504 | B2 | 10/2006 | Osypka |
| 7,130,681 | B2 | 10/2006 | Gebhardt et al. |
| 7,139,613 | B2 | 11/2006 | Reinke et al. |
| 7,142,912 | B2 | 11/2006 | Wagner et al. |
| 7,142,922 | B2 | 11/2006 | Spinelli et al. |
| 7,146,225 | B2 | 12/2006 | Guenst et al. |
| 7,146,226 | B2 | 12/2006 | Lau et al. |
| 7,149,581 | B2 | 12/2006 | Goedeke |
| 7,149,588 | B2 | 12/2006 | Lau et al. |
| 7,158,839 | B2 | 1/2007 | Lau |
| 7,162,307 | B2 | 1/2007 | Patrias |
| 7,164,952 | B2 | 1/2007 | Lau et al. |
| 7,177,700 | B1 | 2/2007 | Cox |
| 7,177,704 | B2 | 2/2007 | Laske et al. |
| 7,181,284 | B2 | 2/2007 | Burnes et al. |
| 7,181,505 | B2 | 2/2007 | Haller et al. |
| 7,184,830 | B2 | 2/2007 | Echt et al. |
| 7,184,835 | B2 | 2/2007 | Kramer et al. |
| 7,186,214 | B2 | 3/2007 | Ness |
| 7,191,015 | B2 | 3/2007 | Lamson et al. |
| 7,200,437 | B1 | 4/2007 | Nabutovsky et al. |
| 7,200,439 | B2 | 4/2007 | Zdeblick et al. |
| 7,206,423 | B1 | 4/2007 | Feng et al. |
| 7,209,785 | B2 | 4/2007 | Kim et al. |
| 7,209,790 | B2 | 4/2007 | Thompson et al. |
| 7,211,884 | B1 | 5/2007 | Davis et al. |
| 7,212,871 | B1 | 5/2007 | Morgan |
| 7,215,998 | B2 | 5/2007 | Wesselink et al. |
| 7,226,440 | B2 | 6/2007 | Gelfand et al. |
| 7,228,183 | B2 | 6/2007 | Sun et al. |
| 7,231,248 | B2 | 6/2007 | Kramer et al. |
| 7,231,253 | B2 | 6/2007 | Tidemand et al. |
| 7,236,821 | B2 | 6/2007 | Cates et al. |
| 7,236,829 | B1 | 6/2007 | Farazi et al. |
| 7,238,158 | B2 | 7/2007 | Abend |
| 7,254,448 | B2 | 8/2007 | Almendinger et al. |
| 7,260,436 | B2 | 8/2007 | Kilgore et al. |
| 7,270,669 | B1 | 9/2007 | Sra |
| 7,272,448 | B1 | 9/2007 | Morgan et al. |
| 7,277,755 | B1 | 10/2007 | Falkenberg et al. |
| 7,280,872 | B1 | 10/2007 | Mosesov et al. |
| 7,286,866 | B2 | 10/2007 | Okerlund et al. |
| 7,288,096 | B2 | 10/2007 | Chin |
| 7,289,847 | B1 | 10/2007 | Gill et al. |
| 7,289,852 | B2 | 10/2007 | Helfinstine et al. |
| 7,289,853 | B1 | 10/2007 | Campbell et al. |
| 7,289,855 | B2 | 10/2007 | Nghiem et al. |
| 7,302,294 | B2 | 11/2007 | Kamath et al. |
| 7,305,266 | B1 | 12/2007 | Kroll |
| 7,307,321 | B1 | 12/2007 | Avanzino |
| 7,308,297 | B2 | 12/2007 | Reddy et al. |
| 7,308,299 | B2 | 12/2007 | Burrell et al. |
| 7,310,556 | B2 | 12/2007 | Bulkes |
| 7,313,444 | B2 | 12/2007 | Pianca et al. |
| 7,317,950 | B2 | 1/2008 | Lee |
| 7,319,905 | B1 | 1/2008 | Morgan et al. |
| 7,321,677 | B2 | 1/2008 | Evron et al. |
| 7,321,798 | B2 | 1/2008 | Muhlenberg et al. |
| 7,333,853 | B2 | 2/2008 | Mazar et al. |
| 7,336,994 | B2 | 2/2008 | Hettrick et al. |
| 7,346,381 | B2 | 3/2008 | Okerlund et al. |
| 7,346,393 | B2 | 3/2008 | Spinelli et al. |
| 7,347,819 | B2 | 3/2008 | Lebel et al. |
| 7,366,572 | B2 | 4/2008 | Heruth et al. |
| 7,373,207 | B2 | 5/2008 | Lattouf |
| 7,384,403 | B2 | 6/2008 | Sherman |
| 7,386,342 | B1 | 6/2008 | Falkenberg et al. |
| 7,386,351 | B2 | 6/2008 | Hine et al. |

(56)  References Cited

U.S. PATENT DOCUMENTS

| | | | |
|---|---|---|---|
| 7,392,090 B2 | 6/2008 | Sweeney et al. |
| 7,398,116 B2 | 7/2008 | Edwards |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,426,412 B1 | 9/2008 | Schecter |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,509,170 B2 | 3/2009 | Zhang et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,616,993 B2 | 11/2009 | Müssig et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,664,550 B2 | 2/2010 | Eick et al. |
| 7,668,596 B2 | 2/2010 | Von Arx et al. |
| 7,682,316 B2 | 3/2010 | Anderson et al. |
| 7,684,863 B2 | 3/2010 | Parikh et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,751,882 B1 | 7/2010 | Helland et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,451 B2 | 8/2010 | Yang et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,787,951 B1 | 8/2010 | Min |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,818,040 B2 | 10/2010 | Spear et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,807 B2 | 12/2010 | Wang |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,860,580 B2 | 12/2010 | Falk et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,806 B2 | 2/2011 | Horrigan et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,889 B2 | 2/2011 | Zhang |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,917,214 B1 | 3/2011 | Gill et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,213 B2 | 5/2011 | Markowitz et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,475 B2 | 5/2011 | Harlev et al. |
| 7,953,482 B2 | 5/2011 | Hess |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,743 B2 | 7/2011 | Rudy et al. |
| 7,983,753 B2 | 7/2011 | Severin |
| 7,991,467 B2 | 8/2011 | Markowitz et al. |

(56)  References Cited

U.S. PATENT DOCUMENTS

| | | | |
|---|---|---|---|
| 7,991,471 B2 | 8/2011 | Ghanem et al. |
| 7,996,063 B2 | 8/2011 | Vass et al. |
| 7,996,070 B2 | 8/2011 | van Dam et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,194 B2 | 8/2011 | Muller |
| 8,010,209 B2 | 8/2011 | Jacobson |
| 8,014,861 B2 | 9/2011 | Zhu et al. |
| 8,019,402 B1 | 9/2011 | Kryzpow et al. |
| 8,019,409 B2 | 9/2011 | Rosenberg et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,032,229 B2 | 10/2011 | Gerber et al. |
| 8,036,743 B2 * | 10/2011 | Savage ............... A61N 1/3686 |
| | | 607/5 |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,075,486 B2 | 12/2011 | Tal |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,513 B2 | 4/2012 | Chinchoy |
| 8,150,521 B2 | 4/2012 | Crowley et al. |
| 8,160,672 B2 | 4/2012 | Kim et al. |
| 8,160,700 B1 | 4/2012 | Ryu et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,703 B2 | 5/2012 | Dong et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,292 B2 | 6/2012 | Rosenberg et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,213,693 B1 | 7/2012 | Li |
| 8,214,041 B2 | 7/2012 | Van Gelder et al. |
| 8,214,043 B2 | 7/2012 | Matos |
| 8,224,244 B2 | 7/2012 | Kim et al. |

| | | | |
|---|---|---|---|
| 8,229,556 B2 | 7/2012 | Li |
| 8,233,985 B2 | 7/2012 | Bulkes et al. |
| 8,262,578 B1 | 9/2012 | Bharmi et al. |
| 8,265,736 B2 | 9/2012 | Sathaye et al. |
| 8,265,738 B1 | 9/2012 | Min et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,377 B2 | 10/2012 | Rosenberg et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,295,943 B2 | 10/2012 | Eggen et al. |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,326,419 B2 | 12/2012 | Rosenberg et al. |
| 8,332,030 B2 | 12/2012 | Hess et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,308 B2 | 2/2013 | Rosenberg et al. |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,388 B2 | 7/2013 | Nguyen et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,896 B2 | 8/2013 | Doerr et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,051 B1 | 9/2013 | Hedberg et al. |
| 8,527,068 B2 | 9/2013 | Ostroff |
| 8,532,790 B2 | 9/2013 | Griswold |

(56)                    References Cited

U.S. PATENT DOCUMENTS

| | | | |
|---|---|---|---|
| 8,538,526 | B2 | 9/2013 | Stahmann et al. |
| 8,541,131 | B2 | 9/2013 | Lund et al. |
| 8,543,205 | B2 | 9/2013 | Ostroff |
| 8,547,248 | B2 | 10/2013 | Zdeblick et al. |
| 8,548,605 | B2 | 10/2013 | Ollivier |
| 8,554,333 | B2 | 10/2013 | Wu et al. |
| 8,565,882 | B2 | 10/2013 | Matoes |
| 8,565,897 | B2 | 10/2013 | Regnier et al. |
| 8,571,678 | B2 | 10/2013 | Wang |
| 8,577,327 | B2 | 11/2013 | Makdissi et al. |
| 8,583,230 | B2 | 11/2013 | Ryu et al. |
| 8,588,926 | B2 | 11/2013 | Moore et al. |
| 8,594,775 | B2 | 11/2013 | Ghosh et al. |
| 8,612,002 | B2 | 12/2013 | Faltys et al. |
| 8,615,298 | B2 | 12/2013 | Ghosh et al. |
| 8,615,310 | B2 | 12/2013 | Khairkhahan et al. |
| 8,617,082 | B2 | 12/2013 | Zhang et al. |
| 8,620,433 | B2 | 12/2013 | Ghosh et al. |
| 8,626,280 | B2 | 1/2014 | Allavatam et al. |
| 8,626,294 | B2 | 1/2014 | Sheldon et al. |
| 8,634,908 | B2 | 1/2014 | Cowan |
| 8,634,912 | B2 | 1/2014 | Bornzin et al. |
| 8,634,919 | B1 | 1/2014 | Hou et al. |
| 8,639,333 | B2 | 1/2014 | Stadler et al. |
| 8,639,335 | B2 | 1/2014 | Peichel et al. |
| 8,644,934 | B2 | 2/2014 | Hastings et al. |
| 8,649,859 | B2 | 2/2014 | Smith et al. |
| 8,670,842 | B1 | 3/2014 | Bornzin et al. |
| 8,676,314 | B2 | 3/2014 | Maskara et al. |
| 8,676,319 | B2 | 3/2014 | Knoll |
| 8,676,335 | B2 | 3/2014 | Katoozi et al. |
| 8,694,099 | B2 | 4/2014 | Ghosh et al. |
| 8,700,173 | B2 | 4/2014 | Edlund |
| 8,700,181 | B2 | 4/2014 | Bornzin et al. |
| 8,705,599 | B2 | 4/2014 | Dal Molin et al. |
| 8,718,766 | B2 | 5/2014 | Wahlberg |
| 8,718,773 | B2 | 5/2014 | Willis et al. |
| 8,725,260 | B2 | 5/2014 | Shuros et al. |
| 8,731,632 | B1 | 5/2014 | Zarkh et al. |
| 8,731,642 | B2 | 5/2014 | Zarkh et al. |
| 8,738,132 | B1 | 5/2014 | Ghosh et al. |
| 8,738,133 | B2 | 5/2014 | Shuros et al. |
| 8,738,147 | B2 | 5/2014 | Hastings et al. |
| 8,744,555 | B2 | 6/2014 | Allavatam et al. |
| 8,744,572 | B1 | 6/2014 | Greenhut et al. |
| 8,744,576 | B2 | 6/2014 | Munsterman et al. |
| 8,747,314 | B2 | 6/2014 | Stahmann et al. |
| 8,750,994 | B2 | 6/2014 | Ghosh et al. |
| 8,750,998 | B1 | 6/2014 | Ghosh et al. |
| 8,755,884 | B2 | 6/2014 | Demmer et al. |
| 8,758,365 | B2 | 6/2014 | Bonner et al. |
| 8,768,459 | B2 | 7/2014 | Ghosh et al. |
| 8,768,465 | B2 | 7/2014 | Ghosh et al. |
| 8,768,483 | B2 | 7/2014 | Schmitt et al. |
| 8,774,572 | B2 | 7/2014 | Hamamoto |
| 8,781,582 | B2 | 7/2014 | Ziegler et al. |
| 8,781,605 | B2 | 7/2014 | Bornzin et al. |
| 8,788,035 | B2 | 7/2014 | Jacobson |
| 8,788,053 | B2 | 7/2014 | Jacobson |
| 8,798,740 | B2 | 8/2014 | Samade et al. |
| 8,798,745 | B2 | 8/2014 | Jacobson |
| 8,798,762 | B2 | 8/2014 | Fain et al. |
| 8,798,770 | B2 | 8/2014 | Reddy |
| 8,805,504 | B2 | 8/2014 | Sweeney |
| 8,805,505 | B1 | 8/2014 | Roberts |
| 8,805,528 | B2 | 8/2014 | Corndorf |
| 8,812,109 | B2 | 8/2014 | Blomqvist et al. |
| 8,818,504 | B2 | 8/2014 | Bodner et al. |
| 8,827,913 | B2 | 9/2014 | Havel et al. |
| 8,831,747 | B1 | 9/2014 | Min et al. |
| 8,855,789 | B2 | 10/2014 | Jacobson |
| 8,861,830 | B2 | 10/2014 | Brada et al. |
| 8,868,186 | B2 | 10/2014 | Kroll |
| 8,886,307 | B2 | 11/2014 | Sambelashvili et al. |
| 8,886,311 | B2 | 11/2014 | Anderson et al. |
| 8,886,339 | B2 | 11/2014 | Faltys et al. |
| 8,903,473 | B2 | 12/2014 | Rogers et al. |
| 8,903,513 | B2 | 12/2014 | Ollivier |
| 8,909,336 | B2 | 12/2014 | Navarro-Paredes et al. |
| 8,914,131 | B2 | 12/2014 | Bornzin et al. |
| 8,923,795 | B2 | 12/2014 | Makdissi et al. |
| 8,923,963 | B2 | 12/2014 | Bonner et al. |
| 8,929,984 | B2 | 1/2015 | Ghosh et al. |
| 8,938,300 | B2 | 1/2015 | Rosero |
| 8,942,806 | B2 | 1/2015 | Sheldon et al. |
| 8,948,869 | B2 | 2/2015 | Ghosh et al. |
| 8,948,883 | B2 | 2/2015 | Eggen et al. |
| 8,958,892 | B2 | 2/2015 | Khairkhahan et al. |
| 8,965,489 | B2 | 2/2015 | Ghosh |
| 8,972,228 | B2 | 3/2015 | Ghosh et al. |
| 8,977,358 | B2 | 3/2015 | Ewert et al. |
| 8,989,873 | B2 | 3/2015 | Locsin |
| 8,996,109 | B2 | 3/2015 | Karst et al. |
| 9,002,454 | B2 | 4/2015 | Ghosh et al. |
| 9,002,467 | B2 | 4/2015 | Smith et al. |
| 9,008,776 | B2 | 4/2015 | Cowan et al. |
| 9,008,777 | B2 | 4/2015 | Dianaty et al. |
| 9,014,818 | B2 | 4/2015 | Deterre et al. |
| 9,017,341 | B2 | 4/2015 | Bornzin et al. |
| 9,020,611 | B2 | 4/2015 | Khairkhahan et al. |
| 9,031,642 | B2 | 5/2015 | Ghosh |
| 9,033,996 | B1 | 5/2015 | West |
| 9,037,238 | B2 | 5/2015 | Stadler et al. |
| 9,037,262 | B2 | 5/2015 | Regnier et al. |
| 9,042,984 | B2 | 5/2015 | Demmer et al. |
| 9,060,699 | B2 | 6/2015 | Nearing et al. |
| 9,072,872 | B2 | 7/2015 | Asleson et al. |
| 9,072,911 | B2 | 7/2015 | Hastings et al. |
| 9,072,913 | B2 | 7/2015 | Jacobson |
| 9,101,281 | B2 | 8/2015 | Reinert et al. |
| 9,119,959 | B2 | 9/2015 | Rys et al. |
| 9,155,882 | B2 | 10/2015 | Grubac et al. |
| 9,155,897 | B2 | 10/2015 | Ghosh et al. |
| 9,168,372 | B2 | 10/2015 | Fain |
| 9,168,380 | B1 | 10/2015 | Greenhut et al. |
| 9,168,383 | B2 | 10/2015 | Jacobson et al. |
| 9,180,285 | B2 | 11/2015 | Moore et al. |
| 9,192,774 | B2 | 11/2015 | Jacobson |
| 9,199,087 | B2 | 12/2015 | Stadler et al. |
| 9,205,225 | B2 | 12/2015 | Khairkhahan et al. |
| 9,216,285 | B1 | 12/2015 | Boling et al. |
| 9,216,293 | B2 | 12/2015 | Berthiaume et al. |
| 9,216,298 | B2 | 12/2015 | Jacobson |
| 9,227,077 | B2 | 1/2016 | Jacobson |
| 9,238,145 | B2 | 1/2016 | Wenzel et al. |
| 9,242,102 | B2 | 1/2016 | Khairkhahan et al. |
| 9,242,113 | B2 | 1/2016 | Smith et al. |
| 9,248,300 | B2 | 2/2016 | Rys et al. |
| 9,265,436 | B2 | 2/2016 | Min et al. |
| 9,265,951 | B2 | 2/2016 | Sweeney |
| 9,265,954 | B2 | 2/2016 | Ghosh |
| 9,265,955 | B2 | 2/2016 | Ghosh |
| 9,265,962 | B2 | 2/2016 | Dianaty et al. |
| 9,272,148 | B2 | 3/2016 | Ghosh |
| 9,272,155 | B2 | 3/2016 | Ostroff |
| 9,278,218 | B2 | 3/2016 | Karst et al. |
| 9,278,219 | B2 | 3/2016 | Ghosh |
| 9,278,220 | B2 | 3/2016 | Ghosh |
| 9,278,229 | B1 | 3/2016 | Reinke et al. |
| 9,282,907 | B2 | 3/2016 | Ghosh |
| 9,283,381 | B2 | 3/2016 | Grubac et al. |
| 9,283,382 | B2 | 3/2016 | Berthiaume et al. |
| 9,289,612 | B1 | 3/2016 | Sambelashbili et al. |
| 9,302,115 | B2 | 4/2016 | Molin et al. |
| 9,320,446 | B2 | 4/2016 | Gillberg et al. |
| 9,333,364 | B2 | 5/2016 | Echt et al. |
| 9,358,387 | B2 | 6/2016 | Suwito et al. |
| 9,358,400 | B2 | 6/2016 | Jacobson |
| 9,364,675 | B2 | 6/2016 | Deterre et al. |
| 9,370,663 | B2 | 6/2016 | Moulder |
| 9,375,580 | B2 | 6/2016 | Bonner et al. |
| 9,375,581 | B2 | 6/2016 | Baru et al. |
| 9,381,362 | B2 | 7/2016 | Ghosh et al. |
| 9,381,365 | B2 | 7/2016 | Kibler et al. |

(56) References Cited

U.S. PATENT DOCUMENTS

| | | | |
|---|---|---|---|
| 9,393,424 B2 | 7/2016 | Demmer et al. | |
| 9,393,436 B2 | 7/2016 | Doerr | |
| 9,399,139 B2 | 7/2016 | Demmer et al. | |
| 9,399,140 B2 | 7/2016 | Cho et al. | |
| 9,409,033 B2 | 8/2016 | Jacobson | |
| 9,427,594 B1 | 8/2016 | Bornzin et al. | |
| 9,433,368 B2 | 9/2016 | Stahmann et al. | |
| 9,433,780 B2 | 9/2016 | Regnier et al. | |
| 9,457,193 B2 | 10/2016 | Klimovitch et al. | |
| 9,474,457 B2 | 10/2016 | Ghosh et al. | |
| 9,486,151 B2 | 11/2016 | Ghosh et al. | |
| 9,492,668 B2 | 11/2016 | Sheldon et al. | |
| 9,492,669 B2 | 11/2016 | Demmer et al. | |
| 9,492,674 B2 | 11/2016 | Schmidt et al. | |
| 9,492,677 B2 | 11/2016 | Greenhut et al. | |
| 9,510,763 B2 | 12/2016 | Ghosh et al. | |
| 9,511,233 B2 | 12/2016 | Sambelashvili | |
| 9,511,236 B2 | 12/2016 | Varady et al. | |
| 9,511,237 B2 | 12/2016 | Deterre et al. | |
| 9,517,336 B2 | 12/2016 | Eggen et al. | |
| 9,522,276 B2 | 12/2016 | Shen et al. | |
| 9,522,280 B2 | 12/2016 | Fishler et al. | |
| 9,526,435 B2 | 12/2016 | Ghosh | |
| 9,526,522 B2 | 12/2016 | Wood et al. | |
| 9,526,891 B2 | 12/2016 | Eggen et al. | |
| 9,526,909 B2 | 12/2016 | Stahmann et al. | |
| 9,533,163 B2 | 1/2017 | Klimovitch et al. | |
| 9,561,382 B2 | 2/2017 | Persson et al. | |
| 9,566,012 B2 | 2/2017 | Greenhut et al. | |
| 9,579,500 B2 | 2/2017 | Rys et al. | |
| 9,586,050 B2 | 3/2017 | Ghosh et al. | |
| 9,586,052 B2 | 3/2017 | Gillberg et al. | |
| 9,591,982 B2 | 3/2017 | Ghosh et al. | |
| 9,603,651 B2 | 3/2017 | Ghosh | |
| 9,610,045 B2 | 4/2017 | Du et al. | |
| 9,623,234 B2 | 4/2017 | Anderson | |
| 9,636,511 B2 | 5/2017 | Carney et al. | |
| 9,643,014 B2 | 5/2017 | Zhang et al. | |
| 9,675,579 B2 | 6/2017 | Rock et al. | |
| 9,700,728 B2 | 7/2017 | Ghosh | |
| 9,707,399 B2 | 7/2017 | Zielinski et al. | |
| 9,724,519 B2 | 8/2017 | Demmer et al. | |
| 9,737,223 B2 | 8/2017 | Du et al. | |
| 9,750,941 B2 | 9/2017 | Ghosh | |
| 9,757,567 B2 | 9/2017 | Ghosh et al. | |
| 9,764,143 B2 | 9/2017 | Ghosh et al. | |
| 9,776,009 B2 | 10/2017 | Ghosh et al. | |
| 9,782,094 B2 | 10/2017 | Du et al. | |
| 9,789,319 B2 | 10/2017 | Sambelashvili | |
| 9,808,628 B2 | 11/2017 | Sheldon et al. | |
| 9,808,633 B2 | 11/2017 | Bonner et al. | |
| 9,877,789 B2 | 1/2018 | Ghosh | |
| 9,901,732 B2 | 2/2018 | Sommer et al. | |
| 9,924,884 B2 | 3/2018 | Ghosh et al. | |
| 9,962,097 B2 | 5/2018 | Ghosh et al. | |
| 9,974,457 B2 | 5/2018 | Ghosh et al. | |
| 9,986,951 B1 * | 6/2018 | Ferdosi | A61B 5/352 |
| 10,004,467 B2 | 6/2018 | Lahm et al. | |
| 10,022,060 B2 | 7/2018 | Nearing et al. | |
| 10,039,305 B2 | 8/2018 | Asleson et al. | |
| 10,064,567 B2 | 9/2018 | Ghosh et al. | |
| 10,092,744 B2 | 10/2018 | Sommer et al. | |
| 10,099,050 B2 | 10/2018 | Chen et al. | |
| 10,154,794 B2 | 12/2018 | Stadler et al. | |
| 10,166,396 B2 | 1/2019 | Schrock et al. | |
| 10,206,601 B2 | 2/2019 | Gillberg et al. | |
| 10,251,555 B2 | 4/2019 | Ghosh et al. | |
| 10,315,028 B2 | 6/2019 | Sommer et al. | |
| 10,406,370 B1 | 9/2019 | Makharinsky | |
| 10,456,581 B2 | 10/2019 | Liu et al. | |
| 10,463,853 B2 | 11/2019 | Drake et al. | |
| 10,478,627 B2 | 11/2019 | Muessig | |
| 10,602,944 B2 * | 3/2020 | Cole | A61B 5/349 |
| 10,773,085 B2 * | 9/2020 | Ghosh | A61N 1/365 |
| 10,780,279 B2 | 9/2020 | Ghosh | |
| 10,850,108 B2 | 12/2020 | Li et al. | |
| 2002/0032470 A1 | 3/2002 | Linberg | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072682 A1 | 6/2002 | Hopman et al. | |
| 2002/0072773 A1 | 6/2002 | Bardy et al. | |
| 2002/0082665 A1 | 6/2002 | Haller et al. | |
| 2002/0087089 A1 | 7/2002 | Ben-Haim | |
| 2002/0091414 A1 | 7/2002 | Bardy et al. | |
| 2002/0095196 A1 | 7/2002 | Linberg | |
| 2002/0099423 A1 | 7/2002 | Berg et al. | |
| 2002/0103510 A1 | 8/2002 | Bardy et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0120299 A1 | 8/2002 | Ostroff et al. | |
| 2002/0143264 A1 | 10/2002 | Ding et al. | |
| 2002/0161307 A1 | 10/2002 | Yu et al. | |
| 2002/0169484 A1 | 11/2002 | Mathis et al. | |
| 2002/0173830 A1 | 11/2002 | Starkweather et al. | |
| 2002/0193846 A1 | 12/2002 | Pool et al. | |
| 2003/0004549 A1 | 1/2003 | Hill et al. | |
| 2003/0009203 A1 | 1/2003 | Lebel et al. | |
| 2003/0018277 A1 | 1/2003 | He | |
| 2003/0028082 A1 | 2/2003 | Thompson | |
| 2003/0040779 A1 | 2/2003 | Engmark et al. | |
| 2003/0041866 A1 | 3/2003 | Linberg et al. | |
| 2003/0045805 A1 | 3/2003 | Sheldon et al. | |
| 2003/0050670 A1 | 3/2003 | Spinelli et al. | |
| 2003/0083104 A1 | 5/2003 | Bonner et al. | |
| 2003/0088278 A1 | 5/2003 | Bardy et al. | |
| 2003/0092995 A1 | 5/2003 | Thompson | |
| 2003/0097153 A1 | 5/2003 | Bardy et al. | |
| 2003/0105495 A1 | 6/2003 | Yu et al. | |
| 2003/0105497 A1 | 6/2003 | Zhu et al. | |
| 2003/0114908 A1 | 6/2003 | Flach | |
| 2003/0144701 A1 | 7/2003 | Mehra et al. | |
| 2003/0187460 A1 | 10/2003 | Chin et al. | |
| 2003/0187461 A1 | 10/2003 | Chin | |
| 2003/0204233 A1 | 10/2003 | Laske et al. | |
| 2003/0236466 A1 | 12/2003 | Tarjan et al. | |
| 2004/0015081 A1 | 1/2004 | Kramer et al. | |
| 2004/0024435 A1 | 2/2004 | Leckrone et al. | |
| 2004/0059237 A1 | 3/2004 | Narayan et al. | |
| 2004/0064158 A1 | 4/2004 | Klein | |
| 2004/0068302 A1 | 4/2004 | Rodgers et al. | |
| 2004/0087938 A1 | 5/2004 | Leckrone et al. | |
| 2004/0088035 A1 | 5/2004 | Guenst et al. | |
| 2004/0097806 A1 | 5/2004 | Hunter et al. | |
| 2004/0102812 A1 | 5/2004 | Yonce et al. | |
| 2004/0102830 A1 | 5/2004 | Williams | |
| 2004/0122479 A1 | 6/2004 | Spinelli et al. | |
| 2004/0127959 A1 | 7/2004 | Amundson et al. | |
| 2004/0133242 A1 | 7/2004 | Chapman et al. | |
| 2004/0147969 A1 | 7/2004 | Mann et al. | |
| 2004/0147973 A1 | 7/2004 | Hauser | |
| 2004/0162496 A1 | 8/2004 | Yu et al. | |
| 2004/0167558 A1 | 8/2004 | Igo et al. | |
| 2004/0167587 A1 | 8/2004 | Thompson | |
| 2004/0172071 A1 | 9/2004 | Bardy et al. | |
| 2004/0172077 A1 | 9/2004 | Chinchoy | |
| 2004/0172078 A1 | 9/2004 | Chinchoy | |
| 2004/0172079 A1 | 9/2004 | Chinchoy | |
| 2004/0172104 A1 | 9/2004 | Berg et al. | |
| 2004/0176817 A1 | 9/2004 | Wahlstrand et al. | |
| 2004/0176818 A1 | 9/2004 | Wahlstrand et al. | |

(56)                    References Cited

U.S. PATENT DOCUMENTS

| | | |
|---|---|---|
| 2004/0176830 A1 | 9/2004 | Fang |
| 2004/0186529 A1 | 9/2004 | Bardy et al. |
| 2004/0193223 A1 | 9/2004 | Kramer et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215245 A1 | 10/2004 | Stahmann et al. |
| 2004/0215252 A1 | 10/2004 | Verbeek et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220635 A1 | 11/2004 | Burnes |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0090870 A1 | 4/2005 | Hine et al. |
| 2005/0096522 A1 | 5/2005 | Reddy et al. |
| 2005/0102003 A1 | 5/2005 | Grabek et al. |
| 2005/0107839 A1 | 5/2005 | Sanders |
| 2005/0137629 A1 | 6/2005 | Dyjach et al. |
| 2005/0137638 A1 | 6/2005 | Yonce et al. |
| 2005/0137671 A1 | 6/2005 | Liu |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0224198 A1 | 10/2006 | Dong et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0253162 A1 | 11/2006 | Zhang et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049975 A1 | 3/2007 | Cates et al. |
| 2007/0060802 A1* | 3/2007 | Ghevondian ........ A61B 5/6831 |
| | | 600/301 |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jaconson |
| 2007/0135882 A1 | 6/2007 | Drasler et al. |
| 2007/0135883 A1 | 6/2007 | Drasler et al. |
| 2007/0142871 A1 | 6/2007 | Libbus et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0167809 A1 | 7/2007 | Dala-Krishna |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0232943 A1 | 10/2007 | Harel et al. |
| 2007/0233206 A1 | 10/2007 | Frikart et al. |
| 2007/0233216 A1 | 10/2007 | Liu |
| 2007/0239244 A1 | 10/2007 | Morgan et al. |
| 2007/0250129 A1 | 10/2007 | Van Oort |
| 2007/0255376 A1 | 11/2007 | Michels et al. |
| 2007/0265508 A1 | 11/2007 | Sheikhzadeh-Nadjar et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021336 A1 | 1/2008 | Dobak et al. |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0058656 A1 | 3/2008 | Costello et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0082136 A1 | 4/2008 | Gaudiani |
| 2008/0103539 A1 | 5/2008 | Stegemann et al. |
| 2008/0109054 A1 | 5/2008 | Hastings et al. |
| 2008/0119903 A1 | 5/2008 | Arcot-Krishnamurthy et al. |
| 2008/0119911 A1 | 5/2008 | Rosero |
| 2008/0130670 A1 | 6/2008 | Kim et al. |
| 2008/0140143 A1 | 6/2008 | Ettori et al. |
| 2008/0146954 A1 | 6/2008 | Bojovic et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0242976 A1 | 10/2008 | Robertson et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269818 A1 | 10/2008 | Sullivan et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0281195 A1 | 11/2008 | Heimdal |
| 2008/0288008 A1 | 11/2008 | Lee |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0048646 A1 | 2/2009 | Katoozi et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0084382 A1 | 4/2009 | Jalde et al. |
| 2009/0088813 A1 | 4/2009 | Brockway et al. |
| 2009/0093857 A1 | 4/2009 | Markowitz et al. |

(56) References Cited

U.S. PATENT DOCUMENTS

| | | | |
|---|---|---|---|
| 2009/0099468 A1 | 4/2009 | Thiagalingam et al. | |
| 2009/0099469 A1 | 4/2009 | Flores | |
| 2009/0099619 A1 | 4/2009 | Lessmeier et al. | |
| 2009/0112109 A1 | 4/2009 | Kuklik et al. | |
| 2009/0131907 A1 | 5/2009 | Chin et al. | |
| 2009/0135886 A1 | 5/2009 | Robertson et al. | |
| 2009/0143835 A1 | 6/2009 | Pastore et al. | |
| 2009/0143838 A1 | 6/2009 | Libbus et al. | |
| 2009/0157134 A1 | 6/2009 | Ziglio et al. | |
| 2009/0157136 A1 | 6/2009 | Yang et al. | |
| 2009/0171408 A1 | 7/2009 | Solem | |
| 2009/0171414 A1 | 7/2009 | Kelly et al. | |
| 2009/0198298 A1 | 8/2009 | Kaiser et al. | |
| 2009/0204163 A1 | 8/2009 | Shuros et al. | |
| 2009/0204170 A1 | 8/2009 | Hastings et al. | |
| 2009/0210024 A1 | 8/2009 | Jason | |
| 2009/0216112 A1 | 8/2009 | Assis et al. | |
| 2009/0216144 A1* | 8/2009 | Hopenfeld | A61B 5/349 |
| | | | 600/521 |
| 2009/0216292 A1 | 8/2009 | Pless et al. | |
| 2009/0232448 A1 | 9/2009 | Barmash et al. | |
| 2009/0234407 A1 | 9/2009 | Hastings et al. | |
| 2009/0234411 A1 | 9/2009 | Sambelashvili et al. | |
| 2009/0234412 A1 | 9/2009 | Sambelashvili | |
| 2009/0234413 A1 | 9/2009 | Sambelashvili et al. | |
| 2009/0234414 A1 | 9/2009 | Sambelashvili et al. | |
| 2009/0234415 A1 | 9/2009 | Sambelashvili et al. | |
| 2009/0248103 A1 | 10/2009 | Sambelashvili et al. | |
| 2009/0254140 A1 | 10/2009 | Rosenberg et al. | |
| 2009/0259272 A1 | 10/2009 | Reddy et al. | |
| 2009/0266573 A1 | 10/2009 | Engmark et al. | |
| 2009/0270729 A1 | 10/2009 | Corbucci et al. | |
| 2009/0270937 A1 | 10/2009 | Yonce et al. | |
| 2009/0275998 A1 | 11/2009 | Burnes et al. | |
| 2009/0275999 A1 | 11/2009 | Burnes et al. | |
| 2009/0299201 A1 | 12/2009 | Gunderson | |
| 2009/0299423 A1 | 12/2009 | Min | |
| 2009/0299447 A1 | 12/2009 | Jensen et al. | |
| 2009/0306732 A1 | 12/2009 | Rosenberg et al. | |
| 2009/0318995 A1 | 12/2009 | Keel et al. | |
| 2010/0013668 A1 | 1/2010 | Kantervik | |
| 2010/0016911 A1 | 1/2010 | Willis et al. | |
| 2010/0016914 A1 | 1/2010 | Mullen et al. | |
| 2010/0016917 A1 | 1/2010 | Efimov et al. | |
| 2010/0022873 A1 | 1/2010 | Hunter et al. | |
| 2010/0023078 A1 | 1/2010 | Dong et al. | |
| 2010/0023085 A1 | 1/2010 | Wu et al. | |
| 2010/0030061 A1 | 2/2010 | Canfield et al. | |
| 2010/0030327 A1 | 2/2010 | Chatel | |
| 2010/0042108 A1 | 2/2010 | Hibino | |
| 2010/0049063 A1 | 2/2010 | Dobak, III | |
| 2010/0063375 A1 | 3/2010 | Kassab et al. | |
| 2010/0063562 A1 | 3/2010 | Cowan et al. | |
| 2010/0065871 A1 | 3/2010 | Govari et al. | |
| 2010/0069987 A1 | 3/2010 | Min et al. | |
| 2010/0087888 A1 | 4/2010 | Maskara | |
| 2010/0094149 A1 | 4/2010 | Kohut et al. | |
| 2010/0094367 A1 | 4/2010 | Sen | |
| 2010/0113954 A1 | 5/2010 | Zhou | |
| 2010/0114209 A1 | 5/2010 | Krause et al. | |
| 2010/0114214 A1 | 5/2010 | Morelli et al. | |
| 2010/0114229 A1 | 5/2010 | Chinchoy | |
| 2010/0121403 A1 | 5/2010 | Schecter et al. | |
| 2010/0125281 A1 | 5/2010 | Jacobson et al. | |
| 2010/0145405 A1 | 6/2010 | Min et al. | |
| 2010/0152798 A1 | 6/2010 | Sanghera et al. | |
| 2010/0168761 A1 | 7/2010 | Kassab et al. | |
| 2010/0168819 A1 | 7/2010 | Freeberg | |
| 2010/0174137 A1 | 7/2010 | Shim | |
| 2010/0185250 A1 | 7/2010 | Rom | |
| 2010/0198288 A1 | 8/2010 | Ostroff | |
| 2010/0198291 A1 | 8/2010 | Sambelashvili et al. | |
| 2010/0198292 A1 | 8/2010 | Honeck et al. | |
| 2010/0198304 A1 | 8/2010 | Wang | |
| 2010/0217367 A1 | 8/2010 | Belson | |

| | | | |
|---|---|---|---|
| 2010/0228138 A1 | 9/2010 | Chen | |
| 2010/0228308 A1 | 9/2010 | Cowan et al. | |
| 2010/0234906 A1 | 9/2010 | Koh | |
| 2010/0234916 A1 | 9/2010 | Turcott et al. | |
| 2010/0234924 A1 | 9/2010 | Willis | |
| 2010/0241185 A1 | 9/2010 | Mahapatra et al. | |
| 2010/0249622 A1 | 9/2010 | Olson | |
| 2010/0249729 A1 | 9/2010 | Morris et al. | |
| 2010/0254583 A1 | 10/2010 | Chan et al. | |
| 2010/0268059 A1 | 10/2010 | Ryu et al. | |
| 2010/0286541 A1 | 11/2010 | Musley et al. | |
| 2010/0286626 A1 | 11/2010 | Petersen | |
| 2010/0286744 A1 | 11/2010 | Echt et al. | |
| 2010/0298841 A1 | 11/2010 | Prinzen et al. | |
| 2010/0312309 A1 | 12/2010 | Harding | |
| 2010/0318147 A1 | 12/2010 | Forslund | |
| 2011/0004111 A1 | 1/2011 | Gill et al. | |
| 2011/0004264 A1 | 1/2011 | Siejko et al. | |
| 2011/0014510 A1 | 1/2011 | Miyashisa et al. | |
| 2011/0022112 A1 | 1/2011 | Min | |
| 2011/0022113 A1 | 1/2011 | Ideblick et al. | |
| 2011/0054286 A1 | 3/2011 | Crosby | |
| 2011/0054559 A1 | 3/2011 | Rosenberg et al. | |
| 2011/0054560 A1 | 3/2011 | Rosenberg et al. | |
| 2011/0071586 A1 | 3/2011 | Jacobson | |
| 2011/0075896 A1 | 3/2011 | Matsumoto | |
| 2011/0077708 A1 | 3/2011 | Ostroff | |
| 2011/0092809 A1 | 4/2011 | Nguyen et al. | |
| 2011/0106202 A1 | 5/2011 | Ding et al. | |
| 2011/0112398 A1 | 5/2011 | Zarkh et al. | |
| 2011/0112600 A1 | 5/2011 | Cowan et al. | |
| 2011/0118588 A1 | 5/2011 | Komblau et al. | |
| 2011/0118803 A1 | 5/2011 | Hou et al. | |
| 2011/0118810 A1 | 5/2011 | Cowan et al. | |
| 2011/0137187 A1 | 6/2011 | Yang et al. | |
| 2011/0137369 A1 | 6/2011 | Ryu et al. | |
| 2011/0144510 A1 | 6/2011 | Ryu et al. | |
| 2011/0144720 A1 | 6/2011 | Cowan et al. | |
| 2011/0152970 A1 | 6/2011 | Jollota et al. | |
| 2011/0160558 A1 | 6/2011 | Rassatt et al. | |
| 2011/0160565 A1 | 6/2011 | Stubbs | |
| 2011/0160801 A1 | 6/2011 | Markowitz et al. | |
| 2011/0160806 A1 | 6/2011 | Lyden et al. | |
| 2011/0166620 A1 | 7/2011 | Cowan et al. | |
| 2011/0166621 A1 | 7/2011 | Cowan et al. | |
| 2011/0172728 A1 | 7/2011 | Wang | |
| 2011/0184297 A1* | 7/2011 | Vitali | A61B 5/316 |
| | | | 600/509 |
| 2011/0184491 A1 | 7/2011 | Kivi | |
| 2011/0190615 A1 | 8/2011 | Phillips et al. | |
| 2011/0190835 A1 | 8/2011 | Brockway et al. | |
| 2011/0190841 A1 | 8/2011 | Sambelashvili et al. | |
| 2011/0196444 A1 | 8/2011 | Prakash et al. | |
| 2011/0201915 A1 | 8/2011 | Gogin et al. | |
| 2011/0208260 A1 | 8/2011 | Jacobson | |
| 2011/0213260 A1 | 9/2011 | Keel et al. | |
| 2011/0218587 A1 | 9/2011 | Jacobson | |
| 2011/0230734 A1 | 9/2011 | Fain et al. | |
| 2011/0237967 A1 | 9/2011 | Moore et al. | |
| 2011/0245890 A1 | 10/2011 | Brisben et al. | |
| 2011/0251660 A1 | 10/2011 | Griswold | |
| 2011/0251662 A1 | 10/2011 | Griswold et al. | |
| 2011/0270099 A1 | 11/2011 | Ruben et al. | |
| 2011/0270339 A1 | 11/2011 | Murray, III et al. | |
| 2011/0270340 A1 | 11/2011 | Pellegrini et al. | |
| 2011/0276102 A1 | 11/2011 | Cohen | |
| 2011/0282423 A1 | 11/2011 | Jacobson | |
| 2011/0319954 A1 | 12/2011 | Niazi et al. | |
| 2012/0004527 A1 | 1/2012 | Thompson et al. | |
| 2012/0004567 A1 | 1/2012 | Eberle et al. | |
| 2012/0029323 A1 | 2/2012 | Zhao | |
| 2012/0035685 A1 | 2/2012 | Saha et al. | |
| 2012/0041508 A1 | 2/2012 | Rousso et al. | |
| 2012/0059433 A1 | 3/2012 | Cowan et al. | |
| 2012/0059436 A1 | 3/2012 | Fontaine et al. | |
| 2012/0065500 A1 | 3/2012 | Rogers et al. | |
| 2012/0078129 A1 | 3/2012 | Bailin | |
| 2012/0078322 A1 | 3/2012 | Dal Molin et al. | |
| 2012/0089198 A1 | 4/2012 | Ostroff | |

(56) References Cited

U.S. PATENT DOCUMENTS

| | | | |
|---|---|---|---|
| 2012/0089214 A1 | 4/2012 | Kroll et al. | |
| 2012/0093245 A1 | 4/2012 | Makdissi et al. | |
| 2012/0095521 A1 | 4/2012 | Hintz | |
| 2012/0095539 A1 | 4/2012 | Khairkhahan et al. | |
| 2012/0101540 A1 | 4/2012 | O'Brien et al. | |
| 2012/0101543 A1 | 4/2012 | Demmer et al. | |
| 2012/0101546 A1 | 4/2012 | Stadler et al. | |
| 2012/0101553 A1 | 4/2012 | Reddy | |
| 2012/0109148 A1 | 5/2012 | Bonner et al. | |
| 2012/0109149 A1 | 5/2012 | Bonner et al. | |
| 2012/0109235 A1 | 5/2012 | Sheldon et al. | |
| 2012/0109236 A1 | 5/2012 | Jacobson et al. | |
| 2012/0109244 A1 | 5/2012 | Anderson et al. | |
| 2012/0109259 A1 | 5/2012 | Bond et al. | |
| 2012/0116489 A1 | 5/2012 | Khairkhahan et al. | |
| 2012/0150251 A1 | 6/2012 | Giftakis et al. | |
| 2012/0158111 A1 | 6/2012 | Khairkhahan et al. | |
| 2012/0165827 A1 | 6/2012 | Khairkhahan et al. | |
| 2012/0172690 A1 | 7/2012 | Anderson et al. | |
| 2012/0172891 A1 | 7/2012 | Lee | |
| 2012/0172892 A1 | 7/2012 | Grubac et al. | |
| 2012/0172942 A1 | 7/2012 | Berg | |
| 2012/0179221 A1 | 7/2012 | Reddy et al. | |
| 2012/0197350 A1 | 8/2012 | Roberts et al. | |
| 2012/0197373 A1 | 8/2012 | Khairkhahan et al. | |
| 2012/0203090 A1 | 8/2012 | Min | |
| 2012/0209126 A1* | 8/2012 | Amos .................... | A61B 5/332 |
| | | | 600/479 |
| 2012/0215285 A1 | 8/2012 | Tahmasian et al. | |
| 2012/0232478 A1 | 9/2012 | Haslinger | |
| 2012/0232563 A1 | 9/2012 | Williams | |
| 2012/0232565 A1 | 9/2012 | Kveen et al. | |
| 2012/0245665 A1 | 9/2012 | Friedman et al. | |
| 2012/0253419 A1 | 10/2012 | Rosenberg et al. | |
| 2012/0263218 A1 | 10/2012 | Dal Molin et al. | |
| 2012/0277600 A1 | 11/2012 | Greenhut | |
| 2012/0277606 A1 | 11/2012 | Ellingson et al. | |
| 2012/0277725 A1 | 11/2012 | Kassab | |
| 2012/0283587 A1 | 11/2012 | Ghosh et al. | |
| 2012/0283795 A1 | 11/2012 | Stancer et al. | |
| 2012/0283807 A1 | 11/2012 | Deterre et al. | |
| 2012/0284003 A1 | 11/2012 | Gosh et al. | |
| 2012/0290025 A1 | 11/2012 | Keimel | |
| 2012/0296228 A1 | 11/2012 | Zhang et al. | |
| 2012/0296381 A1 | 11/2012 | Matos | |
| 2012/0296387 A1 | 11/2012 | Zhang et al. | |
| 2012/0296388 A1 | 11/2012 | Zhang et al. | |
| 2012/0302904 A1 | 11/2012 | Lian et al. | |
| 2012/0303082 A1 | 11/2012 | Dong et al. | |
| 2012/0303084 A1 | 11/2012 | Kleckner et al. | |
| 2012/0310297 A1 | 12/2012 | Sweeney | |
| 2012/0316613 A1 | 12/2012 | Keefe et al. | |
| 2012/0330179 A1 | 12/2012 | Yuk et al. | |
| 2013/0006332 A1 | 1/2013 | Sommer et al. | |
| 2013/0012151 A1 | 1/2013 | Hankins | |
| 2013/0013017 A1 | 1/2013 | Mullen et al. | |
| 2013/0018250 A1 | 1/2013 | Caprio et al. | |
| 2013/0018251 A1 | 1/2013 | Caprio et al. | |
| 2013/0023975 A1 | 1/2013 | Locsin | |
| 2013/0030491 A1 | 1/2013 | Stadler et al. | |
| 2013/0035748 A1 | 2/2013 | Bonner et al. | |
| 2013/0041422 A1 | 2/2013 | Jacobson | |
| 2013/0053906 A1 | 2/2013 | Ghosh et al. | |
| 2013/0053908 A1 | 2/2013 | Smith et al. | |
| 2013/0053915 A1 | 2/2013 | Holmstrom et al. | |
| 2013/0053921 A1 | 2/2013 | Bonner et al. | |
| 2013/0060298 A1 | 3/2013 | Splett et al. | |
| 2013/0066169 A1 | 3/2013 | Rys et al. | |
| 2013/0072770 A1 | 3/2013 | Rao et al. | |
| 2013/0072790 A1 | 3/2013 | Ludwig et al. | |
| 2013/0079798 A1 | 3/2013 | Tran et al. | |
| 2013/0079861 A1 | 3/2013 | Reinert et al. | |
| 2013/0085350 A1 | 4/2013 | Schugt et al. | |
| 2013/0085403 A1 | 4/2013 | Gunderson et al. | |
| 2013/0085550 A1 | 4/2013 | Polefko et al. | |
| 2013/0096446 A1 | 4/2013 | Michael et al. | |
| 2013/0096649 A1 | 4/2013 | Martin et al. | |
| 2013/0103047 A1 | 4/2013 | Steingisser et al. | |
| 2013/0103109 A1 | 4/2013 | Jacobson | |
| 2013/0110008 A1 | 5/2013 | Bourg et al. | |
| 2013/0110127 A1 | 5/2013 | Bornzin et al. | |
| 2013/0110192 A1 | 5/2013 | Tran et al. | |
| 2013/0110219 A1 | 5/2013 | Bornzin et al. | |
| 2013/0116529 A1 | 5/2013 | Min et al. | |
| 2013/0116738 A1 | 5/2013 | Samade et al. | |
| 2013/0116739 A1 | 5/2013 | Brada et al. | |
| 2013/0116740 A1 | 5/2013 | Bornzin et al. | |
| 2013/0116741 A1 | 5/2013 | Bornzin et al. | |
| 2013/0123872 A1 | 5/2013 | Bornzin et al. | |
| 2013/0123875 A1 | 5/2013 | Varady et al. | |
| 2013/0131529 A1 | 5/2013 | Jia et al. | |
| 2013/0131591 A1 | 5/2013 | Berthiaume et al. | |
| 2013/0131693 A1 | 5/2013 | Berthiaume et al. | |
| 2013/0131749 A1 | 5/2013 | Sheldon et al. | |
| 2013/0131750 A1 | 5/2013 | Stadler et al. | |
| 2013/0131751 A1 | 5/2013 | Stadler et al. | |
| 2013/0136035 A1 | 5/2013 | Bange et al. | |
| 2013/0138006 A1 | 5/2013 | Bornzin et al. | |
| 2013/0150695 A1 | 6/2013 | Biela et al. | |
| 2013/0150911 A1 | 6/2013 | Perschbacher et al. | |
| 2013/0150912 A1 | 6/2013 | Perschbacher et al. | |
| 2013/0150913 A1 | 6/2013 | Bornzin et al. | |
| 2013/0165983 A1 | 6/2013 | Ghosh et al. | |
| 2013/0165988 A1 | 6/2013 | Ghosh | |
| 2013/0184776 A1 | 7/2013 | Shuros et al. | |
| 2013/0196703 A1 | 8/2013 | Masoud et al. | |
| 2013/0197599 A1 | 8/2013 | Sambelashvili et al. | |
| 2013/0197609 A1 | 8/2013 | Moore et al. | |
| 2013/0231710 A1 | 9/2013 | Jacobson | |
| 2013/0238072 A1 | 9/2013 | Deterre et al. | |
| 2013/0238073 A1 | 9/2013 | Makdissi et al. | |
| 2013/0253342 A1 | 9/2013 | Griswold et al. | |
| 2013/0253343 A1 | 9/2013 | Walfhauser et al. | |
| 2013/0253344 A1 | 9/2013 | Griswold et al. | |
| 2013/0253345 A1 | 9/2013 | Griswold et al. | |
| 2013/0253346 A1 | 9/2013 | Griswold et al. | |
| 2013/0253347 A1 | 9/2013 | Griswold et al. | |
| 2013/0261471 A1 | 10/2013 | Saha et al. | |
| 2013/0261497 A1 | 10/2013 | Pertijs et al. | |
| 2013/0261688 A1 | 10/2013 | Dong et al. | |
| 2013/0265144 A1 | 10/2013 | Banna et al. | |
| 2013/0268017 A1 | 10/2013 | Zhang et al. | |
| 2013/0268042 A1 | 10/2013 | Hastings et al. | |
| 2013/0274828 A1 | 10/2013 | Willis | |
| 2013/0274847 A1 | 10/2013 | Ostroff | |
| 2013/0282070 A1 | 10/2013 | Cowan et al. | |
| 2013/0282073 A1 | 10/2013 | Cowan et al. | |
| 2013/0289640 A1 | 10/2013 | Zhang et al. | |
| 2013/0296726 A1 | 11/2013 | Niebauer et al. | |
| 2013/0296727 A1 | 11/2013 | Sullivan et al. | |
| 2013/0303872 A1 | 11/2013 | Taff et al. | |
| 2013/0304407 A1 | 11/2013 | George et al. | |
| 2013/0324825 A1 | 12/2013 | Ostroff et al. | |
| 2013/0324828 A1 | 12/2013 | Nishiwaki et al. | |
| 2013/0325081 A1 | 12/2013 | Karst et al. | |
| 2013/0345770 A1 | 12/2013 | Dianaty et al. | |
| 2014/0005563 A1 | 1/2014 | Ramanathan et al. | |
| 2014/0012344 A1 | 1/2014 | Hastings et al. | |
| 2014/0018872 A1 | 1/2014 | Siejko et al. | |
| 2014/0018876 A1 | 1/2014 | Ostroff | |
| 2014/0018877 A1 | 1/2014 | Demmer et al. | |
| 2014/0031836 A1 | 1/2014 | Ollivier | |
| 2014/0039591 A1 | 2/2014 | Drasler et al. | |
| 2014/0043146 A1 | 2/2014 | Makdissi et al. | |
| 2014/0046395 A1 | 2/2014 | Regnier et al. | |
| 2014/0046420 A1 | 2/2014 | Moore et al. | |
| 2014/0058240 A1 | 2/2014 | Mothilal et al. | |
| 2014/0058494 A1 | 2/2014 | Ostroff et al. | |
| 2014/0074114 A1 | 3/2014 | Khairkhahan et al. | |
| 2014/0074186 A1 | 3/2014 | Faltys et al. | |
| 2014/0094891 A1 | 4/2014 | Pare et al. | |
| 2014/0100627 A1 | 4/2014 | Min | |
| 2014/0107507 A1 | 4/2014 | Ghosh et al. | |
| 2014/0107723 A1 | 4/2014 | Hou et al. | |

(56)           References Cited

U.S. PATENT DOCUMENTS

| | | | |
|---|---|---|---|
| 2014/0114173 A1 | 4/2014 | Bar-Tal et al. | |
| 2014/0114372 A1 | 4/2014 | Ghosh et al. | |
| 2014/0121719 A1 | 5/2014 | Bonner et al. | |
| 2014/0121720 A1 | 5/2014 | Bonner et al. | |
| 2014/0121722 A1 | 5/2014 | Sheldon et al. | |
| 2014/0128711 A1* | 5/2014 | Banet | A61B 5/024 |
| | | | 600/513 |
| 2014/0128935 A1 | 5/2014 | Kumar et al. | |
| 2014/0135865 A1 | 5/2014 | Hastings et al. | |
| 2014/0135866 A1 | 5/2014 | Ramanathan et al. | |
| 2014/0135867 A1 | 5/2014 | Demmer et al. | |
| 2014/0142648 A1 | 5/2014 | Smith et al. | |
| 2014/0148675 A1 | 5/2014 | Nordstrom et al. | |
| 2014/0148815 A1 | 5/2014 | Wenzel et al. | |
| 2014/0155950 A1 | 6/2014 | Hastings et al. | |
| 2014/0163633 A1 | 6/2014 | Ghosh et al. | |
| 2014/0169162 A1 | 6/2014 | Romano et al. | |
| 2014/0172060 A1 | 6/2014 | Bornzin et al. | |
| 2014/0180306 A1 | 6/2014 | Grubac et al. | |
| 2014/0180366 A1 | 6/2014 | Edlund | |
| 2014/0207149 A1 | 7/2014 | Hastings et al. | |
| 2014/0207210 A1 | 7/2014 | Willis et al. | |
| 2014/0214104 A1 | 7/2014 | Greenhut et al. | |
| 2014/0222098 A1 | 8/2014 | Baru et al. | |
| 2014/0222099 A1 | 8/2014 | Sweeney | |
| 2014/0222109 A1 | 8/2014 | Moulder | |
| 2014/0228913 A1 | 8/2014 | Molin et al. | |
| 2014/0236172 A1 | 8/2014 | Hastings et al. | |
| 2014/0236252 A1 | 8/2014 | Ghosh et al. | |
| 2014/0243848 A1 | 8/2014 | Auricchio et al. | |
| 2014/0255298 A1 | 9/2014 | Cole et al. | |
| 2014/0257324 A1 | 9/2014 | Fain | |
| 2014/0257422 A1 | 9/2014 | Herken | |
| 2014/0257444 A1 | 9/2014 | Cole et al. | |
| 2014/0276125 A1 | 9/2014 | Hou et al. | |
| 2014/0276929 A1 | 9/2014 | Foster et al. | |
| 2014/0277233 A1 | 9/2014 | Ghosh | |
| 2014/0303704 A1 | 10/2014 | Suwito et al. | |
| 2014/0309706 A1 | 10/2014 | Jacobson | |
| 2014/0323882 A1 | 10/2014 | Ghosh et al. | |
| 2014/0323892 A1 | 10/2014 | Ghosh et al. | |
| 2014/0323893 A1 | 10/2014 | Ghosh et al. | |
| 2014/0330208 A1 | 11/2014 | Christie et al. | |
| 2014/0330287 A1 | 11/2014 | Thompson-Nauman et al. | |
| 2014/0330326 A1 | 11/2014 | Thompson-Nauman et al. | |
| 2014/0339570 A1 | 11/2014 | Mollard et al. | |
| 2014/0358135 A1 | 12/2014 | Sambelashvili et al. | |
| 2014/0371807 A1 | 12/2014 | Ghosh et al. | |
| 2014/0371808 A1 | 12/2014 | Ghosh et al. | |
| 2014/0371832 A1 | 12/2014 | Ghosh et al. | |
| 2014/0371833 A1 | 12/2014 | Ghosh et al. | |
| 2014/0379041 A1 | 12/2014 | Foster | |
| 2015/0025612 A1 | 1/2015 | Haasl et al. | |
| 2015/0032016 A1 | 1/2015 | Ghosh | |
| 2015/0032171 A1 | 1/2015 | Ghosh | |
| 2015/0032172 A1 | 1/2015 | Ghosh | |
| 2015/0032173 A1 | 1/2015 | Ghosh | |
| 2015/0039041 A1 | 2/2015 | Smith et al. | |
| 2015/0045849 A1 | 2/2015 | Ghosh et al. | |
| 2015/0051609 A1 | 2/2015 | Schmidt et al. | |
| 2015/0051610 A1 | 2/2015 | Schmidt et al. | |
| 2015/0051611 A1 | 2/2015 | Schmidt et al. | |
| 2015/0051612 A1 | 2/2015 | Schmidt et al. | |
| 2015/0051613 A1 | 2/2015 | Schmidt et al. | |
| 2015/0051614 A1 | 2/2015 | Schmidt et al. | |
| 2015/0051615 A1 | 2/2015 | Schmidt et al. | |
| 2015/0051616 A1 | 2/2015 | Haasl et al. | |
| 2015/0051682 A1 | 2/2015 | Schmidt et al. | |
| 2015/0057520 A1 | 2/2015 | Foster et al. | |
| 2015/0057558 A1 | 2/2015 | Stahmann et al. | |
| 2015/0057721 A1 | 2/2015 | Stahmann et al. | |
| 2015/0088155 A1 | 3/2015 | Foster et al. | |
| 2015/0105836 A1 | 4/2015 | Bonner et al. | |
| 2015/0142069 A1 | 5/2015 | Sambelashvili | |
| 2015/0142070 A1 | 5/2015 | Sambelashvili | |
| 2015/0148697 A1 | 5/2015 | Burnes et al. | |
| 2015/0149096 A1 | 5/2015 | Soykan | |
| 2015/0157225 A1 | 6/2015 | Gillberg et al. | |
| 2015/0157231 A1 | 6/2015 | Gillberg et al. | |
| 2015/0157232 A1 | 6/2015 | Gillberg et al. | |
| 2015/0157861 A1 | 6/2015 | Aghassian | |
| 2015/0157865 A1 | 6/2015 | Gillberg et al. | |
| 2015/0173655 A1 | 6/2015 | Demmer et al. | |
| 2015/0190638 A1 | 7/2015 | Smith et al. | |
| 2015/0196756 A1 | 7/2015 | Stahmann et al. | |
| 2015/0196757 A1 | 7/2015 | Stahmann et al. | |
| 2015/0196758 A1 | 7/2015 | Stahmann et al. | |
| 2015/0196769 A1 | 7/2015 | Stahmann et al. | |
| 2015/0216434 A1 | 8/2015 | Ghosh et al. | |
| 2015/0217119 A1 | 8/2015 | Nikolski et al. | |
| 2015/0221898 A1 | 8/2015 | Chi et al. | |
| 2015/0224315 A1 | 8/2015 | Stahmann | |
| 2015/0224320 A1 | 8/2015 | Stahmann | |
| 2015/0258345 A1 | 9/2015 | Smith et al. | |
| 2015/0265840 A1 | 9/2015 | Ghosh et al. | |
| 2015/0290468 A1 | 10/2015 | Zhang | |
| 2015/0297905 A1 | 10/2015 | Greenhut et al. | |
| 2015/0297907 A1 | 10/2015 | Zhang | |
| 2015/0305637 A1 | 10/2015 | Greenhut et al. | |
| 2015/0305638 A1 | 10/2015 | Zhang | |
| 2015/0305639 A1 | 10/2015 | Greenhut et al. | |
| 2015/0305640 A1 | 10/2015 | Reinke et al. | |
| 2015/0305641 A1 | 10/2015 | Stadler et al. | |
| 2015/0305642 A1 | 10/2015 | Reinke et al. | |
| 2015/0305695 A1 | 10/2015 | Lahm et al. | |
| 2015/0306374 A1 | 10/2015 | Seifert et al. | |
| 2015/0306375 A1 | 10/2015 | Marshall et al. | |
| 2015/0306406 A1 | 10/2015 | Crutchfield et al. | |
| 2015/0306407 A1 | 10/2015 | Crutchfield et al. | |
| 2015/0306408 A1 | 10/2015 | Greenhut et al. | |
| 2015/0321016 A1 | 11/2015 | O'Brien et al. | |
| 2015/0328459 A1 | 11/2015 | Chin et al. | |
| 2015/0335894 A1 | 11/2015 | Bornzin et al. | |
| 2016/0015287 A1 | 1/2016 | Anderson et al. | |
| 2016/0015322 A1 | 1/2016 | Anderson et al. | |
| 2016/0022164 A1 | 1/2016 | Brockway et al. | |
| 2016/0023000 A1 | 1/2016 | Cho et al. | |
| 2016/0030747 A1 | 2/2016 | Thakur et al. | |
| 2016/0030751 A1 | 2/2016 | Ghosh et al. | |
| 2016/0030757 A1 | 2/2016 | Jacobson | |
| 2016/0033177 A1 | 2/2016 | Barot et al. | |
| 2016/0045737 A1 | 2/2016 | Ghosh et al. | |
| 2016/0045738 A1 | 2/2016 | Ghosh et al. | |
| 2016/0045744 A1 | 2/2016 | Gillberg et al. | |
| 2016/0051821 A1 | 2/2016 | Sambelashvili et al. | |
| 2016/0059002 A1 | 3/2016 | Grubac et al. | |
| 2016/0067486 A1 | 3/2016 | Brown et al. | |
| 2016/0067487 A1 | 3/2016 | Demmer et al. | |
| 2016/0067490 A1 | 3/2016 | Carney et al. | |
| 2016/0110856 A1 | 4/2016 | Hoof et al. | |
| 2016/0114161 A1 | 4/2016 | Amblard et al. | |
| 2016/0121127 A1 | 5/2016 | Klimovitch et al. | |
| 2016/0121128 A1 | 5/2016 | Fishler et al. | |
| 2016/0121129 A1 | 5/2016 | Persson et al. | |
| 2016/0129239 A1 | 5/2016 | Anderson | |
| 2016/0184590 A1 | 6/2016 | Ghosh | |
| 2016/0213919 A1 | 7/2016 | Suwito et al. | |
| 2016/0213937 A1 | 7/2016 | Reinke et al. | |
| 2016/0213939 A1 | 7/2016 | Carney et al. | |
| 2016/0228026 A1 | 8/2016 | Jackson | |
| 2016/0256063 A1* | 9/2016 | Friedman | A61B 5/02455 |
| 2016/0310733 A1 | 10/2016 | Sheldon et al. | |
| 2016/0317825 A1 | 11/2016 | Jacobson | |
| 2016/0331258 A1* | 11/2016 | Du | A61B 5/349 |
| 2016/0339248 A1 | 11/2016 | Schrock et al. | |
| 2016/0367823 A1 | 12/2016 | Cowan et al. | |
| 2017/0014629 A1 | 1/2017 | Ghosh et al. | |
| 2017/0035315 A1 | 2/2017 | Jackson | |
| 2017/0043173 A1 | 2/2017 | Sharma et al. | |
| 2017/0043174 A1 | 2/2017 | Greenhut et al. | |
| 2017/0049347 A1 | 2/2017 | Ghosh et al. | |
| 2017/0056670 A1 | 3/2017 | Sheldon et al. | |
| 2017/0071675 A1 | 3/2017 | Dawoud et al. | |
| 2017/0172428 A1* | 6/2017 | Banet | A61B 5/02028 |

(56)  References Cited

U.S. PATENT DOCUMENTS

| | | | |
|---|---|---|---|
| 2017/0172517 A1* | 6/2017 | Banet ................... A61B 5/0537 |
| 2017/0182327 A1 | 6/2017 | Liu |
| 2017/0189681 A1 | 7/2017 | Anderson |
| 2017/0209689 A1 | 7/2017 | Chen |
| 2017/0216575 A1 | 8/2017 | Asleson et al. |
| 2017/0246460 A1 | 8/2017 | Ghosh |
| 2017/0246461 A1 | 8/2017 | Ghosh |
| 2017/0303840 A1 | 10/2017 | Stadler et al. |
| 2017/0304624 A1 | 10/2017 | Friedman et al. |
| 2017/0326369 A1 | 11/2017 | Koop et al. |
| 2017/0326372 A1 | 11/2017 | Koop et al. |
| 2017/0340885 A1 | 11/2017 | Sambelashvili |
| 2018/0008829 A1 | 1/2018 | An et al. |
| 2018/0020938 A1 | 1/2018 | Du et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140847 A1 | 5/2018 | Taff et al. |
| 2018/0140848 A1 | 5/2018 | Stahmann |
| 2018/0178007 A1 | 6/2018 | Shuros et al. |
| 2018/0199843 A1 | 7/2018 | Ghosh et al. |
| 2018/0212451 A1 | 7/2018 | Schmidt et al. |
| 2018/0250514 A1 | 9/2018 | Ghosh |
| 2018/0256904 A1 | 9/2018 | Li et al. |
| 2018/0263522 A1* | 9/2018 | Ghosh .................... A61B 5/308 |
| 2018/0264258 A1 | 9/2018 | Cheng et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0272121 A1 | 9/2018 | Yankelson |
| 2018/0280686 A1 | 10/2018 | Shuros et al. |
| 2018/0326215 A1 | 11/2018 | Ghosh |
| 2019/0030331 A1 | 1/2019 | Ghosh et al. |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |
| 2019/0143117 A1 | 5/2019 | Ghosh |
| 2019/0160288 A1 | 5/2019 | Stegemann et al. |
| 2019/0183370 A1 | 6/2019 | Gillberg et al. |
| 2019/0192023 A1 | 6/2019 | Ghosh |
| 2019/0192860 A1 | 6/2019 | Ghosh et al. |
| 2019/0192863 A1 | 6/2019 | Koop et al. |
| 2019/0269926 A1 | 9/2019 | Ghosh |
| 2019/0290905 A1 | 9/2019 | Yang et al. |
| 2019/0290909 A1 | 9/2019 | Ghosh et al. |
| 2019/0298903 A1 | 10/2019 | Gillberg et al. |
| 2019/0298990 A1 | 10/2019 | De Kock et al. |
| 2019/0314636 A1 | 10/2019 | Shuros et al. |
| 2019/0336032 A1* | 11/2019 | Gill .................... A61B 5/02405 |
| 2019/0351236 A1 | 11/2019 | Koop |
| 2020/0016418 A1 | 1/2020 | Makharinsky |
| 2020/0069949 A1 | 3/2020 | Ghosh |
| 2020/0245889 A1* | 8/2020 | Telenkov ............. A61B 5/6885 |
| 2021/0361219 A1* | 11/2021 | Fischer ................ A61N 1/0484 |
| 2024/0138744 A1* | 5/2024 | Omer .................... A61B 5/364 |

FOREIGN PATENT DOCUMENTS

| | | |
|---|---|---|
| AU | 2014203793 A1 | 7/2014 |
| CN | 1043621 A | 7/1990 |
| CN | 1253761 A | 5/2000 |
| CN | 1878595 A | 12/2006 |
| CN | 101073502 A | 11/2007 |
| CN | 202933393 | 5/2013 |
| EP | 362611 A1 | 4/1990 |
| EP | 0459 239 A2 | 12/1991 |
| EP | 0 728 497 A2 | 8/1996 |
| EP | 1 072 284 A2 | 1/2001 |
| EP | 1 504 713 | 2/2005 |
| EP | 1 541 191 A1 | 6/2005 |
| EP | 1 702 648 A1 | 9/2006 |
| EP | 2 016 976 | 1/2009 |
| EP | 1 904 166 B1 | 6/2011 |
| EP | 2 391 270 | 7/2011 |
| EP | 1 925 337 | 3/2012 |
| EP | 2 436 309 A2 | 4/2012 |
| EP | 2 452 721 A1 | 5/2012 |
| EP | 2 471 452 A1 | 7/2012 |
| EP | 2 435 132 | 9/2013 |
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 1998/026712 | 6/1998 |
| WO | WO 1999/006112 | 2/1999 |
| WO | WO 2000/045700 | 8/2000 |
| WO | WO 2001/067950 | 9/2001 |
| WO | WO 02/22206 A1 | 3/2002 |
| WO | WO 2003/070323 | 8/2003 |
| WO | WO 03/092800 A1 | 11/2003 |
| WO | WO 2005/000206 A2 | 1/2005 |
| WO | WO 2005/042089 A1 | 5/2005 |
| WO | WO 2005/056108 A2 | 6/2005 |
| WO | WO 2006/069215 A2 | 6/2006 |
| WO | WO 2006/086435 A2 | 8/2006 |
| WO | WO 2006/105474 A2 | 10/2006 |
| WO | WO 2006/113659 A1 | 10/2006 |
| WO | WO 2006/115777 | 11/2006 |
| WO | WO 2006/116595 A2 | 11/2006 |
| WO | WO 2006/117773 | 11/2006 |
| WO | WO 2007/013994 A2 | 2/2007 |
| WO | WO 2007/027940 A2 | 3/2007 |
| WO | WO 2007/073435 A1 | 6/2007 |
| WO | WO 2007/075974 A2 | 7/2007 |
| WO | WO 2007/139456 | 12/2007 |
| WO | WO 2008/042887 A2 | 4/2008 |
| WO | WO 2008/151077 A2 | 12/2008 |
| WO | WO 2009/006531 A1 | 1/2009 |
| WO | WO 2009/079344 | 6/2009 |
| WO | WO 2009/139911 A2 | 11/2009 |
| WO | WO 2009/148429 | 12/2009 |
| WO | WO 2010/019494 | 2/2010 |
| WO | WO 2010/071520 | 6/2010 |
| WO | WO 2010/088040 | 8/2010 |
| WO | WO 2010/088485 | 8/2010 |
| WO | WO 2011/070166 | 6/2011 |
| WO | WO 2011/090622 | 7/2011 |
| WO | WO 2011/099992 | 8/2011 |
| WO | WO 2012/037471 A2 | 3/2012 |
| WO | WO 2012/106297 A2 | 8/2012 |
| WO | WO 2012/109618 A2 | 8/2012 |
| WO | WO 2012/110940 | 8/2012 |
| WO | WO 2012/151364 | 11/2012 |
| WO | WO 2012/151389 | 11/2012 |
| WO | WO 2013/006724 A2 | 1/2013 |
| WO | WO 2013/010165 | 1/2013 |
| WO | WO 2013/010184 | 1/2013 |
| WO | WO 2013/080038 A2 | 6/2013 |
| WO | WO 2013/098644 A2 | 7/2013 |
| WO | WO 2014/179454 | 11/2014 |
| WO | WO 2014/179459 A2 | 11/2014 |
| WO | WO 2015/013271 | 1/2015 |
| WO | WO 2015/013493 | 1/2015 |
| WO | WO 2015/013574 | 1/2015 |
| WO | WO 2015/081221 A1 | 6/2015 |
| WO | WO 2015/193047 A2 | 12/2015 |
| WO | WO 2016/011042 A1 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | WO 2018/009569 A1 | 1/2018 |
| WO | WO 2018/017226 A1 | 1/2018 |
| WO | WO 2018/017361 A1 | 1/2018 |
| WO | WO 2018/035343 A1 | 2/2018 |

(56)　　　　References Cited

FOREIGN PATENT DOCUMENTS

| | | |
|---|---|---|
| WO | WO 2018/081519 A1 | 5/2018 |
| WO | WO 2019/173599 | 9/2019 |
| WO | WO 2020/058314 | 3/2020 |
| WO | WO 2021/123271 | 6/2021 |

OTHER PUBLICATIONS http://www.isrctn.com/ISRCTN47824547, public posting published Aug. 2019.

Abed et al., "Obesity results in progressive atrial structural and electrical remodeling: Implications for atrial fibrillation," Heart Rhythm Society, Jan. 2013; 10(1):90-100.

Adragão et al., "Ablation of pulmonary vein foci for the treatment of atrial fibrillation; percutaneous electroanatomical guided approach," Europace, Oct. 2002; 4(4):391-9.

Aliot et al., "Arrhythmia detection by dual-chamber implantable cardioverter defibrillators: A review of current algorithms," Europace, Jul. 2004; 6(4):273-86.

Amirahmadi et al., "Ventricular Tachycardia Caused by Mesothelial Cyst," Indian Pacing and Electrophysiology Journal, 2013; 13(1):43-44.

Ammirabile et al., "Pitx2 confers left morphological, molecular, and functional identity to the sinus venosus myocardium," Cardiovasc Res., Feb. 2012; 93(2):291-301.

Anderson et al., "Left bundle branch block and the evolving role of QRS morphology in selection of patients for cardiac resynchronization", Journal of Interventional Cardio Electrophysiology, vol. 52, No. 3. Aug. 20, 2018, pp. 353-374.

Anfinsen, "Non-pharmacological Treatment of Atrial Fibrillation," Indian Pacing and Electrophysiology Journal, Jan. 2002; 2(1):4-14.

Anné et al., "Ablation of post-surgical intra-atrial reentrant Tachycardia," European Heart Journal, 2002; 23:169-1616.

Aquilina, "A Brief History of Cardiac Pacing", Images Paediatr Cardiol. 8 (2), Apr.-Jun. 2006, 117 pages.

Arenal et al., "Dominant frequency differences in atrial fibrillation patients with and without left ventricular systolic dysfunction," Europace, Apr. 2009; 11(4):450-457.

Arriagada et al., "Predictors of arrhythmia recurrence in patients with lone atrial fibrillation," Europace, Jan. 2008; 10(1):9-14.

Asirvatham et al., "Cardiac Anatomic Considerations in Pediatric Electrophysiology," Indian Pacing and Electrophysiology Journal, Apr. 2008; 8(Suppl 1):S75-S91.

Asirvatham et al., "Intramyocardial Pacing and Sensing for the Enhancement of Cardiac Stimulation and Sensing Specificity," Pacing Clin. Electrophysiol., Jun. 2007; 30(6):748-754.

Asirvatham et al., "Letter to the Editor," J Cardiovasc Electrophysiol., Mar. 2010; 21(3): E77.

Balmer et al., "Long-term follow up of children with congenital complete atrioventricular block and the impact of pacemaker therapy," Europace, Oct. 2002; 4(4):345-349.

Barold et al., "Conventional and biventricular pacing in patients with first-degree atrioventricular block," Europace, Oct. 2012; 14(10):1414-9.

Barold et al., "The effect of hyperkalacmia on cardiac rhythm devices," Europace, Apr. 2014; 16(4):467-76.

Bayrak et al., "Added value of transoesophageal echocardiography during transseptal puncture performed by inexperienced operators," Europace, May 2012; 14(5):661-5.

Bergau et al., "Measurement of Left Atrial Pressure is a Good Predictor of Freedom From Atrial Fibrillation," Indian Pacing and Electrophysiology Journal, Jul. 2014; 14(4):181-93.

Bernstein et al., "The revised NASPE/BPEG gencric code for antibradycardia, adaptive-rate, and multisite pacing. North American Society of Pacing and Electrophysiology/British Pacing and Electrophysiology Group," Pacing Clin Electrophysiol., Feb. 2002; 25(2):260-4.

Biffi et al., "Occurrence of Phrenic Nerve Stimulation in Cardiac Resynchronization Therapy Patients: the Role of Left Ventricular Lead Type and Placement Site," Europace, 2013; 15:77-82.

Bito et al., "Early exercise training after myocardial infarction prevents contractile but not electrical remodeling or hypertrophy," Cardiovascular Research, Apr. 2010; 86(1):72-81.

Bollmann et al., "Analysis of surface electrocardiograms in atrial fibrillation: techniques, research, and clinical applications," Europace, Nov. 2006; 8(11):911-926.

Bortolotto et al., "Pre-implantation interlead EKG heterogeneity is superior to QRS complex duration in predicting mechanical super-response and survival in patients receiving cardiac resynchronization therapy", Heart Rhythm, Mar. 10, 2020, 35 pages.

Bortone et al., "Evidence for an incomplete mitral isthmus block after failed ablation of a left postero-inferior concealed accessory pathway," Europace, Jun. 2006; 8(6):434-7.

Botker MD, PhD., et al., "Electromechanical Mapping for Detection of Myocardial Viability in Patients with ischemia Cardiomyopathy," Circulation, Mar. 2001; vol. 103, No. 12, pp.

Boulos et al., "Electroanatomical mapping and radiofrequency ablation of an accessory pathway associated with a large aneurysm of the coronary sinus," Europace, Nov. 2004; 6(6):608-12.

Brembilla-Perrot et al., "Incidence and prognostic significance of spontaneous and inducible antidromic tachycardia," Europace, Jun. 2013; 15(6):871-876.

Buber et al., "Morphological features of the P-waves at surface electrocardiogram as surrogate to mechanical function of the left atrium following a successful modified maze procedure," Europace, Apr. 2014; 16(4):578-86.

Burashnikov et al., "Late-phase 3 EAD. A unique mechanism contributing to initiation of atrial fibrillation," Pacing Clin Electrophysiol., Mar. 2006; 29(3):290-5.

Burashnikov et al., "Atrial-selective inhibition of sodium-channel current by Wenxin Keli is effective in suppressing atrial fibrillation," Heart Rhythm, Jan. 2012; 9(1):125-31.

Calvo et al., "Efficacy of circumferential pulmonary vein ablation of atrial fibrillation in endurance athletes," Europace, Jan. 2010; 12(1):30-6.

Can et al., ""Atrial torsades de pointes" Induced by Low-Energy Shock From Implantable-Cardioverter Defibrillator," Indian Pacing and Electrophysiology Journal, Sep. 2013; 13(5):194-199.

"CardioGuide System Enables Real-Time Navigation of Left Ventricular Leads During Medtronic CRT Implants," Press Release, Apr. 9, 2013, Medtronic, Inc., 2 pgs.

Carroz et al., "Pseudo-pacemaker syndrome in a young woman with first-degree atrio-ventricular block," Europace, Apr. 2010; 12(4):594-596.

Catanchin et al., "Wolff-Parkinson-White syndrome with an unroofed coronary sinus without persistent left superior vena cava treated with catheter cryoablation," Indian Pacing and Electrophysiology Journal, Aug. 2008; 8(3):227-233.

Cazcau et al., "Cardiac resynchronization therapy," Europace, Sep. 2004; 5 Suppl 1:S42-8.

Cerqueira et al., "Standardized myocardial segmentation and nomenclature for tomographic imaging of the heart. A statement for healthcare professionals from the Cardiac Imaging Committee of the Council on Clinical Cardiology of the American Heart Association," Circulation, Jan. 29, 2002; 105(4):539-42.

Chandra et al., "Evaluation of KCB-328, a new IKr blocking antiarrhythmic agent in pacing induced canine atrial fibrillation," Europace, Sep. 2004; 6(5):384-91.

Chang et al., "Electrophysiological characteristics and catheter ablation in patients with paroxysmal supraventricular tachycardia and paroxysmal atrial fibrillation," J Cardiovasc Electrophysiol., Apr. 2008; 19(4):367-73.

Charron et al., "A familial form of conduction defect related to a mutation in the PRKAG2 gene," Europace, Aug. 2007; 9(8):597-600.

Chou et al., "Effects of SEA0400 on Arrhythmogenicity in a Langendorff-Perfused 1-Month Myocardial Infarction Rabbit Model," Pacing Clin Electrophysiol., May 2013; 36(5):596-606.

(56)         References Cited

OTHER PUBLICATIONS

Ciploetta et al., "Posterior Coronary Vein as the Substrate for an Epicardial Accessory Pathway," Indian Pacing and Electrophysiology Journal, Aug. 2013; 13(4):142-7.

Climent et al., "Effects of endocardial microwave energy ablation," Indian Pacing and Electrophysiology Journal, Jul. 2005; 5(3):233-43.

Comtois et al., "Of circles and spirals: bridging the gap between the leading circle and spiral wave concepts of cardiac reentry," Europace, Sep. 2005; 7 Suppl 2:10-20.

Crick et al., "Anatomy of the pig heart: comparisons with normal human cardiac structure," J. Anat., 1998, 193:105-119.

Cuculich, P.S., et al., "The Electrophysiological Cardiac Ventricular Substrate in Patients After Myocardial Infection" J. Am. Coll. Cardiol. 2011; 58:1893-1902.

Czerwinska et al., "Method of Segmentation of Thorax Organs Images Applied to Modeling the Cardiac Electrical Field," Engineering in Medicine and Biology Society, Proceedings of the 22nd Annual International Conference of the IEEE, vol. 1, 23, Jul. 23, 2000.; pp. 402-405.

Daoulah et al., "Unintended Harm and Benefit of the Implantable Defibrillator in an Unfortunate 19-Year-Old Male: Featuring a Sequence of Rare Life-threatening Complications of Cardiac Procedures," Indian Pacing and Electrophysiology Journal, Aug. 2013; 13(4):151-6.

Dawoud, F. et al., "Inverse Electrocardiographic Imaging to Assess Electrical Dyssynchrony in Cardiac Resynchronization Therapy Patients," Computing in Cardiology, 2012; 39:993-996.

De Mattia et al., "Paroxysmal atrial fibrillation triggered by a monomorphic ventricular couplet in a patient with acute coronary syndrome," Indian Pacing and Electrophysiology Journal, Jan. 2012; 12(1):19-23.

DeSimone et al., "New approach to cardiac resynchronization therapy: CRT without left ventricular lead," Apr. 25, 2014, 2 pages.

De Sisti et al., "Electrophysiological determinants of atrial fibrillation in sinus node dysfunction despite atrial pacing," Europace, Oct. 2000; 2(4):304-11.

De Voogt et al., "Electrical characteristics of low atrial septum pacing compared with right atrial appendage pacing," Europace, Jan. 2005; 7(1):60-6.

De Voogt et al., "A technique of lead insertion for low atrial septal pacing," Pacing Clin Electrophysiol., Jul. 2005; 28(7):639-46.

Dizon et al. "Real-time stroke volume measurements for the optimization of cardiac resynchronization therapy parameters," Europace, Sep. 2010; 12(9):1270-1274.

Duckett et al., "Relationship between endocardial activation sequences defined by high-density mapping to early septal contraction (septal flash) in patients with left bundle branch block undergoing cardiac resynchronization therapy," Europace, Jan. 2012; 14(1):99-106.

Eksik et al., "Influence of atrioventricular nodal reentrant tachycardia ablation on right to left inter-atrial conduction," Indian Pacing and Electrophysiology Journal, Oct. 2005; 5(4):279-88.

Fiala et al., "Left Atrial Voltage during Atrial Fibrillation in Paroxysmal and Persistent Atrial Fibrillation Patients," PACE, May 2010; 33(5):541-548.

Fragakis et al., "Acute beta-adrenoceptor blockade improves efficacy of ibutilide in conversion of atrial fibrillation with a rapid ventricular rate," Europace, Jan. 2009; 11(1):70-4.

Freund et al., "A Decision-Theoretic Generalization of Online Learning and an Application to Boosting." Journal of Computer and System Sciences, 1997; 55(1):119-139.

Friedman, "Greedy Function Approximation: A Gradient Boosting Machine," Annals of Statistics, 2001; 29(5):1189-1232.

Friedman, "Stochastic Gradient Boosting," Computational Statistics and Data Analysis, 2002; 38(4):367-378.

Friedman et al., "Additive Logistic Regression: a Statistical View of Boosting," Annals of Statistics, 2000; 28(2):337-374.

Frogoudaki et al., "Pacing for adult patients with left atrial isomerism: efficacy and technical considerations," Europace, Apr. 2003; 5(2):189-193.

Fung et al., Chapter 20, Optimization of Cardiac Resynchronization Therapy, Cardiac Resynchronization Therapy, Second Edition, Copyright 2008, Blackwell Publishing Ltd., pp. 356-373.

Ganapathy et al., "Implantable Device to Monitor Cardiac Activity with Sternal Wires," Pacing Clin. Electrophysiol., Dec. 2014; Epub Aug. 24, 2014; 37(12):1630-40.

Geddes, "Accuracy limitations of chronaxie values," IEEE Trans Biomed Eng., Jan. 2004; 51(1):176-81.

Gertz et al., "The impact of mitral regurgitation on patients undergoing catheter ablation of atrial fibrillation," Europace, Aug. 2011; 13(8):1127-32.

Ghosh et al. "Accuracy of Quadratic Versus Linear Interpolation in Noninvasive Electrocardiographic Imaging (ECGI)," Annuals of Biomedical Engineering, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" Circulation, 2008; 118:907-915. Published online Aug. 12, 2008.

Ghosh et al. "Application of L1-Norm Regularization to Epicardial Potential Solution of the Inverse Electrocardiography Problem," Annuals of Biomedical Engineering, vol. 37, No. 5, May 2009; pp. 902-912.

Ghosh et al., "Electrophysiological Substrate and Intraventricular LV Dyssynchrony in Non-ischemic Heart Failure Patients Undergoing Cardiac Resynchronization Therapy," Heart rhythm : the official journal of the Heart Rhythm Society, 2011; 8(5):692-699.

Girmatsion et al., "Changes in microRNA-1 expression and IK1 up-regulation in human atrial fibrillation," Heart Rhythm, Dec. 2009; 6(12):1802-9.

Goette et al., "Acute atrial tachyarrhythmia induces angiotensin II type 1 receptor-mediated oxidative stress and microvascular flow abnormalities in the ventricles," European Heart Journal, Jun. 2009; 30(11):1411-20.

Goette et al., "Electrophysiological effects of angiotensin II. Part I: signal transduction and basic electrophysiological mechanisms," Europace, Feb. 2008; 10(2):238-41.

Gold et al., "Comparison of Stimulation Sites within Left Ventricular Veins on the Acute Hemodynamic Effects of Cardiac Resynchronization Therapy" Heart Rhythm, Apr. 2005; 2(4):376-381.

Gómez et al., "Nitric oxide inhibits Kv4.3 and human cardiac transient outward potassium current (Itol)," Cardiovasc Res., Dec. 2008; 80(3):375-84.

Gros et al., "Connexin 30 is expressed in the mouse sino-atrial node and modulates heart rate," Cardiovascular Research, Jan. 2010; 85(1):45-55.

Guenther et al., "Substernal Lead Implantation: A Novel Option to Manage OFT Failure in S-ICD patients," Clinical Research Cardiology, Feb. 2015; Epub Oct. 2, 2014; 104(2):189-91.

Guillem et al., "Noninvasive mapping of human atrial fibrillation," J Cardiovasc Electrophysiol., May 2009; 20(5):507-513.

Gulrajani, "The Forward and Inverse Problems of Electrocardiography," IEEE Engineering in Medicine and Biology, IEEE Service Center, vol. 17, No. 5, Sep. 1, 1988; pp. 84-101, 122.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Hakacova et al., "Septal atrial pacing for the prevention of atrial fibrillation," Europace, 2007; 9:1124-1128.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hasan et al., "Safety, efficacy, and performance of implanted recycled cardiac rhythm management (CRM) devices in underprivileged patients," Pacing Clin Electrophysiol., Jun. 2011; 34(6):653-8.

Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

(56)  References Cited

OTHER PUBLICATIONS

Hayes et al., "Cardiac Resynchronization Therapy and the Relationship of Percent Biventricular Pacing to Symptoms and Survival," Heart Rhythm, Sep. 2011; 8(9):1469-1475.

He et al., "Three-dimensional cardiac electrical imaging from intracavity recordings," IEEE Trans Biomed Eng., Aug. 2007; 54(8):1454-60.

"Heart Failure Management" datasheet [online]. Medtronic, Minneapolis, Minnesota, [Last updated on Jun. 3, 2013]. Retrieved from the Internet: www.medtronic.com; 9 pages.

Heist et al., "Direct visualization of epicardial structures and ablation utilizing a visually guided laser balloon catheter: preliminary findings," J Cardiovasc Electrophysiol., Jul. 2011; 22(7):808-12.

Henz et al., "Synchronous Ventricular Pacing without Crossing the Tricuspid Valve or Entering the Coronary Sinus—Preliminary Results," J Cardiovasc Electrophysiol., Dec. 2009; 20(12):1391-1397.

Hiippala et al., "Automatic Atrial Threshold Measurement and Adjustment in Pediatric Patients," Pacing Clin Electrophysiol., Mar. 2010; 33(3):309-13.

Ho, "Letter to the Editor" J Cardiovasc Electrophysiol., Mar. 2010; 21(3): E76.

Höijer et al., "Improved cardiac function and quality of life following upgrade to dual chamber pacing after long-term ventricular stimulation," European Heart Journal, Mar. 2002; 23(6):490-497.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Huang et al., "A Novel Pacing Strategy With Low and Stable Output: Pacing the Left Bundle Branch Immediately Beyond the Conduction Block," Can J Cardiol., Dec. 2007; Epub Sep. 22, 2017; 33(12):1736.e1-1736.e.

Hurtado, "Electrical and Anatomical Modeling of the Specialized Cardiac Conduction System, A Simulation Study", Universitat Politecnica de Valenica, March 211, 96 pp.

Inter-Office Memo, Model 6426-85 Canine Feasibility AV Septal 8 mm Screw-In Right Single Pass DDD Lead Final Report (AR # 0120A0207).

Ishigaki et al., "Prevention of immediate recurrence of atrial fibrillation with low-dose landiolol after radiofrequency catheter ablation," Journal of Arrhythmia, Oct. 2015; 31(5):279-285.

Israel, "The role of pacing mode in the development of atrial fibrillation," Europace, Feb. 2006; 8(2):89-95.

Janion et al., "Dispersion of P wave duration and P wave vector in patients with atrial septal aneurysm," Europace, Jul. 2007; 9(7):471-4.

Jia et al., "Electrocardiographic Imaging of Cardiac Resynchronization Therapy in Heart Failure: Observation of Variable Electrophysiologic Responses," Heart Rhythm, vol. 3, No. 3; Mar. 1, 2006, pp. 296-310.

Kabra et al., "Recent Trends in Imaging for Atrial Fibrillation Ablation," Indian Pacing and Electrophysiology Journal, 2010; 10(5):215-227.

Kalbfleisch et al., "Catheter Ablation with Radiofrequency Energy: Biophysical Aspects and Clinical Applications," Journal of Cardiovascular Electrophysiology, Oct. 2008; 3(2):173-186.

Katritsis et al., "Classification and differential diagnosis of atrioventricular nodal re-entrant tachycardia," Europace, Jan. 2006; 8(1):29-36.

Katritsis et al., "Anatomically left-sided septal slow pathway ablation in dextrocardia and situs inversus totalis," Europace, Aug. 2008; 10(8):1004-5.

Kentta et al., "Prediction of sudden cardiac death with automated high-throughput analysis of heterogeneity in standard resting 12-lead electrocardiograms", Heart Rhythm Society, 2015, 8 pages.

Khairy et al., "Cardiac Arrhythmias In Congenital Heart Diseases," Indian Pacing and Electrophysiology Journal, Nov.-Dec. 2009; 9(6):299-317.

Kimmel et al., "Single-site ventricular and biventricular pacing: investigation of latest depolarization strategy," Europace, Dec. 2007; 9(12):1163-1170.

Knackstedt et al., "Electro-anatomic mapping systems in arrhythmias," Europace, Nov. 2008; 10 Suppl 3:iii28-iii34.

Kobayashi et al., "Successful Ablation of Antero-septal Accessory Pathway in the Non-Coronary Cusp in a Child," Indian Pacing and Electrophysiology Journal, 2012; 12(3):124-130.

Kojodjojo et al., "4:2:1 conduction of an AF initiating trigger," Indian Pacing and Electrophysiology Journal, Nov. 2015; 15(5):255-8.

Kołodzińska et al., "Differences in encapsulating lead tissue in patients who underwent transvenous lead removal," Europace, Jul. 2012; 14(7):994-1001.

Konecny et al., "Synchronous intra-myocardial ventricular pacing without crossing the tricuspid valve or entering the coronary sinus," Cardiovascular Revascularization Medicine, 2013; 14:137-138.

Kornreich, "Body Surface Potential Mapping of ST Segment Changes in Acute Myocardial Infarction," Circulation, 1993; 87: 773-782.

Kriatselis et al., "Ectopic atrial tachycardias with early activation at His site: radiofrequency ablation through a retrograde approach," Europace, Jun. 2008; 10(6):698-704.

Lalu et al., "Ischemia-reperfusion injury activates matrix metalloproteinases in the human heart," Eur Heart J., Jan. 2005; 26(1):27-35.

Laske et al., "Excitation of the Intrinsic Conduction System Through His and Interventricular Septal Pacing," Pacing Clin. Electrophysiol., Apr. 2006; 29(4):397-405.

Leclercq, "Problems and troubleshooting in regular follow-up of patients with cardiac resynchronization therapy," Europace, Nov. 2009; 11 Suppl 5:v66-71.

Lee et al., "An unusual atrial tachycardia in a patient with Friedreich ataxia," Europace, Nov. 2011; 13(11):1660-1.

Lee et al., "Blunted Proarrhythmic Effect of Nicorandil in a Langendorff-Perfused Phase-2 Myocardial Infarction Rabbit Model," Pacing Clin Electrophysiol., Feb. 2013; 36(2):142-51.

Lemay et al., "Spatial dynamics of atrial activity assessed by the vectorcardiogram: from sinus rhythm to atrial fibrillation," Europace, Nov. 2007; 9 Suppl 6:vi109-18.

Levy et al., "Does the mechanism of action of biatrial pacing for atrial fibrillation involve changes in cardiac haemodynamics? Assessment by Doppler echocardiography and natriuretic peptide measurements," Europace, Apr. 2000; 2(2):127-35.

Lewalter et al., "Comparison of spontaneous atrial fibrillation electrogram potentials to the P wave electrogram amplitude in dual chamber pacing with unipolar atrial sensing," Europace, Apr. 2000; 2(2):136-40.

Liakopoulos et al., "Sequential deformation and physiological considerations in unipolar right and left ventricular pacing," European Journal of Cardio-thoracic Surgery, Apr. 1, 2006; 29S1:S188-197.

Lian et al., "Computer modeling of ventricular rhythm during atrial fibrillation and ventricular pacing," IEEE Transactions on Biomedical Engineering, Aug. 2006; 53(8):1512-1520.

Lim et al., "Right ventricular lead implantation facilitated by a guiding sheath in a patient with severe chamber dilatation with tricuspid regurgitation," Indian Pacing and Electrophysiology Journal, Sep. 2011; 11(5):156-8.

Lim et al., "Coupled pacing improves left ventricular function during simulated atrial fibrillation without mechanical dyssynchrony," Europace, Mar. 2010; 12(3):430-6.

Liu et al., "Three-Dimensional Imaging of Ventricular Activation and Electrograms from Intercavitary Recordings", IEEE 2011, vol. 58, No. Apr. 2011, pp. 868-875.

Lou et al., "Tachy-brady arrhythmias: The critical role of adenosine-induced sinoatrial conduction block in post-tachycardia pauses," Heart Rhythm., Jan. 2013; 10(1):110-8.

Lumason™, Brochure, Bracco Diagnostocs. Oct. 2014.

Lutomsky et al., "Catheter ablation of paroxysmal atrial fibrillation improves cardiac function: a prospective study on the impact of atrial fibrillation ablation on left ventricular function assessed by magnetic resonance imaging," Europace, May 2008; 10(5):593-9.

(56) References Cited

OTHER PUBLICATIONS

Macedo et al, "Septal accessory pathway: anatomy, causes for difficulty, and an approach to ablation," Indian Pacing and Electrophysiology Journal, Jul. 2010; 10(7):292-309.

Mafi-Rad et al., "Feasibility and Acute Hemodynamic Effect of Left Ventricular Septal Pacing by Transvenous Approach Through the Interventricular Septum," Circ Arrhythm Electrophysoil., Mar. 2016; 9(3):e003344.

Mani et al., "Dual Atrioventricular Nodal Pathways Physiology: A Review of Relevant Anatomy, Electrophysiology, and Electrocardiographic Manifestations," Indian Pacing and Electrophysiology Journal, Jan. 2014; 14(1):12-25.

Manios et al., "Effects of successful cardioversion of persistent atrial fibrillation on right ventricular refractoriness and repolarization," Europace, Jan. 2005; 7(1):34-9.

Manolis et al., "Prevention of atrial fibrillation by inter-atrial septum pacing guided by electrophysiological testing, in patients with delayed interatrial conduction," Europace, Apr. 2002; 4(2):165-174.

Marino et al., "Inappropriate mode switching clarified by using a chest radiograph," Journal of Arrhythmia, Aug. 2015; 31(4):246-248.

Markowitz et al., "Time course and predictors of autonomic dysfunction after ablation of the slow atrioventricular nodal pathway," Pacing Clin Electrophysiol., Dec. 2004; 27(12):1638-43.

Marshall et al., "The effects of temperature on cardiac pacing thresholds," Pacing Clin Electrophysiol., Jul. 2010; 33(7):826-833.

McSharry et al., "A Dynamical Model for Generating Synthetic Electrocardiogram Signals," IEEE Transactions on Biomedical Engineering, Mar. 2003; 50(3):289-294.

Medtronic Vitatron Carelink Encore® Programmer Model 29901 Reference Manual, 2013, Medtronic, Inc., Minneapolis, MN.

Meijler et al., "Scaling of Atrioventricular Transmission in Mammalian Species: An Evolutionary Riddle!," Journal of Cfardiovascular Electrophysiology, Aug. 2002; 13(8):826-830.

Meiltz et al., "Permanent form of junctional reciprocating tachycardia in adults: peculiar features and results of radiofrequency catheter ablation," Europace, Jan. 2006; 8(1):21-8.

Mellin et al., "Transient reduction in myocardial free oxygen radical levels is involved in the improved cardiac function and structure after long-term allopurinol treatment initiated in established chronic heart failure," Eur Heart J., Aug. 2005; 26(15):1544-50.

Mestan et al., "The influence of fluid and diuretic administration on the index of atrial contribution in sequentially paced patients," Europace, Apr. 2006; 8(4):273-8.

Metin et al., "Assessment of the P Wave Dispersion and Duration in Elite Women Basketball Players," Indian Pacing and Electrophysiology Journal, 2010; 10(1):11-20.

Mills et al., "Left Ventricular Septal and Left Ventricular Apical Pacing Chronically Maintain Cardiac Contractile Coordination, Pump Function and Efficiency," Circ Arrhythm Electrophysoil., Oct. 2009; 2(5):571-579.

Mirzoyev et al., "Embryology of the Conduction System for the Electrophysiologist," Indian Pacing and Electrophysiology Journal, 2010; 10(8):329-338.

Miri et al., "Applicability of body surface potential map in computerized optimization of biventricular pacing," Annals of Biomedical Engineering, vol. 38, No. 3, Mar. 2010, pp. 865-875.

Miri et al., "Comparison of the electrophysiologically based optimization methods with different pacing parameters in patient undergoing resynchronization treatment," 30th Annual International IEEE EMBS Conference, Aug. 2008, pp. 1741-1744.

Miri et al., "Computerized Optimization of Biventricular Pacing Using Body Surface Potential Map," 31st Annual International Conference of the IEEE EMBS, Sep. 2009, pp. 2815-2818.

Miri et al., "Efficiency of Timing Delays and Electrode Positions in Optimization of Biventricular Pacing: A Simulation Study," IEEE Transactions on Biomedical Engineering, Nov. 2009, pp. 2573-2582.

Mitchell et al., "How do atrial pacing algorithms prevent atrial arrhythmias?" Europace, Jul. 2004; 6(4):351-62.

Modre et al., "Noninvasive Myocardial Activation Time Imaging: A Novel Inverse Algorithm Applied to Clinical ECG Mapping Data," IEE Transactions on Biomedical Engineering, Oct. 2002; 49(10):1153-1161.

Montgomery et al., "Measurement of diffuse ventricular fibrosis with myocardial T1 in patients with atrial fibrillation," J Arrhythm., Feb. 2016; 32(1):51-6.

Mulpuru et al., "Synchronous ventricular pacing with direct capture of the atrioventricular conduction system: Functional anatomy, terminology, and challenges," Heart Rhythm, Nov. 2016; Epub Aug. 3, 2016; 13(11):2237-2246.

Musa et al., "Inhibition of Platelet-Derived Growth Factor-AB Signaling Prevents Electromechanical Remodeling of Adult Atrial Myocytes that Contact Myofibroblasts," Heart Rhythm, Jul. 2013; 10(7):1044-1051.

Nagy et al., "Wnt-11 signalling controls ventricular myocardium development by patterning N-cadherin and β-catenin expression," Cardiovascular Research, Jan. 2010; 85(1):100-9.

Peschar et al., "Left Ventricular Septal and Apex Pacing for Optimal Pump Function in Canine Hearts," J Am Coll Cardiol., Apr. 2, 2003; 41(7):1218-1226.

Physiological Research Laboratories, Final Report for an Acute Study for Model 6426-85 AV Septal Leads, Feb. 1996.

Porciani et al., "Interatrial septum pacing avoids the adverse effect of interatrial delay in biventricular pacing: an echo-Doppler evaluation," Europace, Jul. 2002; 4(3):317-324.

Potse et al., "A Comparison of Monodomain and Bidomain Reaction-Diffusion Models for Action Potential Propagation in the Human Heart," IEEE Transactions on Biomedical Engineering, Dec. 2006; 53(12 Pt 1):2425-35.

Potse et al., "Mathematical Modeling and Simulation of Ventricular Activation Sequences: Implications for Cardiac Resynchronization Therapy," J. of Cardiovasc. Trans. Res., 2012; 5:146-158.

Prinzen et al., "Cardiac Resynchronization Therapy State-of-the-Art of Current Applications, Guidelines, Ongoing Trials, and Areas of Controversy" Circulation, 2013; 128: 2407-2418.

Prystowsky et al., "Case studies with the experts: management decisions in atrial fibrillation," J Cardiovasc Electrophysiol., Feb. 2008; 19(Suppl. 1):S1-12.

Prystowsky, "The history of atrial fibrillation: the last 100 years," J Cardiovasc Electrophysiol, Jun. 2008; 19(6):575-582.

Pytkowski et al., "Paroxysmal atrial fibrillation is associated with increased intra-atrial conduction delay," Europace, Dec. 2008; 10(12):1415-20.

Qu et al., "Dynamics and cardiac arrhythmias," J Cardiovasc Electrophysiol., Sep. 2006; 17(9):1042-9.

Ravens et al., "Role of potassium currents in cardiac arrhythmias," Europace, Oct. 2008; 10(10):1133-7.

Ricci et al., Efficacy of a dual chamber defibrillator with atrial antitachycardia functions in treating spontaneous atrial tachyarrhythmias in patients with life-threatening ventricular tachyarrhythmias, European Heart Journal, Sep. 2002; 23(18):1471-9.

Ridgeway, "The State of Boosting," Computing Science and Statistics, 1999; 31:172-181.

Roberts-Thomson et al., "Focal atrial tachycardia II: management," Pacing Clin Electrophysiol., Jul. 2006; 29(7):769-78.

Rossi et al., "Endocardial vagal atrioventricular node stimulation in humans: reproducibility on 18-month follow-up," Europace, Dec. 2010; 12(12):1719-24.

Rouzet et al., "Contraction delay of the RV outflow tract in patients with Brugada syndrome is dependent on the spontaneous ST-segment elevation pattern," Heart Rhythm, Dec. 2011; 8(12):1905-12.

Russo et al., "Atrial Fibrillation and Beta Thalassemia Major: The Predictive Role of the 12-lead Electrocardiogram Analysis," Indian Pacing and Electrophysiology Journal, May 2014; 14(3):121-32.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.

Sairaku et al., "Prediction of sinus node dysfunction in patients with persistent atrial flutter using the flutter cycle length," Europace, Mar. 2012; 14(3):380-7.

(56)　　　　　References Cited

OTHER PUBLICATIONS

Santini et al., "Immediate and long-term atrial sensing stability in single-lead VDD pacing depends on right atrial dimensions," Europace, Oct. 2001; 3(4):324-31.

Saremi et al., "Cardiac Conduction System: Delineation of Anatomic Landmarks With Multidetector CT," Indian Pacing and Electrophysiology Journal, Nov. 2009; 9(6):318-33.

Savelieva et al., "Anti-arrhythmic drug therapy for atrial fibrillation: current anti-arrhythmic drugs, investigational agents, and innovative approaches," Europace, Jun. 2008; 10(6):647-665.

Schmidt et al., "Navigated DENSE strain imaging for post-radiofrequency ablation lesion assessment in the swine left atria," Europace, Jan. 2014; 16(1):133-41.

Schoonderwoerd et al., "Rapid Pacing Results in Changes in Atrial but not in Ventricular Refractoriness," Pacing Clin Electrophysiol., Mar. 2002; 25(3):287-90.

Schoonderwoerd et al., "Atrial natriuretic peptides during experimental atrial tachycardia: role of developing tachycardiomyopathy," J Cardiovasc Electrophysiol., Aug. 2004; 15(8):927-32.

Schoonderwoerd et al., "Atrial ultrastructural changes during experimental atrial tachycardia depend on high ventricular rate," J Cardiovasc Electrophysiol., Oct. 2004; 15(10):1167-74.

Sedmera, "Function and form in the developing cardiovascular system," Cardiovasc Res., Jul. 2011; 91(2):252-9.

Severi et al., "Alterations of atrial electrophysiology induced by electrolyte variations: combined computational and P-wave analysis," Europace, Jun. 2010; 12(6):842-9.

Seyedi et al., "A Survey on Intrabody Communications for Body Area Network Application," IEEE Transactions on Biomedical Engineering, vol. 60(8): 2067-2079, 2013.

Shah et al., "Stable atrial sensing on long-term follow up of VDD pacemakers," Indian Pacing and Electrophysiology Journal, Oct. 2006; 6(4):189-93.

Shenthar et al., "Permanent pacemaker implantation in a patient with situs solitus, dextrocardia, and corrected transposition of the great arteries using a novel angiographic technique," Journal of Arrhythmia, Apr. 2014; 30(2):134-138.

Shenthar et al., "Transvenous permanent pacemaker implantation in dextrocardia: technique, challenges, outcome, and a brief review of literature," Europace, Sep. 2014; 16(9):1327-33.

Shirayama, "Role of atrial fibrillation threshold evaluation on guiding treatment," Indian Pacing and Electrophysiology Journal, Oct. 2003; 3(4):224-230.

Silva et al., "Cardiac Resynchronization Therapy in Pediatric Congenital Heart Disease: Insights from Noninvasive Electrocardiographic Imaging" Heart Rhythm, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," Circulation, 2011; 123:1159-1166.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.

Spickler et al., "Totally Self-Contained Intracardiac Pacemaker," Journal of Electrocardiology, vol. 3(3&4): 324-331, 1970.

Sreeram et al., "Indications for Electrophysiology Study in children," Indian Pacing and Electrophysiology Journal, Apr.-Jun. 2008; 8(Suppl. 1):S36-S54.

Steinhaus BM., "Estimating cardiac transmembrane activation and recovery times from unipolar and bipolar extracellular electrograms: a simulation study," Circulation Research, 1989, 64:449-462.

Stockburger et al., "Optimization of cardiac resynchronization guided by Doppler echocardiography: haemodynamic improvement and intraindividual variability with different pacing configurations and atrioventricular delays," Europace, Oct. 2006; 8(10):881-6.

Strik et al., "Electrical and Mechanical Ventricular Activation During Left Bundle Branch Block and Resynchronization," J. of Cardiovasc. Trans. Res., 2012; 5:117-126.

Stroobandt et al., "Prediction of Wenckebach Behavior and Block Response in DDD Pacemakers," Pacing Clin Electrophysiol., Jun. 2006; 9(6):1040-6.

Suenari et al., "Idiopathic left ventricular tachycardia with dual electrocardiogram morphologies in a single patient," Europace, Apr. 2010; 12(4):592-4.

Svendsen et al., "Computational Models of Cardiac Electrical Activation," Chapter 5, Computational Nov. 2010, pp. 73-88.

Sweeney et al., "Analysis of Ventricular Activation Using Surface Electrocardiography Predict Left Ventricular Reverse Volumetric Remodeling During Cardiac Resynchronization Therapy," Circulation, Feb. 9, 2010, 121(5): 626-34.

Sweeney et al., QRS Fusion Complex Analysis Using Wave Interference to Predict Reverse Remodeling During Cardiac Resynchronization Therapy, heart Rhythm, 2014, 11:806-813.

Tan et al., "Interlead heterogencit of R- and T-wave morphology in standard 12-lead ECGs predicts sustained ventricular tachycardia/fibrillation and arrhythmic death in patients with cardiomyopathy", J. Cardiovasc Electrophysiol. 2017, 28, pp. 1324-1333.

Tan et al., "Electrocardiographic evidence of ventricular repolarization remodelling during atrial fibrillation," Europace, Jan. 2008; 10(1):99-104.

Taramasco et al., "Internal low-energy cardioversion: a therapeutic option for restoring sinus rhythm in chronic atrial fibrillation after failure of external cardioversion," Europace, Jul. 1999; 1(3):179-82.

Testa et al., "Rate-control or rhythm-control: where do we stand?" Indian Pacing and Electrophysiology Journal, Oct. 2005; 5(4):296-304.

Thejus et al., "N-terminal Pro-Brain Natriuretic Peptide And Atrial Fibrillation," Indian Pacing and Electrophysiology Journal, Jan. 2009; 9(1):1-4.

Thornton et al., "Magnetic Assisted Navigation in Electrophysiology and Cardiac Resynchronisation: A Review," Indian Pacing and Electrophysiology Journal, Oct. 2006; 6(4):202-13.

Tilz et al., "In vivo left-ventricular contact force analysis: comparison of antegrade transseptal with retrograde transaortic mapping strategies and correlation of impedance and electrical amplitude with contact force," Europace, Sep. 2014; 16(9):1387-95.

Tomaske et al., "Do daily threshold trend fluctuations of epicardial leads correlate with pacing and sensing characteristics in paediatric patients?" Europace, Aug. 2007; 9(8):662-668.

Tomioka et al., "The effect of ventricular sequential contraction on helical heart during pacing: high septal pacing versus biventricular pacing," European Journal of Cardio-thoracic Surgery, Apr. 1, 2006; 29S1:S198-206.

Tournoux et al., "A 'Regularly Irregular' tachycardia: What is the diagnosis?" Europace, Dec. 2008; 10(12):1445-6.

Traykov et al., "Electrogram analysis at the His bundle region and the proximal coronary sinus as a tool to predict left atrial origin of focal atrial tachycardias," Europace, Jul. 2011; 13(7):1022-7.

Trudel et al., "Simulation of QRST integral maps with a membrane-based computer heart model employing parallel processing," IEEE Trans Biomed Eng., Aug. 2004; 51(8):1319-29.

Tse et al., "Cardiac dynamics: Alternans and arrhythmogenesis," Journal of Arrhythmia, Oct. 2016; 32(5):411-417.

Tse, "Mechanisms of cardiac arrhythmias," Journal of Arrhythmia, Apr. 2016; 32(2):75-81.

Turner et al., "Electrical and Mechanical Components of Dyssynchrony in Heart Failure Patients with Normal QRS Duration and Left Bundle-Branch Block," Circulation 2004; 109: 2544-2549.

Ueda et al., "Outcomes of single- or dual-chamber implantable cardioverter defibrillator systems in Japanese patients," Journal of Arrhythmia, Apr. 2016; 32(2):89-94.

Van Dam et al., "Volume conductor effects involved in the genesis of the P wave," Europace, Sep. 2005; 7 Suppl 2:30-8.

Van den Berg et al., "Depletion of atrial natriuretic peptide during longstanding atrial fibrillation," Europace, Sep. 2004; 6(5):433-7.

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.

(56)         References Cited

OTHER PUBLICATIONS

Van Opstal et al., "Paradoxical increase of stimulus to atrium interval despite His-bundle capture during para-Hisian pacing," Europace, Dec. 2009; 11(12):1702-4.

Vardas et al., The Task Force for Cardiac Pacing and Cardiac Resynchronization Therapy of the European Society of Cardiology. Developed in Collaboration with the European Heart Rhythm Association, European Heart Journal, 2007; 28:2256-2295.

Varma et al., "Placebo CRT," Journal of Cardiovascular Electrophysiology, vol. 19, Aug. 2008; p. 878.

Namboodiri et al., "Electrophysiological features of atrial flutter in cardiac sarcoidosis: a report of two cases," Indian Pacing and Electrophysiology Journal, Nov. 2012; 12(6):284-9.

Nanthakumar et al., "Assessment of accessory pathway and atrial refractoriness by transesophageal and intracardiac atrial stimulation: An analysis of methodological agreement," Europace, Jan. 1999; 1(1):55-62.

Nash et al., "An Experimental-Computational Framework for Validating in-vivo ECG Inverse Algorithms," International Journal of Bioelectromagnetism, vol. 2, No. 2, Dec. 31, 2000, 9 pp.

Neto et al., "Temporary atrial pacing in the prevention of postoperative atrial fibrillation," Pacing Clin Electrophysiol., Jan. 2007; 30(Suppl 1):S79-83.

Nishijima et al., "Tetrahydrobiopterin depletion and NOS2 uncoupling contribute to heart failure-induced alterations in atrial electrophysiology," Cardiovasc Res., Jul. 2011; 91(1):71-9.

Niwano et al., "Effect of oral L-type calcium channel blocker on repetitive paroxysmal atrial fibrillation: spectral analysis of fibrillation waves in the Holter monitoring," Europace, Dec. 2007; 9(12):1209-1215.

Okumura et al., "Effects of a high-fat diet on the electrical properties of porcine atria," Journal of Arrhythmia, Dec. 2015; 31(6):352-358.

Olesen et al., "Mutations in sodium channel β-subunit SCN3B are associated with early-onset lone atrial fibrillation," Cardiovascular Research, Mar. 2011; 89(4):786-93.

Ozmen et al., "P wave dispersion is increased in pulmonary stenosis," Indian Pacing and Electrophysiology Journal, Jan. 2006; 6(1):25-30.

Packer et al., "New generation of electro-anatomic mapping: Full intracardiac image integration," Europace, Nov. 2008; 10 Suppl 3:iii35-41.

Page et al., "Ischemic ventricular tachycardia presenting as a narrow complex tachycardia," Indian Pacing and Electrophysiology Journal, Jul. 2014; 14(4):203-210.

Pakarinen et al., "Pre-implant determinants of adequate long-term function of single lead VDD pacemakers," Europace, Apr. 2002; 4:137-141.

Patel et al., "Atrial Fibrillation after Cardiac Surgery: Where are we now?" Indian Pacing and Electrophysiology Journal, Oct.-Dec. 2008; 8(4):281-291.

Patel et al., "Successful ablation of a left-sided accessory pathway in a patient with coronary sinus atresia and arteriovenous fistula: clinical and developmental insights," Indian Pacing and Electrophysiology Journal, Mar. 2011; 11(2):43-49.

Veenhuyzen et al., "Diagnostic pacing maneuvers for supraventricular tachycardia: part 1," Pacing Clin Electrophysiol., Jun. 2011; 34(6):767-82.

Veenhuyzen et al., "Diagnostic pacing maneuvers for supraventricular tachycardias: part 2," Pacing Clin Electrophysiol., Jun. 2012; 35(6):757-69.

Veenhuyzen et al., "Principles of Entrainment: Diagnostic Utility for Supraventricular Tachycardia," Indian Pacing and Electrophysiology Journal, 2008; 8(1):51-65.

Verbrugge et al., "Revisiting diastolic filling time as mechanistic insight for response to cardiac resynchronization therapy," Europace, Dec. 2013; 15(12):1747-56.

Verrier et al., "Mechanisms of ranolazine's dual protection against atrial and ventricular fibrillation," Europace, Mar. 2013; 15(3):317-324.

Verrijcken et al., "Pacemaker-mediated tachycardia with varying cycle length: what is the mechanism?" Europace, Oct. 2009; 11(10):1400-2.

Villani et al., "Reproducibility of internal atrial defibrillation threshold in paroxysmal and persistent atrial fibrillation," Europace, Jul. 2004; 6(4):267-72.

Violi et al., "Antioxidants for prevention of atrial fibrillation: a potentially useful future therapeutic approach? A review of the literature and meta-analysis," Europace, Aug. 2014; 16(8):1107-1116.

Wang et al., "Application of the Method of Fundamental Solutions to Potential-based Inverse Electrocardiography," Annals of Biomedical Engineering, Aug. 2006, pp. 1272-1288.

Weber et al., "Adenosine sensitive focal atrial tachycardia originating from the non-coronary aortic cusp," Europace, Jun. 2009; 11(6):823-6.

Weber et al., "Open-irrigated laser catheter ablation: relationship between the level of energy, myocardial thickness, and collateral damages in a dog model," Europace, Jan. 2014; 16(1):142-8.

Wegmoller, "Intra-Body Communication for Biomedical Sensor Networks," Diss. ETH, No. 17323, 1-173, 2007.

Wei et al., "Comparative simulation of excitation and body surface electrocardiogram with isotropic and anisotropic computer heart models," IEEE Trans Biomed Eng., Apr. 1995; 42(4):343-57.

Weijs et al., "Clinical and echocardiographic correlates of intra-atrial conduction delay," Europace, Dec. 2011; 13(12):1681-7.

Weiss et al., "The influence of fibre orientation, extracted from different segments of the human left ventricle, on the activation and repolarization sequence: a simulation study," Europace, Nov. 2007; 9(Suppl. 6):vi96-vi104.

Wellens, MD et al., "The Electrocardiogram 102 Years After Einthoven," Circulation, Feb. 2004; vol. 109, No. 5, pp. 562-564.

Wetzel et al., "A stepwise mapping approach for localization and ablation of ectopic right, left, and septal atrial foci using electroanatomic mapping," European Heart Journal, Sep. 2002; 23(17):1387-1393.

Williams et al., "Short-Term Hemodynamic Effects of Cardiac Resynchronization Therapy in Patients With Heart Failure, a Narrow QRS Duration, and No Dyssynchrony," Circulation, Oct. 27, 2009; 120: 1687-1694.

Wlodarska et al., "Thromboembolic complications in patients with arrhythmogenic right ventricular dysplasia/cardiomyopathy," Europace, Aug. 2006; 8(8):596-600.

Wong et al., "A review of mitral isthmus ablation," Indian Pacing and Electrophysiology Journal, 2012; 12(4):152-170.

Wu et al., "Acute and long-term outcome after catheter ablation of supraventricular tachycardia in patients after the Mustard or Senning operation for D-transposition of the great arteries," Europace, Jun. 2013; 15(6):886-91.

Xia et al., "Asymmetric dimethylarginine concentration and early recurrence of atrial fibrillation after electrical cardioversion," Pacing Clin Electrophysiol., Aug. 2008; 31(8):1036-40.

Yamazaki et al., "Acute Regional Left Atrial Ischemia Causes Acceleration of Atrial Drivers during Atrial Fibrillation," Heart Rhythm, Jun. 2013; 10(6):901-9.

Yang et al., "Focal atrial tachycardia originating from the distal portion of the left atrial appendage: Characteristics and long-term outcomes of radiofrequency ablation," Europace, Feb. 2012; 14(2):254-60.

Yiginer et al., "Advanced Age, Female Gender and Delay in Pacemaker Implantation May Cause TdP in Patients With Complete Atrioventricular Block," Indian Pacing and Electrophysiology Journal, Oct. 2010; 10(10):454-63.

Yoon et al., "Measurement of thoracic current flow in pigs for the study of defibrillation and cardioversion," IEEE Transactions on Biomedical Engineering, Oct. 2003; 50(10):1167-1773.

Yuan et al., "Recording monophasic action potentials using a platinum-electrode ablation catheter," Europace, Oct. 2000; 2(4):312-9.

Yusuf et al., "5-Hydroxytryptamine and Atrial Fibrillation: How Significant is This Piece in the Puzzle?" J Cardiovasc Electrophysiol., Feb. 2003; 14(2):209-14.

Zaugg et al., "Current concepts on ventricular fibrillation: a vicious circle of cardiomyocyte calcium overload in the initiation, mainte-

(56) References Cited

OTHER PUBLICATIONS nance, and termination of ventricular fibrillation," Indian Pacing and Electrophysiology Journal, Apr. 2004; 4(2):85-92.

Zhang et al., "Acute atrial arrhythmogenicity and altered Ca(2+) homeostasis in murine RyR2-P2328S hearts," Cardiovascular Research, Mar. 2011; 89(4):794-804.

Zoghi et al., "Electrical stunning and hibernation: suggestion of new terms for short- and long-term cardiac memory," Europace, Sep. 2004; 6(5):418-24.

Zografos et al., "Inhibition of the renin-angiotensin system for prevention of atrial fibrillation," Pacing Clin Electrophysiol., Oct. 2010; 33(10):1270-85.

(PCT/US2014/066792) PCT Notification of Transmittal of the International Search Report and the Written Opinion of the International Searching Authority.

(PCT/US2014/013601) PCT Notification of Transmittal of the International Search Report and the Written Opinion of the International Searching Authority.

International Search Report and Written Opinion issued May 3, 2012 for International Application No. PCT/US2012/036262; 9 pages.

International Search Report and Written Opinion issued May 3, 2012 for International Application No. PCT/US2012/036302; 9 pages.

International Search Report and Written Opinion issued Sep. 3, 2012 for International Application No. PCT/US2012/036262 9 pages.

International Search Report and Written Opinion issued Aug. 6, 2014 for International Application No. PCT/US2014/036153; 14 pages.

(PCT/US2014/036782) PCT Notification of Transmittal of the International Search Report and the Written Opinion of the International Searching Authority, Mailed Aug. 22, 2014, 11 pages.

International Search Report and Written Opinion issued Nov. 7, 2014 for International Application No. PCT/US2014/036163; 12 pages.

International Search Report and Written Opinion issued Oct. 24, 2014 for International Application No. PCT/US2014/041929; 14 pages.

International Search Report and Written Opinion issued Oct. 28, 2014 for International Application No. PCT/US2014/041928; 15 pages.

International Search Report and Written Opinion issued on Nov. 4, 2014 for International Application No. PCT/US2014/0247583; 7 pages.

International Search Report and Written Opinion issued on Nov. 12, 2014 for International Application No. PCT/US2014/047971; 7 pages.

International Search Report and Written Opinion issued on Nov. 12, 2014 for International Application No. PCT/US2014/048120; 7 pages.

International Search Report and Written Opinion issued on Mar. 9, 2015 for International Application No. PCT/US2014/069214; 11 pages.

International Search Report and Written Opinion issued on Mar. 16, 2015 for International Application No. PCT/US2014/069182; 11 pages.

International Search Report and Written Opinion issued Mar. 16, 2015 for International Application No. PCT/US2014/069182; 11 pages.

International Search Report and Written Opinion issued on Mar. 17, 2015, for International Application No. PCT/US2014/069192; 11 pages.

International Search Report and Written Opinion issued Mar. 17, 2015 for International Application No. PCT/US2014/069192; 11 pages.

International Search Report and Written Opinion issued on Apr. 8, 2015 for International Application No. PCT/US2014/069070; 11 pages.

International Search Report and Written Opinion issued on Jun. 11, 2015 for International Application No. PCT/US2015/021442; 13 pages.

International Search Report and Written Opinion issued May 27, 2019 for International Application No. PCT/US2019/023549; 15 pages.

International Search Report and Written Opinion for Application No. PCT/US2017/047378, 8 pages, date mailed Dec. 6, 2017.

(PCT Notification of Transmittal of the International Search Report and the Written Opinion of the International Searching Authority, Mailed Nov. 14, 2018 from PCT/US2018/050988) , 11 pages.

(PCT/US2018/050993) PCT Notification of Transmittal of the International Search Report and the Written Opinion of the International Searching Authority, mailed Nov. 16, 2018, 7 pages.

(PCT/US2019/023642) PCT Notification of Transmittal of the International Search Report and the Written Opinion of the International Searching Authority, mailed Jun. 28, 2019, 14 pages.

(PCT/US2019/023645) PCT Notification of Transmittal of the International Search Report and the Written Opinion of the International Searching Authority, mailed Sep. 4, 2019, 14 pages.

(PCT/US2019/023646) PCT Notification of Transmittal of the International Search Report and the Written Opinion of the International Searching Authority, mailed Aug. 19, 2019, 15 pages.

(PCT/IB2019/057352) PCT Notification of Transmittal of the International Search Report and the Written Opinion of the International Searching Authority, mailed Nov. 27, 2019, 123 pages.

International Search Report and Written Opinion dated Apr. 2, 2020 from PCT Application No. PCT/2019/067858, 14 pages.

International Search Report and Written Opinion for PCT Application No. PCT/US2020/019200 dated May 29, 2020, 9 pages.

International Search Report and Written Opinion issued Jun. 4, 2020 for International Application No. PCT/US2020/019589; 11 pages.

International Search Report and Written Opinion for Application No. PCT/US2020/023525, 10 pages, date mailed Jul. 9, 2020.

International Search Report and Written Opinion for Application No. PCT/US2020/047802, 9 pages, date mailed Nov. 19, 2020.

International Search Report and Written Opinion from PCT Application No. PCT/US2020/053472 dated Jan. 12, 2021, 8 pages.

International Search Report and Written Opinion from PCT Application No. PCT/US2020/053474 dated Jan. 13, 2021, 8 pages.

International Search Report and Written Opinion from PCT Application No. PCT/US2020/062466, dated Jan. 27, 2021, 15 pages.

International Search Report and Written Opinion from PCT Application No. PCT/US2020/058627 dated Jan. 28, 2021, 9 pages.

International Search Report and Written Opinion from PCT Application No. PCT/US2021/015226, dated Apr. 9, 2021, 14 pages.

International Search Report and Written Opinion from PCT Application No. PCT/US2021/033046, dated Aug. 9, 2021, 16 pages.

* cited by examiner

500

510 — Monitor Electrical Activity

520 — Filter Each Electrical Signal

530 — Detect QRS Peak Based on Filtered Signals

540 — Determine Threshold Function Based on QRS peak

550 — Detect subsequent QRS Complex Based on Threshold Function

800

810 — Monitor Electrical Activity

820 — Filter Each Electrical Signal Using a First Filter and a Second Filter

830 — Detect QRS Peak Based on the First and Second Filtered Signals

840 — Generate a Dispersion Signal

850 — Determine a First Derivative Based on the Dispersion Signal

860 — Determine an Onset and an Offset

QRS DETECTION AND BRACKETING

The present application claims the benefit of U.S. Provisional Application No. 63/028,293, filed May 21, 2020 and U.S. Provisional Application No. 63/034,397, filed Jun. 3, 2020, which are incorporated herein by reference in their entireties.

The disclosure herein relates to systems and methods for use in the detecting and bracketing of QRS complexes in cardiac signals monitored by a plurality of external electrodes.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via electrodes on the surface, or skin, of the patient. More specifically, the patient may have a plurality of electrodes on an ECG belt or vest that surrounds the torso of the patient. After the belt or vest has been secured to the torso, a physician can perform a series of tests to evaluate a patient's cardiac response. The evaluation process can include detection of a baseline rhythm in which no electrical stimuli is delivered to cardiac tissue and another rhythm after electrical stimuli is delivered to the cardiac tissue.

The ECG electrodes placed on the body surface of the patient may be used for various therapeutic purposes (e.g., cardiac resynchronization therapy) including optimizing lead location, pacing parameters, etc. based on one or more metrics derived from the signals captured by the ECG electrodes. For example, electrical heterogeneity information may be derived from electrical activation times computed from multiple electrodes on the body surface.

Further, the signals from multiple electrodes on the body surface can be used to determine one or more specific ECG features such as, e.g., QRS onset, peak, QRS offset, etc. for a series of multiple heartbeats. Such ECG features may be used by themselves to evaluate cardiac health and/or therapy, or may be used to calculate, or compute, activation times.

SUMMARY

The exemplary systems and methods described herein may be configured to assist users (e.g., physicians) in configuring cardiac therapy (e.g., cardiac therapy being performed on a patient during and/or after implantation of cardiac therapy apparatus). The systems and methods may be described as being noninvasive. For example, the systems and methods may not need implantable devices such as leads, probes, sensors, catheters, etc. to evaluate and configure the cardiac therapy. Instead, the systems and methods may use electrical measurements taken noninvasively using, e.g., a plurality of external electrodes attached to the skin of a patient about the patient's torso.

One exemplary system for use in cardiac evaluation may include an electrode apparatus comprising a plurality of external electrodes to be disposed proximate a patient's skin. A computing apparatus comprises processing circuitry. The computing apparatus is operably coupled to the electrode apparatus. The computing apparatus is configured to monitor electrical activity from tissue of a patient using a plurality of external electrodes to generate a plurality of electrical signals over time. The plurality of electrical signals are filtered using a first filter having a first frequency range to generate a plurality of first filtered signals. The plurality of electrical signals are filtered using a second filter having a second frequency range different than the first frequency range to generate a plurality of second filtered signals. At least one QRS complex is detected based on the plurality of first filtered signals. A QRS peak of the at least one QRS complex is detected based on the plurality of second filtered signals and the detected at least one QRS complex.

One exemplary method for use in cardiac evaluation may include monitoring electrical activity from tissue of a patient using a plurality of external electrodes to generate a plurality of electrical signals over time. The plurality of electrical signals are filtered using a first filter having a first frequency range to generate a plurality of first filtered signals. The plurality of electrical signals are filtered using a second filter having a second frequency range different than the first frequency range to generate a plurality of second filtered signals. At least one QRS complex is detected based on the plurality of first filtered signals. A QRS peak of the at least one QRS complex is detected based on the plurality of second filtered signals and the detected at least one QRS complex.

An exemplary system for use in cardiac evaluation may include an electrode apparatus comprising a plurality of external electrodes to be disposed proximate a patient's skin. A computing apparatus comprises processing circuitry. The computing apparatus is operably coupled to the electrode apparatus. The computing apparatus is configured to monitor electrical activity from tissue of a patient using a plurality of external electrodes to generate a plurality of electrical signals over time. The plurality of electrical signals are filtered using at least one filter to generate a plurality of filtered signals. A QRS peak is detected based on the plurality of filtered signals. A threshold function is determined based on the QRS peak. The threshold function is configured to provide sensitivity for detecting at least one subsequent QRS complex. The at least one QRS complex is detected based on the threshold function.

An exemplary method for use in cardiac evaluation may include monitoring electrical activity from tissue of a patient using a plurality of external electrodes to generate a plurality of electrical signals over time. The plurality of electrical signals are filtered using at least one filter to generate a plurality of filtered signals. A QRS peak is detected based on the plurality of filtered signals. A threshold function is determined based on the QRS peak. The threshold function is configured to provide sensitivity for detecting at least one subsequent QRS complex. The at least one QRS complex is detected based on the threshold function.

An exemplary system for use in cardiac evaluation may include an electrode apparatus comprising a plurality of external electrodes to be disposed proximate a patient's skin. A computing apparatus comprises processing circuitry. The computing apparatus is operably coupled to the electrode apparatus. The computing apparatus is configured to monitor electrical activity from tissue of a patient using a plurality of external electrodes to generate a plurality of electrical signals over time. The plurality of electrical signals are filtered using a first filter and a second filter to generate a plurality of first filtered signals and a plurality of second filtered signals. The first filter and the second filter have different frequency ranges. A QRS peak is detected based on the plurality of first and second filtered signals. A dispersion signal is generated from the plurality of second filtered signals. The dispersion signal is representative of the dispersion of the plurality of second filtered signals over time. A first derivative signal is determined based on the dispersion signal. A QRS onset time value and a QRS offset time value corresponding to the at least one QRS complex is determined based on the first derivative signal.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
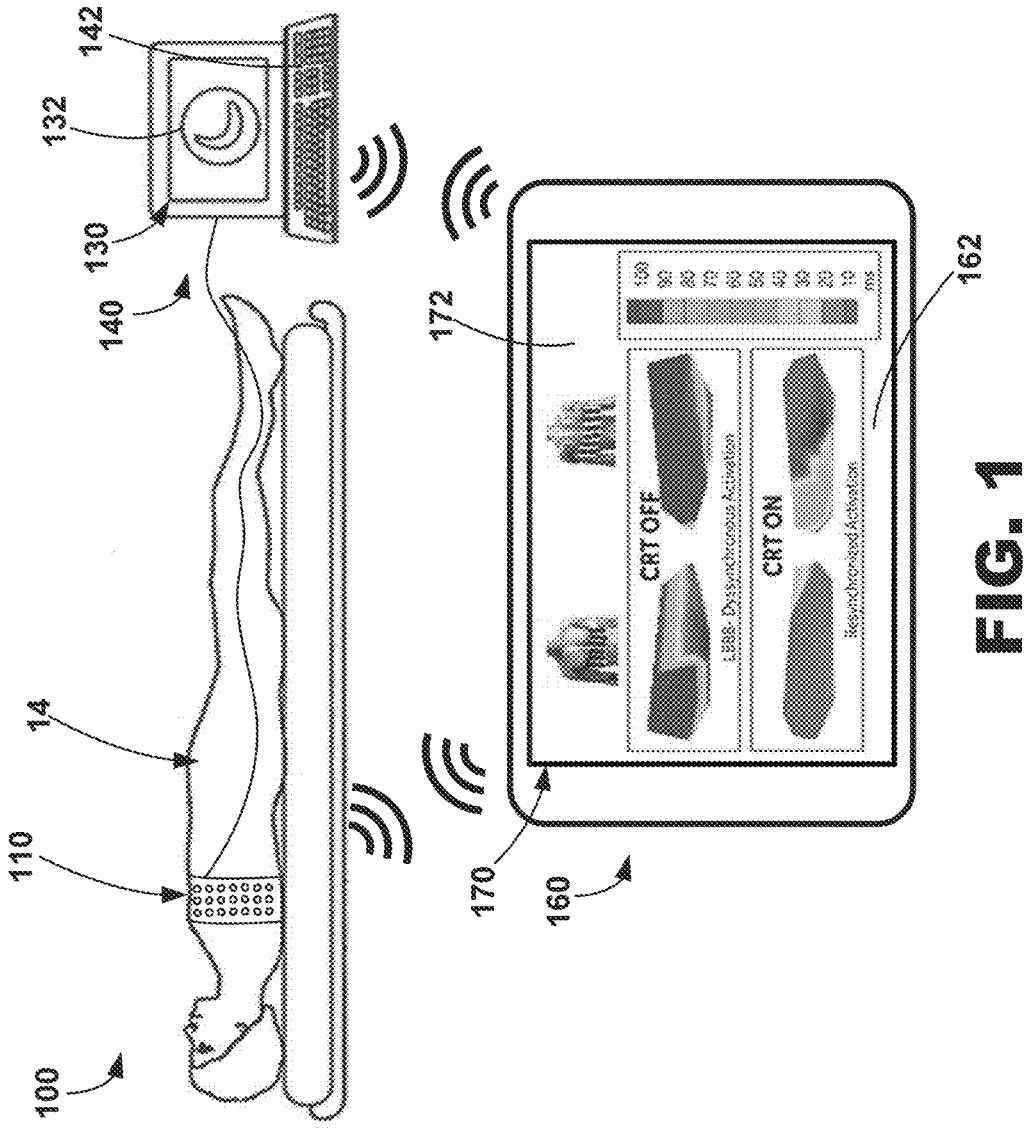
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Illustrative systems and methods shall be described with reference to FIGS. 1-13. It will be apparent to one skilled in the art that elements or processes from one embodiment may be used in combination with elements or processes of the other embodiments, and that the possible embodiments of such systems, methods, and devices using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) signals (e.g., torso-surface potentials) may be measured, or monitored, using a plurality of external electrodes positioned about the surface, or skin, of a patient. The ECG signals may be used to evaluate and configure cardiac therapy such as, e.g., cardiac therapy provide by an implantable medical device performing cardiac resynchronization therapy (CRT). As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to optimize one or more settings, or parameters, of cardiac therapy (e.g., pacing therapy) such as CRT.

Various illustrative systems, methods, and graphical user interfaces may be configured to use electrode apparatus including external electrodes, display apparatus, and computing apparatus to noninvasively assist a user (e.g., a physician) in the evaluation of cardiac health and/or the configuration (e.g., optimization) of cardiac therapy. An illustrative system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 14. According to various embodiments, the electrode apparatus comprises about 40 electrodes. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, illustrative electrode apparatus 110 will be described in more detail in reference to FIGS. 2-3.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to locate, or place, one or more pacing electrodes proximate the patient's heart in conjunction with the configuration of cardiac therapy.

For example, the illustrative systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, pre-excitation intervals such as A-V and V-V intervals, etc. Illustrative systems and methods that use imaging apparatus and/or electrode apparatus may be described in U.S. Pat. No. 9,877,789 to Ghosh, U.S. Pat. No. 10,251,555 to Ghosh et al., U.S. Pat. No. 9,924,884 to Ghosh et al., U.S. Pat. No. 10,064,567 to Ghosh et al., each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. An exemplary system that employs ultrasound can be found in U.S. Pat. App. Pub. No. 2017/0303840 entitled NONINVASIVE ASSESSMENT OF CARDIAC RESYNCHRONIZATION THERAPY to Stadler et al., incorporated by reference in its entirety. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The computing apparatus 140 and the remote computing device 160 may each include display apparatus 130, 170, respectively, that may be configured to display and analyze data such as, e.g., electrical signals (e.g., electrocardiogram data), electrical activation times, electrical heterogeneity information, etc. For example, a plurality of electrical signals collected or monitored by the electrode apparatus 110 may be analyzed and evaluated by the computing apparatus 140 and the remote computing device 160 to determine or detect the QRS complexes therein such that, e.g., the QRS complexes can be further evaluated and analyzed for various metrics, activation time mapping, etc. Further, each QRS complex may be bracketed—the time period surrounding the QRS complex or the start and the end of the QRS complex may be determined. Further, for example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the therapeutic nature of one or more parameters related to cardiac therapy such as, e.g., pacing parameters, lead location, etc. More specifically, for example, the QRS complex of a single cardiac cycle may be evaluated for one or more metrics such as, e.g., QRS onset, QRS offset, QRS peak, electrical heterogeneity information (EHI), electrical activation times referenced to earliest activation time, left ventricular or thoracic standard deviation of electrical activation times (LVED), standard deviation of activation times (SDAT), average left ventricular or thoracic surrogate electrical activation times (LVAT), QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, activation maps may be created by interpolating a 2-by-20 matrix of activation times by first using an inverse distance-weighted interpolation step followed by a two-dimensional bi-cubic interpolation method. More specifically, the earliest (minimum) activation time across all valid electrodes may be determined and subtracted from each activation time. Over all electrodes, if an electrode is marked as valid, then the activation time is directly used in the bi-cubic interpolation step. If an electrode is marked as invalid, all valid electrodes are found within the same belt plane (anterior or posterior) and the contribution of each valid electrode to the interpolation is its activation time value weighted by the inverse of the distance squared from the invalid electrode. For instance, $$AT_{invalid} = \frac{\sum_{k=1}^{N}\left(\frac{1}{dist_k}\right)^2 \times AT_{k,valid}}{\sum_{k=1}^{N}\left(\frac{1}{dist_k}\right)^2}.$$

Where $$dist_k = \sqrt{(x_{invalid} - x_{k,valid})^2 + (y_{invalid} - y_{k,valid})^2}$$

Further, within the 2×10 array of activation times on each belt plane, for each set of 2×2 neighboring points that form a 'unit square', a system of 16 equations may be solved to find 16 coefficients of a two-dimensional polynomial function that can find the interpolated value at any fractional part within the unit square. Such process may be repeated for all possible neighboring 2×2 point sets.

In at least one embodiment, one or both of the computing apparatus 140 and the remote computing device 160 may be a server, a personal computer, a tablet computer, a mobile device, and a cellular telephone. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining or detecting QRS complexes and time periods related thereto, for determining QRS onsets, QRS offsets, medians, modes, averages, peaks or maximum values, valleys or minimum values, for determining electrical activation times, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of configuration information related to the cardiac therapy delivered by cardiac therapy apparatus such as, e.g., an implantable medical device.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information (EHI), textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more illustrative methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or nonvolatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and interfaces may be implemented using a computer readable storage medium, configured with a computer program, where the storage medium so configured causes the computer to operate in a specific and predefined manner to perform functions described herein. Further, in at least one embodiment, the illustrative systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
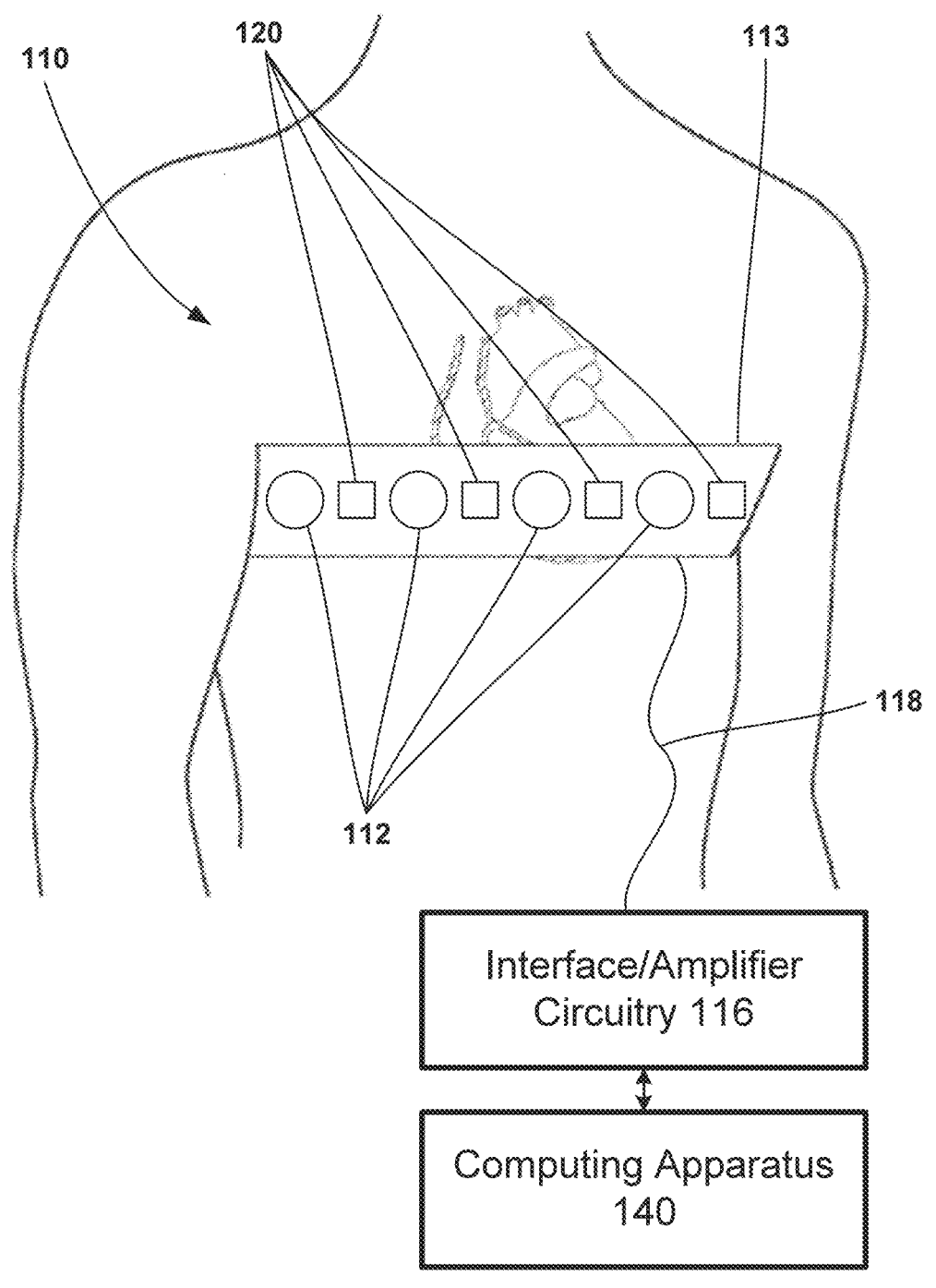
FIGS. 2-3 are diagrams of exemplary external electrode apparatus for measuring torso-surface potentials.

The illustrative electrode apparatus 110 may be configured to measure body-surface potentials of a patient 14 and, more particularly, torso-surface potentials of a patient 14. As shown in FIG. 2, the illustrative electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

The illustrative electrode apparatus 110 may be further configured to measure, or monitor, sounds from at least one or both the patient 14. As shown in FIG. 2, the illustrative electrode apparatus 110 may include a set, or array, of acoustic sensors 120 attached, or coupled, to the strap 113. The strap 113 may be configured to be wrapped around the torso of a patient 14 such that the acoustic sensors 120 surround the patient's heart. As further illustrated, the acoustic sensors 120 may be positioned around the circumference of a patient 14, including the posterior, lateral, posterolateral, anterolateral, and anterior locations of the torso of a patient 14.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other illustrative systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 14. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 14. Still further, in other examples, one or both of the electrodes 112 and the acoustic sensors 120 may be part of, or located within, two sections of material or two patches. One of the two patches may be located on the anterior side of the torso of the patient 14 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 14 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 14 across the left side of the patient 14 to the posterior side of the patient 14. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, the electrode apparatus 110 may include about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 14. Instead, the electrodes 112 and acoustic sensors 120 may be arranged in an array that extends only part of the way or partially around the patient 14. For example, the electrodes 112 and acoustic sensors 120 may be distributed on the anterior, posterior, and left sides of the patient with less or no electrodes and acoustic sensors proximate the right side (including posterior and anterior regions of the right side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to detect or determine QRS complexes, QRS onsets and offsets, and time periods related thereto and to provide electrocardiogram (ECG) signals, information, or data from the patient's heart as will be further described herein. The computing apparatus 140 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Illustrative systems and methods may noninvasively use the electrical information collected using the electrode apparatus 110 and the sound information collected using the acoustic sensors 120 to evaluate a patient's cardiac health and to evaluate and configure cardiac therapy being delivered to the patient.

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with less noise from averaging three caudally located reference signals.

Figure 3:
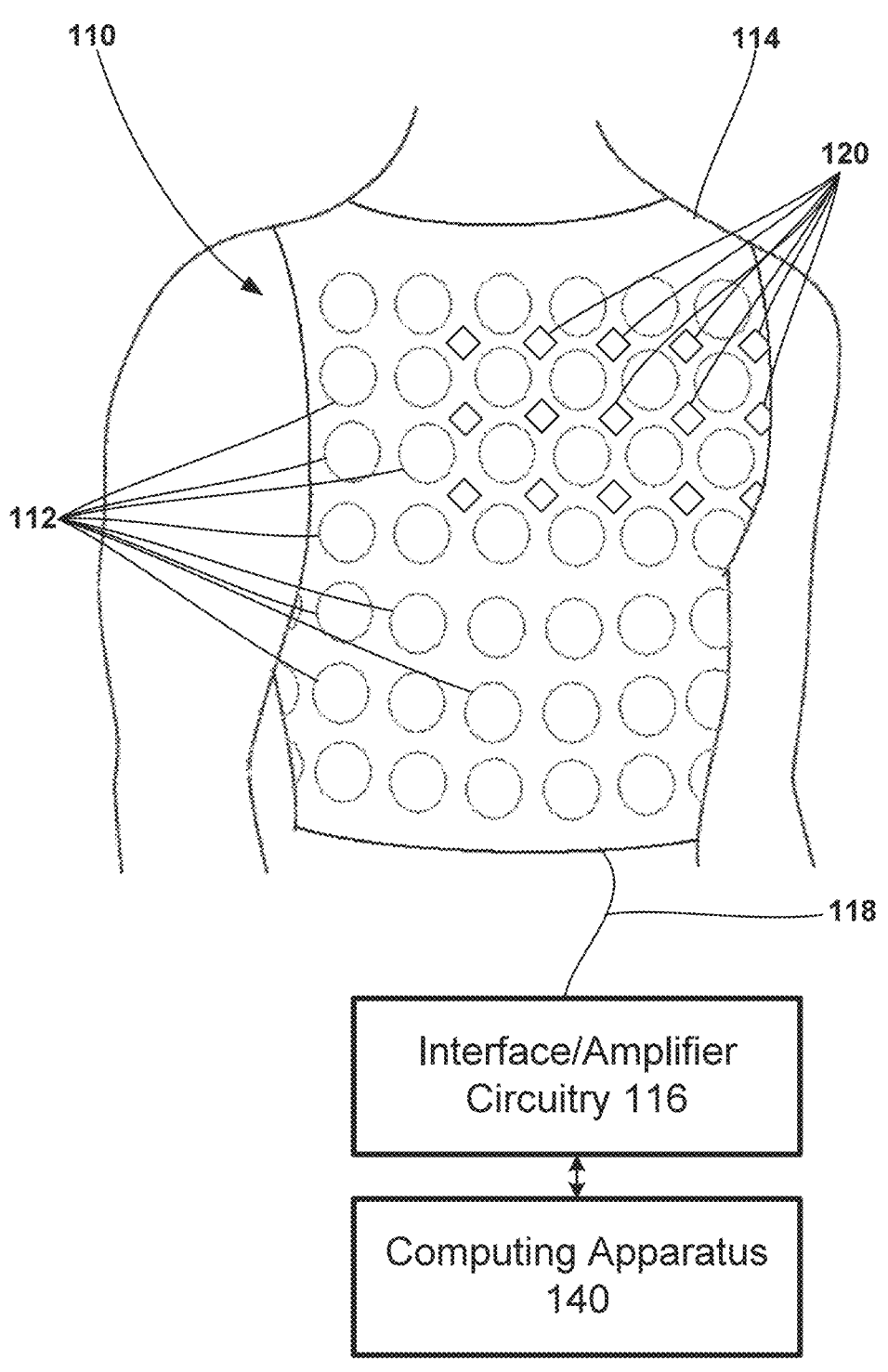

FIG. 3 illustrates another illustrative electrode apparatus 110 that includes a plurality of electrodes 112 configured to surround the heart of the patient 14 and record, or monitor, the electrical signals associated with the depolarization and repolarization of the heart after the signals have propagated through the torso of the patient 14 and a plurality of acoustic sensors 120 configured to surround the heart of the patient 14 and record, or monitor, the sound signals associated with the heart after the signals have propagated through the torso of the patient 14. The electrode apparatus 110 may include a vest 114 upon which the plurality of electrodes 112 and the plurality of acoustic sensors 120 may be attached, or to which the electrodes 112 and the acoustic sensors 120 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 14, including, for example, the posterior, lateral, posterolateral, anterolateral, and anterior locations of the torso of a patient 14.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 14. Further, the vest 114 may be marked to assist in determining the location of the electrodes 112 and the acoustic sensors 120 on the surface of the torso of the patient 14. In some examples, there may be about 25 to about 256 electrodes 112 and about 25 to about 256 acoustic sensors 120 distributed around the torso of the patient 14, though other configurations may have more or fewer electrodes 112 and more or fewer acoustic sensors 120.

The illustrative systems, methods, and interfaces may be used to provide noninvasive assistance to a user in the evaluation of a patient's cardiac health (e.g., prior to or during delivery of cardiac therapy) and/or evaluation and configuration of cardiac therapy being presently delivered to the patient (e.g., by an implantable medical device delivering pacing therapy, by a LVAD, etc.). Further, it is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

According to embodiments described herein, the illustrative system 100, which may be referred to as an ECG belt system, may be used with cardiac therapy systems and devices (e.g., CRT pacing devices) to calculate various metrics related to the cardiac health of a patient (e.g., the standard deviation of activation times (SDAT)) across one or more cardiac cycles (or heart beats), and in particular, based on activation times or other data gathered during each QRS event of the cardiac cycle (heart beat). According to various embodiments, the illustrative system 100 may be used to calculate, or generate, electrical heterogeneity information such as, e.g., SDAT, of cardiac cycles during delivery of CRT (e.g., the SDAT for cardiac cycles where CRT paces are delivered). For example, the illustrative system 100 may be used to calculate electrical heterogeneity information for cardiac cycles during biventricular and/or left ventricular pacing. Further, embodiments described herein may be used to evaluate a patient's cardiac health and/or non-CRT pacing. If electrical heterogeneity information is inaccurate, the output of the illustrative system 100 could be misleading, which could potentially impact lead placement (e.g., an implantable lead not being placed at an optimal spot) and/or optimal device programming. For example, if the SDAT is inaccurate, the SDAT may be artificially low, which may cause a clinician to not relocate currently positioned lead as opposed to repositioning the lead to obtain a better response.

An illustrative process to determine SDAT may first calculate the mean of valid channels, or signals, as follows:

$$mean_{AT} = \frac{\sum_{n=valid\ channels} Activation\_time_n}{Number\_of\_valid\_channels}.$$

Then, the squared standard deviation (for i=1 to number of valid channels) may be determined as follows:

$$squared_{STD} = \frac{1}{N} * \left(Activation_{time_i} - mean_{AT}\right)^2.$$

Then, the SDAT may be calculated as follows:

$$SDAT = \sqrt{squared_{STD}}$$

An illustrative process to determine LVAT may be described as the mean of the activation times of designated left ventricular channels, where each left ventricular activation time is referenced to the earliest activation time for all valid channels and may be represented as follows:

$$LVAT = \frac{\sum_{n=LV\ valid\ channels} Activation\_time_n}{Number\_of\_LV\_valid\_channels}.$$

In order to determine electrical heterogeneity information, each QRS event, or complex, with a plurality of cardiac cycles may be detected. Inaccurate detection of QRS events, or complexes, may cause false activation times to be detected leading to an inaccurate electrical heterogeneity information. According to various embodiments, a QRS event beginning or onset and/or a QRS event ending or offset is determined to give a bound on where to measure (e.g., determine a fiducial point within each of the plurality of cardiac signals). Embodiments herein describes a process for detecting QRS complexes and bounding them.

Figure 4:
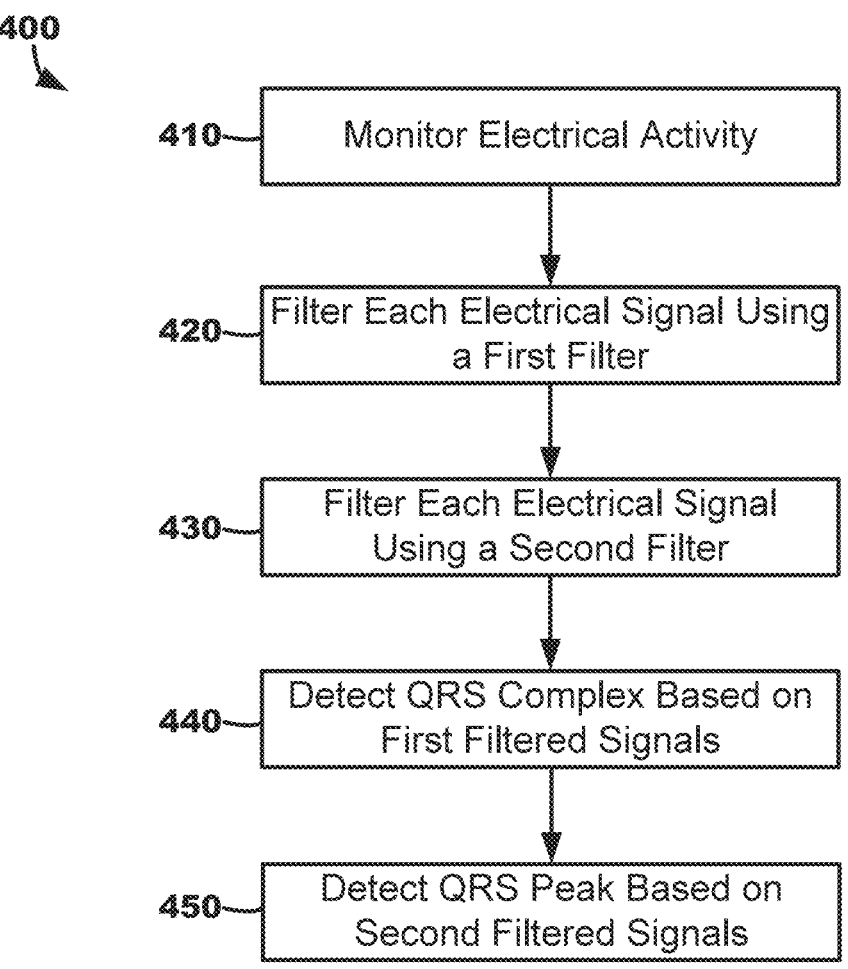
FIG. 4 shows an exemplary method for detecting QRS complexes.

An exemplary method 400 for detecting QRS complexes is shown in FIG. 4 in accordance with embodiments described herein. Electrical activity from tissue of a patient is monitored 410 using a plurality of external electrodes to generate a plurality of electrical signals over time. The plurality of electrodes may be external surface electrodes configured in a band or a vest similar to as described herein with respect to FIGS. 1-3. Each of the electrodes may be positioned or located about the torso of the patient so as to monitor electrical activity (e.g., acquire torso-potentials) from a plurality of different locations about the torso of the patient. Each of the different locations where the electrodes are located may correspond to the electrical activation of different portions or regions of cardiac tissue of the patient's heart.

The plurality of electrical signals are filtered 420 using a first filter having a first frequency range to generate a plurality of first filtered signals. According to various configurations, the first filter is a bandpass filter configured to filter out signals outside of a range of about 0.05 Hz to about 150 Hz. In some cases, the first filter is a bandpass filter configured to filter out signals outside of a range of about 10 Hz to about 32 Hz.

The plurality of electrical signals are filtered 430 using a second filter having a second frequency range different than the first frequency range to generate a plurality of second filtered signals. According to various configurations, the second filter is a bandpass filter configured to filter out signals outside of a range of about 0.05 Hz to about 150 Hz. In some cases, the first filter is a bandpass filter configured to filter out signals outside of a range of about 0.5 Hz to about 20 Hz.

It may be described that the first and second filter provide zero-phase digital filtering (Bessel filtering) by processing the input data in both the forward and time reversed directions. This results in the following characteristics: zero-phase distortion; a filter transfer function that is equal to the squared magnitude of the original IIR filter derived from the Bessel filter with a bilinear transformation; and a filter order that is double the order of the filter coefficients of a designed infinite impulse response (IIR) filter. Further, the zero-phase filtering may be accomplished through the following steps: filter the data in the forward direction; time-reverse the data; filter the data in the time-reverse direction; and time-reverse the output of the previous step to obtain the original time correspondence of the data.

An illustrative IIR filter and coefficients is as follows:

$$y[n] = \frac{1}{u_0}(b_0 x[n] + b_1 x[n-1] + b_2 x[n-2] + b_3 x[n-3] +$$
$$b_4 x[n-4] - a_1 y[n-1] - a_2 y[n-2] - a_3 y[n-3] - a_4 y[n-4])$$

The coefficients for an illustrative 20 HZ low-pass IIR filter may be as follows: a0=1.000, a1=−1.790211747962553, a2=0.804402717060237, a3=0, a4=0, b0=0.003547742274421, b1=0.007095484548842, b2=0.003547742274420, b3=0, b4=0.

The coefficients for an illustrative 10-32 Hz bandpass IIR filter may be as follows: a 0=1, a1=−3.74704252837753, a2=5.28457739282789, a3=−3.32507118261580, a4=0.787677403869584, b0=0.00422287948064259, b1=−

15

1.33226762955019e-15, b2=−0.00844575896128053, b3=−3.10862446895044e-15, b4=0.00422287948064337.

The coefficients for an illustrative 0.5-20 Hz bandpass IIR filter may be as follows: a0=1, a1=−3.79453631373899, a2=5.39795683527122, a3=−3.41222897663138, a4=0.808808595500041, b0=0.00338079909581213, b1=0, b2=−0.00676159819162336, b3=1.33226762955019e-15, b4=0.00338079909581224.

At least one QRS complex is detected 440 based on the plurality of first filtered signals. According to various configurations, detecting the at least one QRS complex comprises generating a first dispersion signal (e.g., standard deviation) based on the plurality of first filtered signals. The QRS complex is detected based on the dispersion signal. For example, the QRS complex may be detected by determining the peak of the first dispersion signal.

A QRS peak of the at least one QRS complex is detected 450 based on the plurality of second filtered signals and the detected at least one QRS complex. According to various configurations, detecting the at least one QRS peak comprises generating a second dispersion signal based on the plurality of second filtered signals. The second dispersion signal may be representative of the dispersion of the plurality of second filtered signals over time. The QRS peak is detected 450 based on the second dispersion signal.

The dispersion signals described herein may be representative of the dispersion of the plurality of cardiac signals over time. The dispersion signal may be the standard deviation of the plurality of cardiac signals over time. In other embodiments, the dispersion signals may be variance, a coefficient of variance, range, mean absolute deviation, a measure of central tendency (e.g., like the mean), interquartile deviation of amplitudes, median absolute deviation taken about a measure of central tendency like the mean, median, mode, and/or another statistical measure of the plurality of cardiac signals over time.

A blanking window of a predetermined length may be initialized based on the first dispersion signal. The blanking window may be used to determine a QRS peak by determining a maximum amplitude within the blanking window. According to various configurations, the predetermined length of the blanking window is in a range of about 100 ms to about 600 ms. In some cases, the predetermined length of the blanking window is about 200 ms. The predetermined length may be set in the factory and/or may be adjusted in the field. According to various implementations, the length of the blanking window is set based on at least one previously detected QRS complex.

In one or more embodiments a threshold function is be computed based on the QRS peak. The threshold function may be used to detect at least one subsequent QRS complex as will be described in more detail further herein. According to various implementations, the threshold function may be used to detect the at least one subsequent QRS complex by providing a sensitivity for the detection of the subsequent QRS complexes. The threshold function may be a decaying threshold signal that is based on one or both of the peaks of the first dispersion signal and the second dispersion signal. For example, decay parameters may be calculated using one or both of the peaks of the first dispersion signal and the second dispersion signal. The process may start over with each new QRS complex detected such that a different threshold function is computed for every QRS complex. According to various embodiments, the threshold function may be based on parameters of more than one previously detected QRS complex.

16

Figure 5:
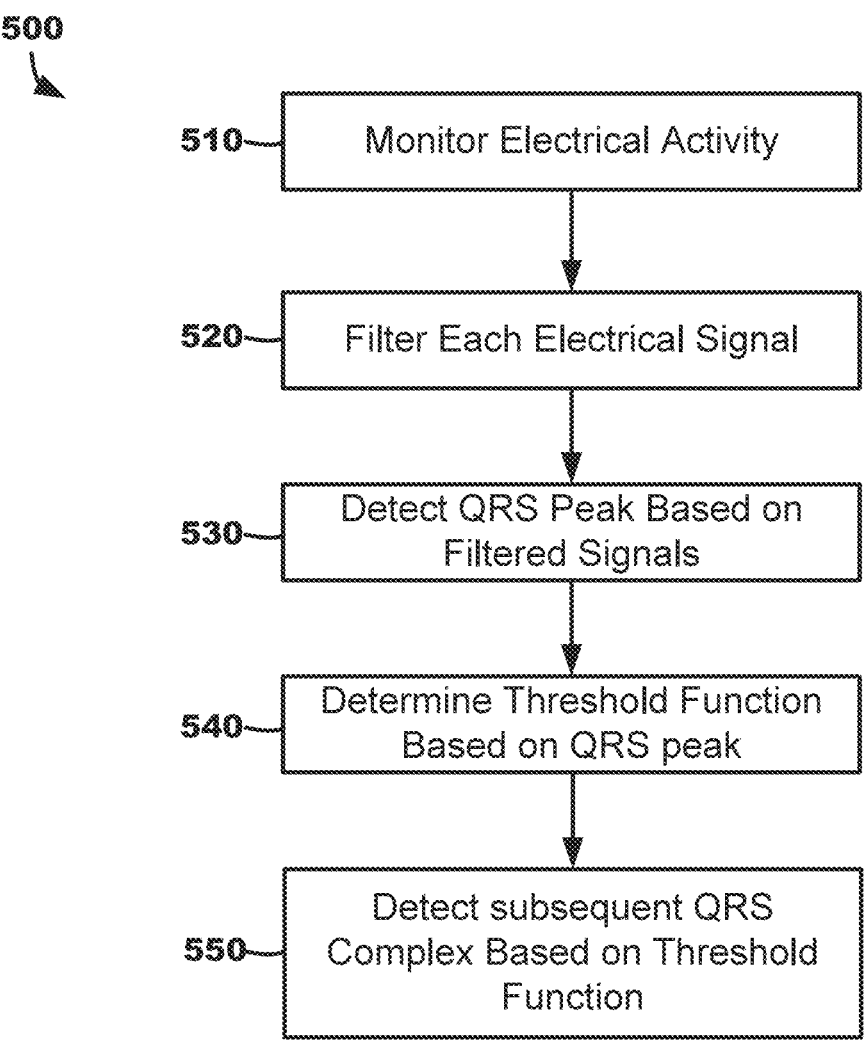
FIG. 5 illustrates an exemplary method for detecting a QRS complex and at least one subsequent QRS complex based on a threshold function.

An exemplary method 500 for detecting a QRS complex and at least one subsequent QRS complex based on a threshold function is shown in FIG. 5. Electrical activity from tissue of a patient is monitored 510 using a plurality of external electrodes to generate a plurality of electrical signals over time. The plurality of electrical signals are filtered 520 using at least one filter to generate a plurality of filtered signals. According to various implementations, the plurality of electrical signals are filtered using one or both of the bandpass filters 420, 430 described in conjunction with FIG. 4. A QRS peak is detected 530 based on the plurality of filtered signals, and a threshold function may be determined 540 based on the QRS peak. At least one subsequent QRS complex may be detected 550 based on (e.g., using) the threshold function.

Figure 6A:
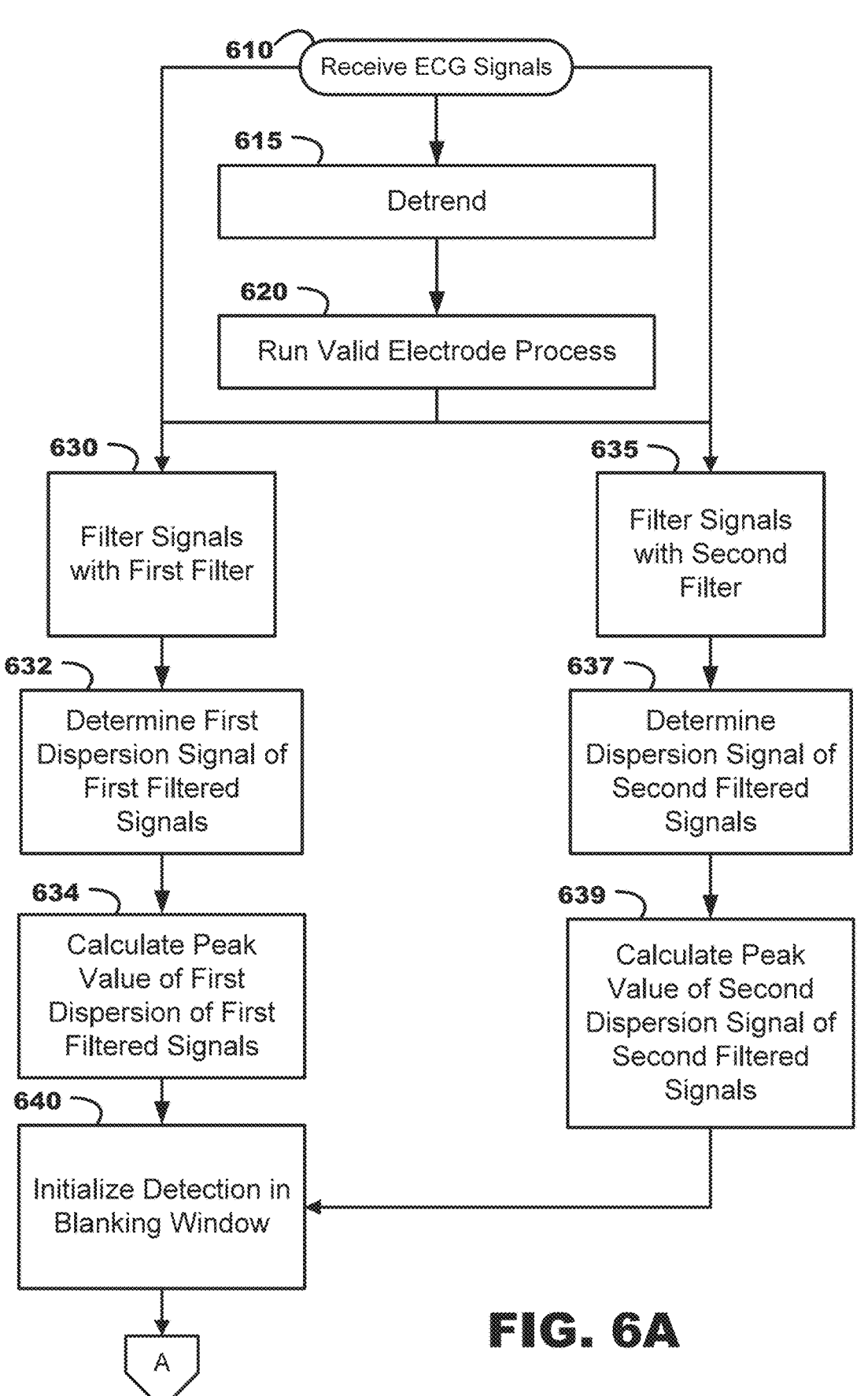
FIGS. 6A and 6B illustrate a more detailed process for detecting at least one QRS complex in accordance with embodiments described herein.
Figure 6B:
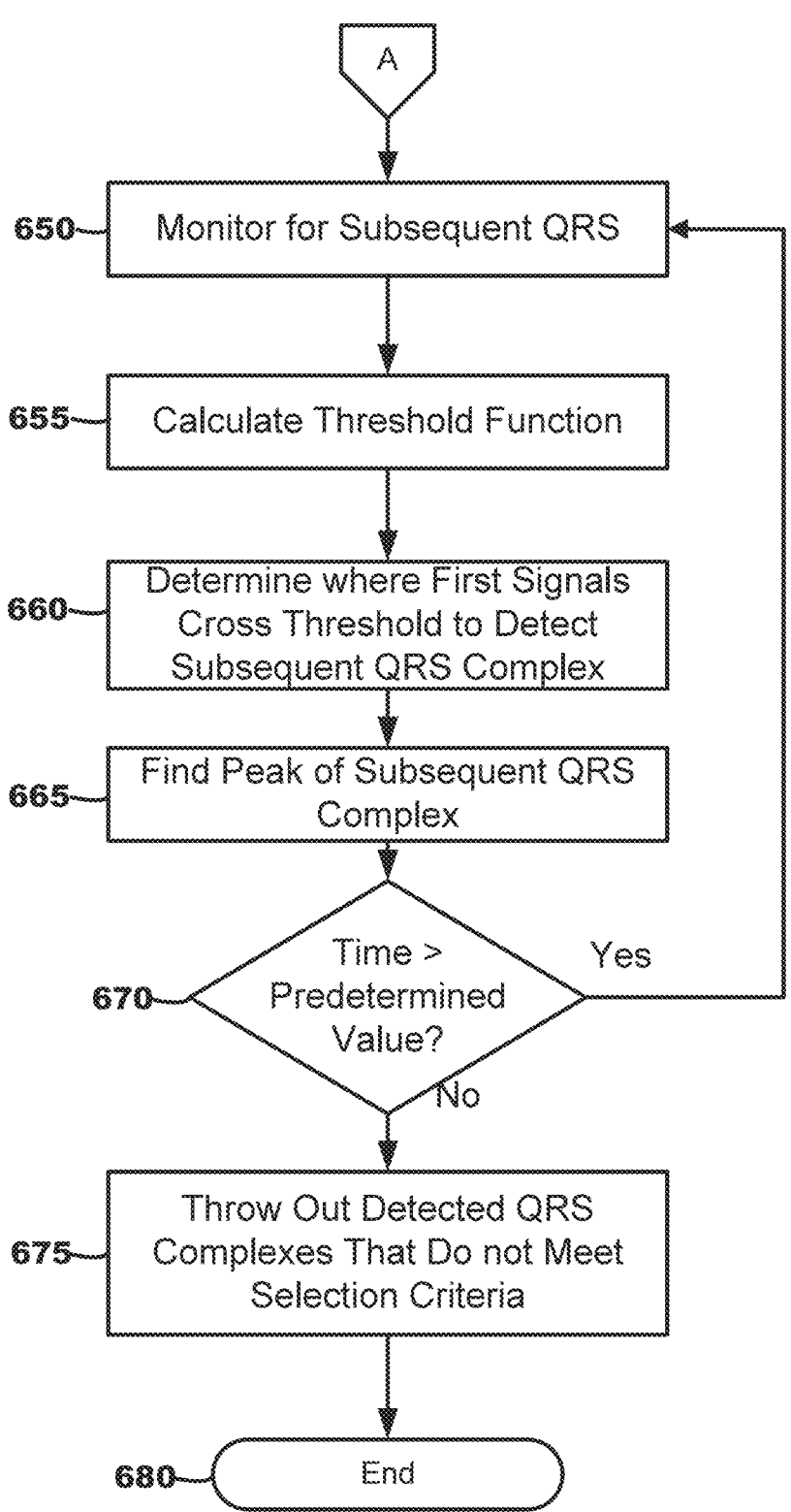

FIGS. 6A and 6B illustrate a more detailed process for detecting at least one QRS complex in accordance with embodiments described herein. A plurality of electrical signals, or ECG signals, received 610. According to various implementations, the ECG signals are received from an external electrode apparatus (e.g., ECG belt) as described herein. Initially, the ECG signals may be detrended 615 to remove any trend (e.g., a change in mean) over time from the ECG signals such as, e.g., mean increases or decreases over time. For example, it may be described that each ECG signal is de-trended to remove baseline drift using an algorithm based on the linear regression of the data. The algorithm may calculate the least squares regression line through all points within a 5000-sample recording, and then subtract the line from the original signal.

In at least one embodiment, the least squares regression line of the data may be defined as follows:

$$\hat{y}_i = b_0 + b_1 x_i$$

using the following equations:

$$b_1 = \frac{\sum_{i=1}^{n}(x_i - \bar{x})(y_i - \bar{y})}{\sum_{i=1}^{n}(x_i - \bar{x})^2} \text{ and. } b_0 = \bar{y} - b_1 \bar{x}.$$

Then, the predicted value may be subtracted from original data at each point in time to get the new de-trended value:

$$detrended_i = y_i - \hat{y}_i.$$

Further, the system may determine 620 whether all of the electrodes are valid, which, for example, may involve determining if any electrodes are returning outlier data that could indicate that the electrodes are not receiving accurate data. Illustrative systems and methods for determining whether electrodes and/or ECG signals are valid may be described in U.S. Pat. No. 9,924,884 issued on Mar. 27, 2018, and U.S. Pat. No. 10,064,567 issued on Sep. 4, 2018, each of which are incorporated herein by reference in their entirety.

In at least one embodiment, determination of which ECG signals to include in the calculations is accomplished through the following steps, using the ECG signals filtered per the 20 Hz low-pass filter, and the portion of the signals defined by onset and offsets as described herein. Pearson correlation coefficients may be calculated for each electrode compared to its two neighbor electrodes. A signal may be declared invalid if at least one of the following is true: peak-to-peak>6 mV; peak-to-peak<(0.2*median peak-to-peak); peak-to-peak<=0.12 mV; correlation<=0.6 for both neighbors (does not apply to electrodes at either end, electrode 1 and electrode 40); absolute value of ratio of minimum amplitude relative to baseline and maximum amplitude relative to baseline is greater than 1, where baseline is the signal amplitude at onset AND minimum amplitude is at offset; and absolute value of ratio of maximum amplitude relative to baseline and minimum amplitude relative to baseline is greater than 1, where baseline is the signal amplitude at onset AND maximum amplitude is at offset; lead-off per the amplifier between onset and offset of the selected beat. Any signal that is not declared invalid may be determined to be valid.

The ECG signals are filtered 630 using a first filter to create first filtered signals. The first filter may the same filter as that described in conjunction with FIG. 4. A first dispersion signal is determined based on the of the first filtered signals 632. A peak value of the first dispersion signal is determined 634. According to various configurations, a minimum of a percentage of the peak and a predetermined value may be used to determine a location of the first QRS complex. For example, a minimum of about 35% of the peak and value about 0.075 may be used to determine a location of the first QRS complex. In some cases, it may be determined whether the 35% of the peak is less than a base threshold (e.g., 0.025). If it is determined that the minimum is less than the base threshold, the base threshold may be used to detect the time of the first QRS complex. The time of the first QRS complex may be used to initialize 640 a blanking window for use in determining the first QRS peak.

The ECG signals are filtered 635 with a second filter to create second filtered signals. The second filter may the same filter as that described in conjunction with FIG. 4. The ECG signals may be filtered 630 with the first filter in parallel as the ECG signals are filtered 635 by the second filter. In some cases, the ECG signals are filtered 630 with the first filter in series with the ECG signals being filtered 635 with the second filter. A second dispersion signal of the second filtered signals is determined 637. Detection of the first QRS peak is determined by determining 639 the maximum amplitude of the second dispersion signal within the blanking window.

The system may continue to monitor 650 the ECG signals for at least one subsequent QRS complex. The monitoring may initiate, or occur, after a predetermined amount of time has expired after the detected first QRS complex and/or a predetermined amount of time after the first QRS peak. For example, the system may begin to monitor for at least one subsequent QRS complex in a range of about 100 ms to about 600 ms after the detected first QRS peak. In some cases, the system begins to monitor for at least one subsequent QRS complex about 200 ms after the detected first QRS peak.

A threshold function may be calculated 655 based on the first detected QRS complex. The threshold function provides a sensitivity for detecting one or more subsequent QRS complexes. Additional detail with respected to an illustrative threshold function calculation or determination is described further herein with respect to FIG. 7. It is determined 660 where the second dispersion signal crosses the threshold based on the threshold function to detect a subsequent QRS complex. A new blanking window is initialized and the subsequent QRS peak is determined 665 using the same methods as those used for determining the peak of the first QRS peak.

It is determined 670 whether an elapsed time from the first QRS peak to a total monitoring time is less than a predetermined value. The predetermined value may be in a range of about 4000 ms to about 5000 ms. In some cases, the predetermined value is about 4750 ms. In some embodiments, the predetermined interval may be set based on the total monitoring time, e.g. total monitoring time—250 ms. If total monitoring time is 10 s (10000 ms) then value of this predetermined interval may be about 9750 ms. If it is determined that the elapsed time is less than the predetermined value, the system starts monitoring for another QRS complex. If it is determined 670 that the elapsed time is greater than the predetermined value, the system may continue to throw out 675 any detected QRS complexes that do not meet selection criteria and the process ends 680. The selection criteria may include that all detected QRS complexes are greater than a predetermined length. For example, the predetermined length may be in a range of about 250 ms to about 600 ms. In some cases, the predetermined length is about 400 ms. According to various implementations, the selection criteria may include that the QRS complexes be detected within a predetermined time limit. The predetermined time limit may be in a range of about 4000 ms to about 5000 ms. In some cases, the predetermined time limit is about 4750 ms.

Figure 7:
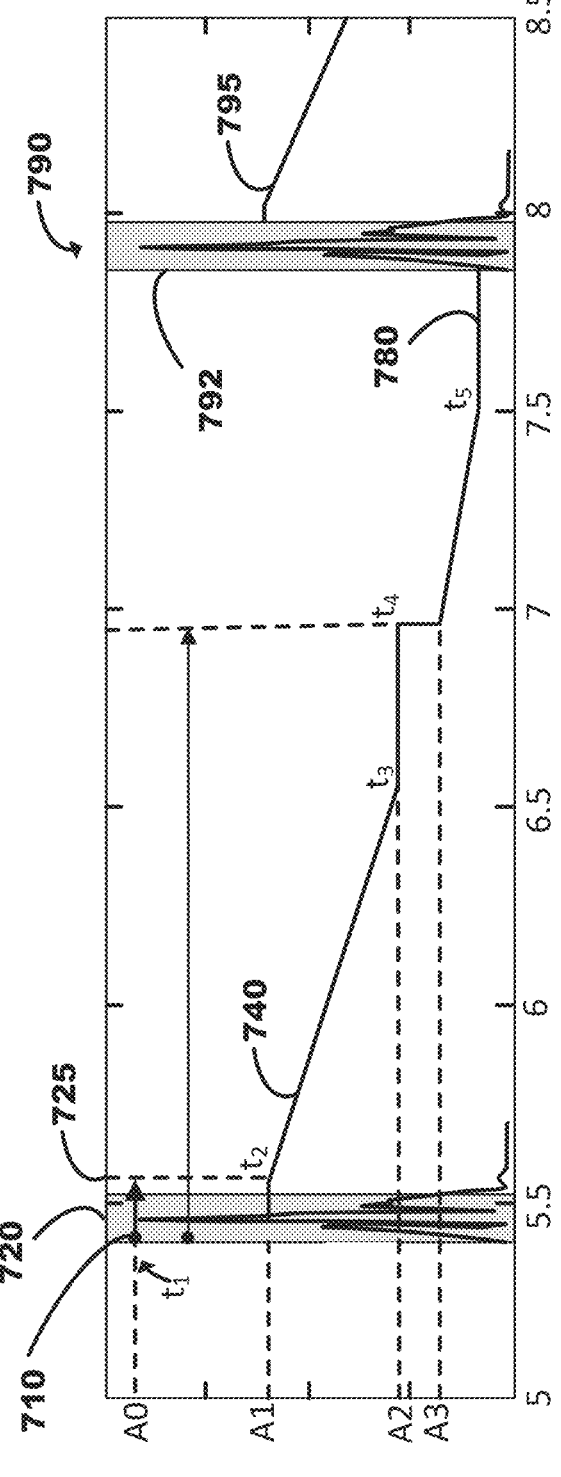
FIG. 7 shows an example threshold function in accordance with embodiments described herein.

FIG. 7 shows an example threshold function in accordance with embodiments described herein. Here, the maximum amplitude of the first filtered signal is used to detect a first QRS complex. According to various implementations, the maximum amplitude of the first filtered signal is used to determine the start 710 of the blanking window (A0) at time $t_1$. The maximum amplitude within the blanking window 720 is determined to be the QRS peak. After a predetermined amount of time 725 following the start 710 of the blanking window, the system may proceed to monitor for subsequent QRS complexes at time $t_2$.

A threshold function 740 may then be calculated based on the detected QRS peak. The threshold function may be configured to provide a sensitivity for detection of subsequent QRS complexes. According to various embodiments described herein, the threshold function 740 may be configured to decrease at time $t_2$ until at least one subsequent QRS complex is detected and/or a base threshold 780 is reached. According to various implementations, the base threshold is a base percentage of the QRS peak. For example, the base threshold may be in a range of about 0.5 percent to about 5 percent of the QRS peak. In some cases, the base threshold is about 3%

According to various implementations, the threshold function 740 is configured to decrease from a first threshold percentage (A1) at time $t_2$ to a second threshold percentage (A2) at time $t_3$. At least a portion of the decrease may be a substantially linear decrease or a nonlinear decrease. The threshold function may be configured to decrease from the A1 at time, $t_2$, (e.g., a predetermined amount of time after the start of the blanking window) to A2 at $t_3$. A1 may be in a range of about 50 percent to about 80 percent of the QRS peak 730. In some cases, A1 is about 60% of the QRS peak 730. A2 may be in a range of about 10 percent to about 50 percent of the QRS peak 730. In some cases, A2 is about 30% of the QRS peak.

The threshold function 730 may be configured to stay constant between $t_3$ and $t_4$. According to various configurations $t_1$ is about 0 ms, $t_2$ is about 200 ms, $t_3$ is about 1200 ms, $t_4$ is about 1700 ms and/or $t_5$ is about 2200 ms. In some cases, the threshold function 740 is configured to drop at $t_4$ to a third threshold percentage (A3) of the QRS peak. A3 may be in a range of about 5 percent to about 20 percent of the QRS peak 730. In some cases, A3 is about 15% of the QRS peak. The threshold function may then be configured to drop linearly or nonlinearly between $t_4$ and $t_5$ to the base threshold percentage. If a subsequent QRS complex 790 is detected, a new blanking window 792 and a new threshold function 795 are established.

Figure 8:
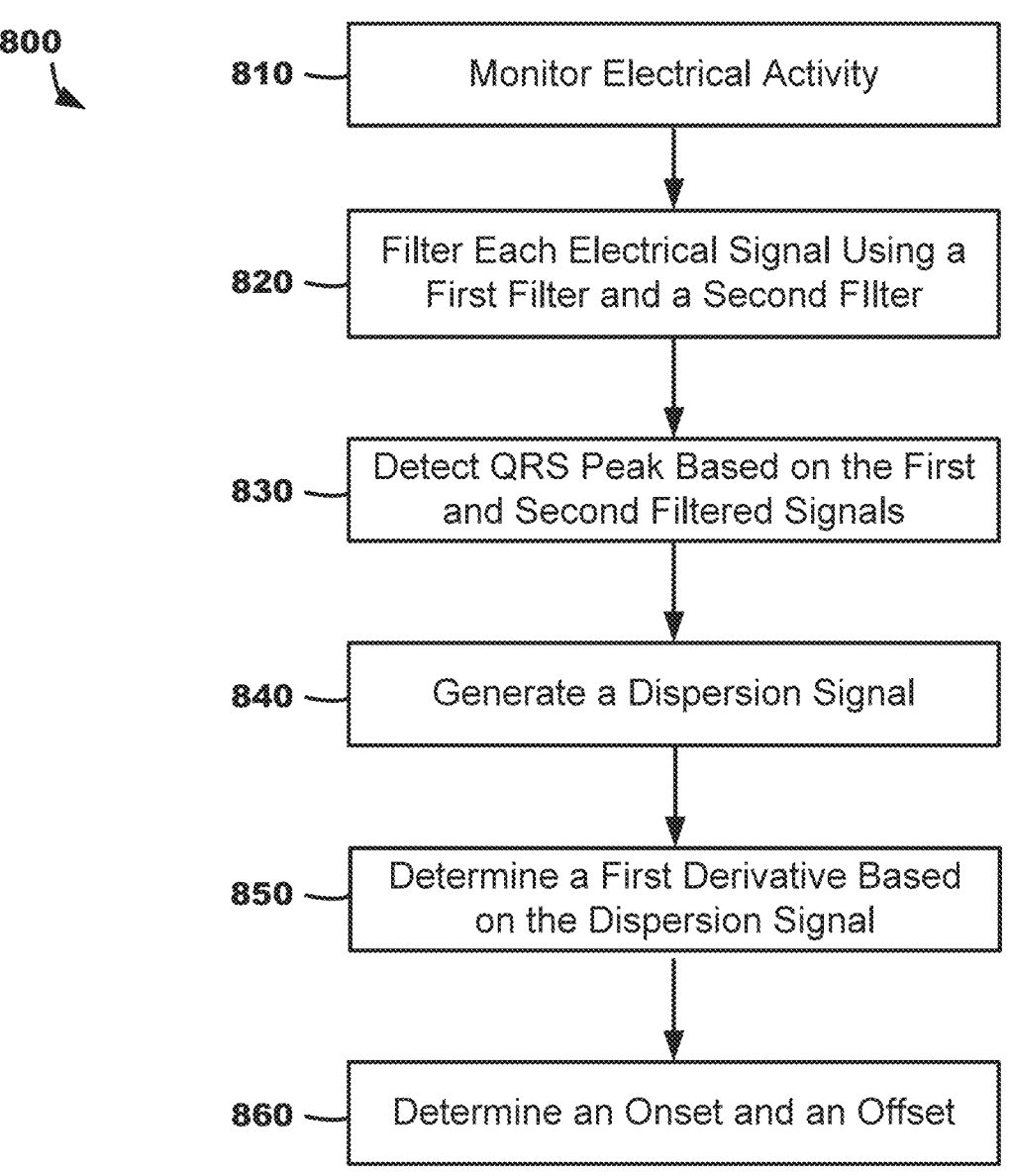
FIG. 8 illustrates an exemplary method for determining an onset and an offset of a corresponding QRS complex.
Figure 9:
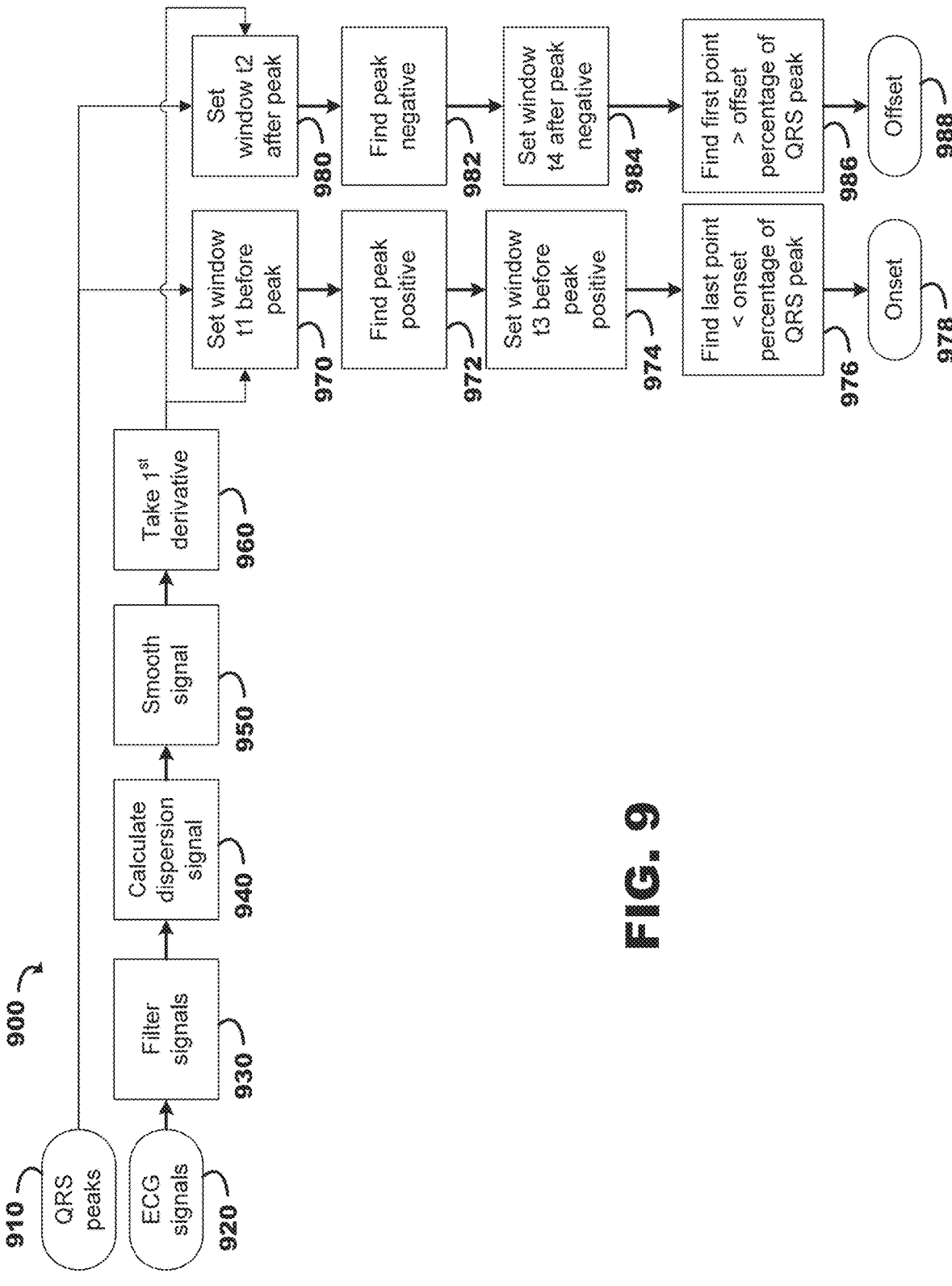
FIGS. 9 and 10A-10C show a more detailed process for determining the onset and offset values for at least one QRS complex in accordance with embodiments described herein.

An exemplary method 800 for determining an onset and an offset of a corresponding QRS complex is shown in FIG. 8. Electrical activity from tissue of a patient is monitored 810 using a plurality of external electrodes to generate a plurality of electrical signals over time. The plurality of electrical signals are filtered 820 using a first filter and the second filter to generate a plurality of first filtered signals and plurality of second filtered signals, the first filter and the second filter having different frequency ranges. A QRS peak is detected 830 based on the plurality of first filtered signals and the plurality of second filtered signals as described herein with respect to FIGS. 4-6.

A dispersion signal may be generated 840 from the plurality of second filtered signals, and then a first derivative signal may be determined 850 based on the dispersion signal. At least one of a QRS onset time and a QRS offset time corresponding to the QRS complex may be determined 860 based on the first derivative signal.

According to various implementations, the onset time and the offset time may be used to calculate an activation time for the at least one QRS complex for each of the plurality of cardiac signals. In particular, a fiducial point (e.g., maximum negative slope) within a QRS duration between the QRS onset time value and the QRS offset time value may be determined, which may be used to determine an activation time. At least one metric of electrical heterogeneity may be determined based on the activation times of the plurality of cardiac signals for each QRS complex.

FIGS. 9 and 10A-10C illustrate a more detailed process 900 for determining the onset and offset values for at least one QRS complex in accordance with embodiments described herein. The timing of the one or more QRS peaks are received 910. In other words, the time at which each of the QRS peaks occurs may have been determined, e.g., using substantially the same processes that is described in conjunction with FIGS. 4-7 or may be determined using one or more different processes, and then received 910.

Figure 10A:
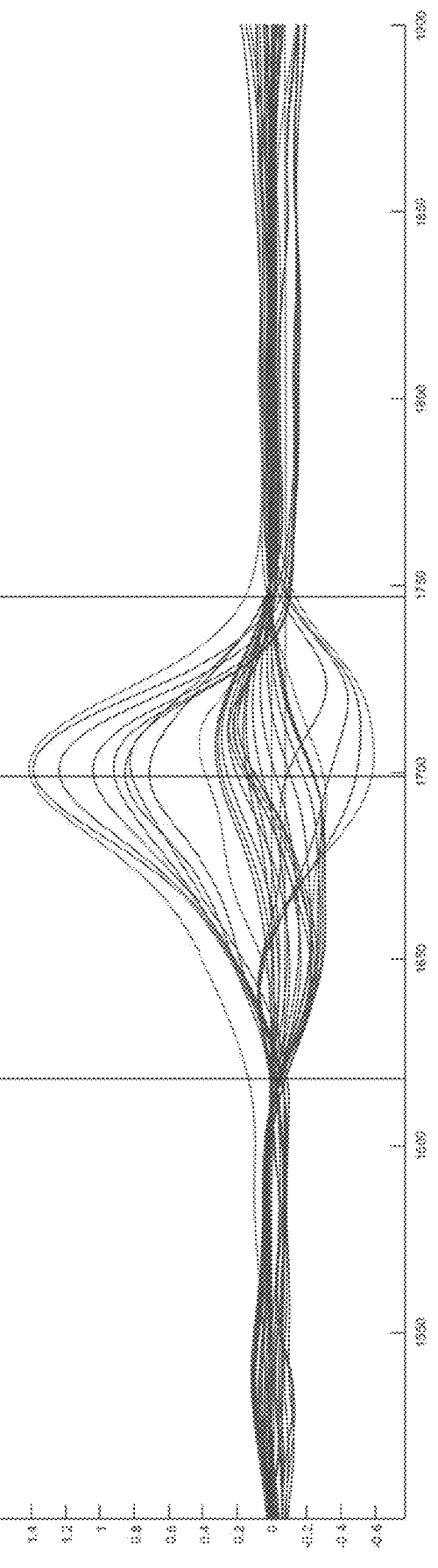

Additionally, the ECG signals may be received 920. For example, the ECG signals may be received from an ECG belt, and then the ECG signals are filtered 930 as shown in the example of FIG. 10A. According to various configurations, the ECG signals are filtered using one or more bandpass filters configured to remove, or "filter out," signals outside of a predetermined range. For example, the bandpass filter may be configured to remove, or "filter out," signals outside of a range of about 0.5 to about 20 Hz.

Figure 10B:
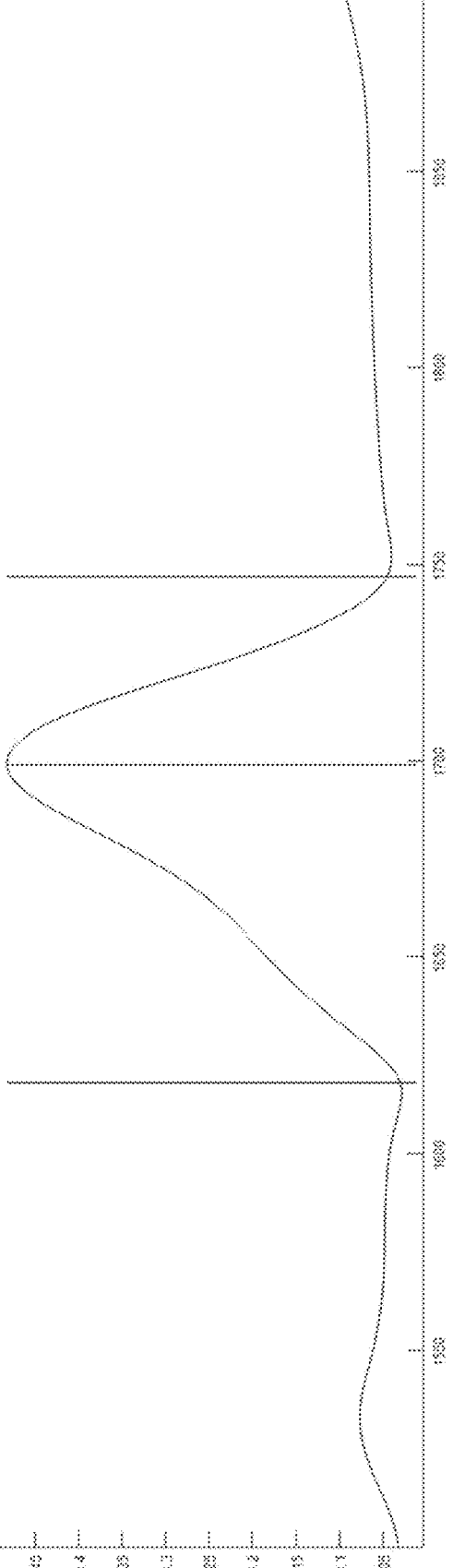

A dispersion signal of the filtered signals is determined 940 as shown in FIG. 10B, and then smoothed 950. The dispersion signal may be smoothed to reduce outlier data due to noise for example. According to various implementations, the dispersion signal may be smoothed using a 25-point equal-weighted smoother.

Figure 10C:
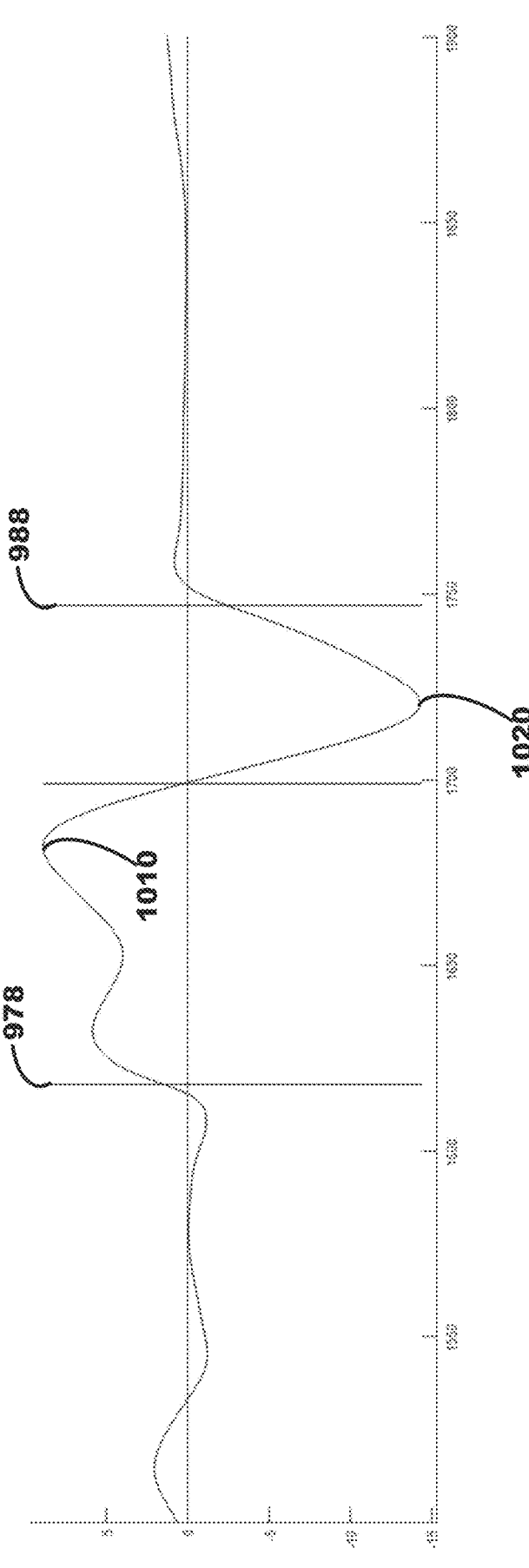

A first derivative signal of the smoothed signal is generated as shown in FIG. 10C. A first window is set 970 a predetermined amount of time before the QRS peak and is set 980 a predetermined amount of time after the QRS peak. The amount of time before the QRS peak and the amount of time after the QRS peak may be substantially the same. For example, the predetermined period of time before the QRS peak and after the QRS peak may be in a range of about 100 ms to about 150 ms. In some cases, the predetermined period of time before the QRS peak and after the QRS peak is about 120 ms. In one or more embodiments, the predetermined amount time before the QRS peak and the predetermined amount of time after the QRS peak are different. The predetermined amount before and after the QRS peak may be set in the factory and/or may be adjusted in the field.

The peak positive 1010 and the peak negative 1020 of the derivative signal is determined. A second window is set 974 a predetermined amount of time before the peak positive 1010 and is set 984 a predetermined amount of time after peak negative 1020. The amount of time before the peak positive and the amount of time after the peak negative may be substantially the same. For example, the predetermined amount of time before the peak positive and after the peak negative may be in a range of about 100 ms to about 150 ms. In some cases, predetermined amount of time before the peak positive and after the peak negative is about 120 ms. In some configurations, the predetermined amount of time before the peak positive and the predetermined amount of time after the peak negative are different than one another. The predetermined amount of time before the peak positive and after the peak negative may be set in the factory and/or may be adjusted in the field.

The QRS onset 978 is determined by finding 976 the last point in the second window that is less than a first predetermined percentage of the QRS peak. The first predetermined percentage may be in a range of about 10% to about 30% of the QRS peak. In some cases, the first predetermined percentage is about 20%.

The QRS offset 988 is determined by finding 986 a first time in the second window that is greater (i.e. more positive) than a second predetermined percentage of the QRS peak. The second predetermined percentage may be in a range of about 10% to about 30% of the QRS peak. In some cases, the second predetermined percentage is about 20%. It is to be understood that the first predetermined percentage and the second predetermined percentage may be set in the factory and/or may be programmable in the field. The first and the second predetermined percentage may be based on QRS history of a patient and/or multiple patients.

Figure 11:
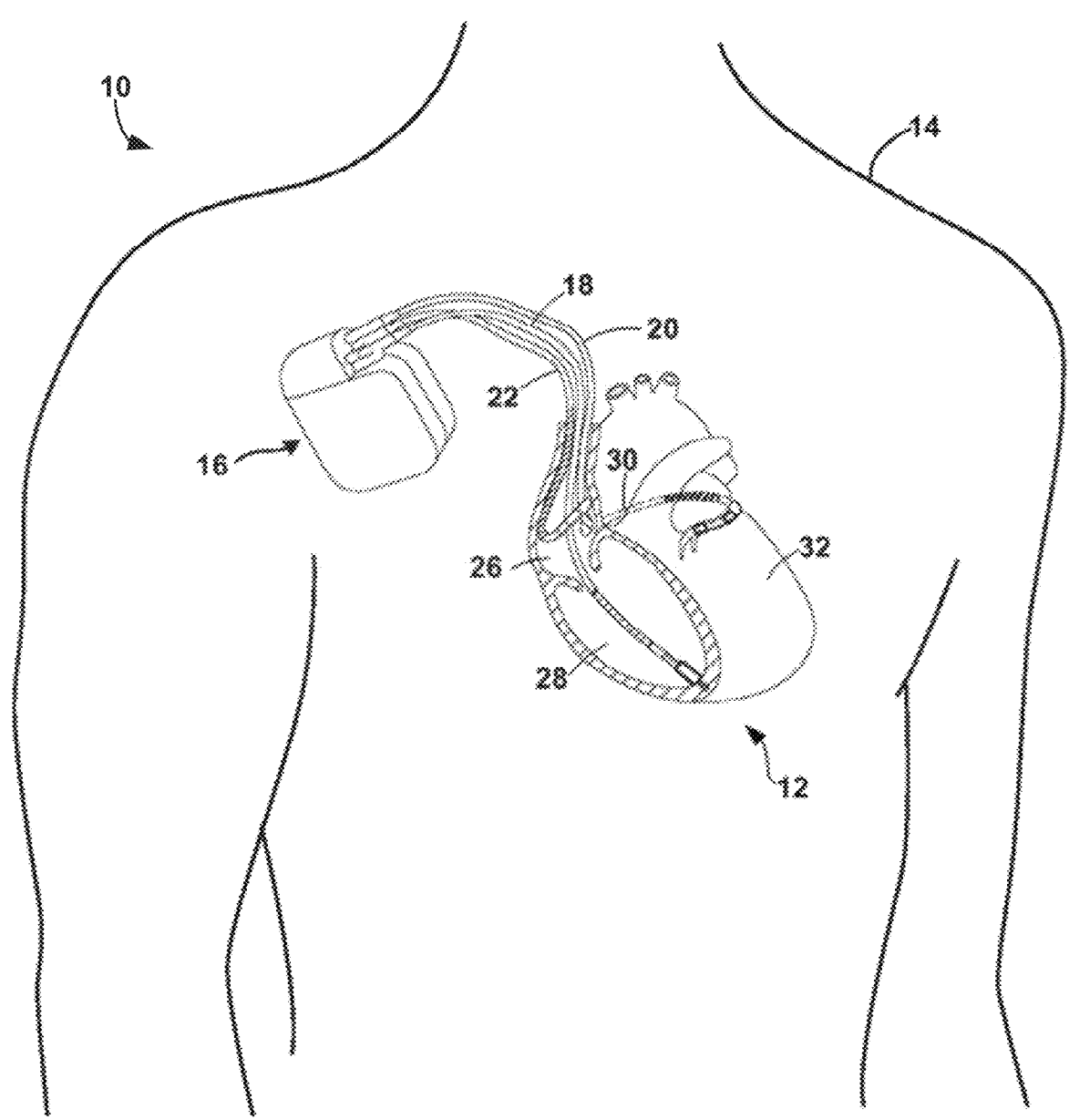
FIG. 11 is a diagram of an illustrative system including an illustrative implantable medical device (IMD).

Illustrative cardiac therapy systems and devices may be further described herein with reference to FIGS. 11-13 that may utilizes the illustrative systems, interfaces, methods, and processes described herein with respect to FIGS. 1-10.

FIG. 11 is a conceptual diagram illustrating an illustrative therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 11, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads

18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., A-V delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 12A:
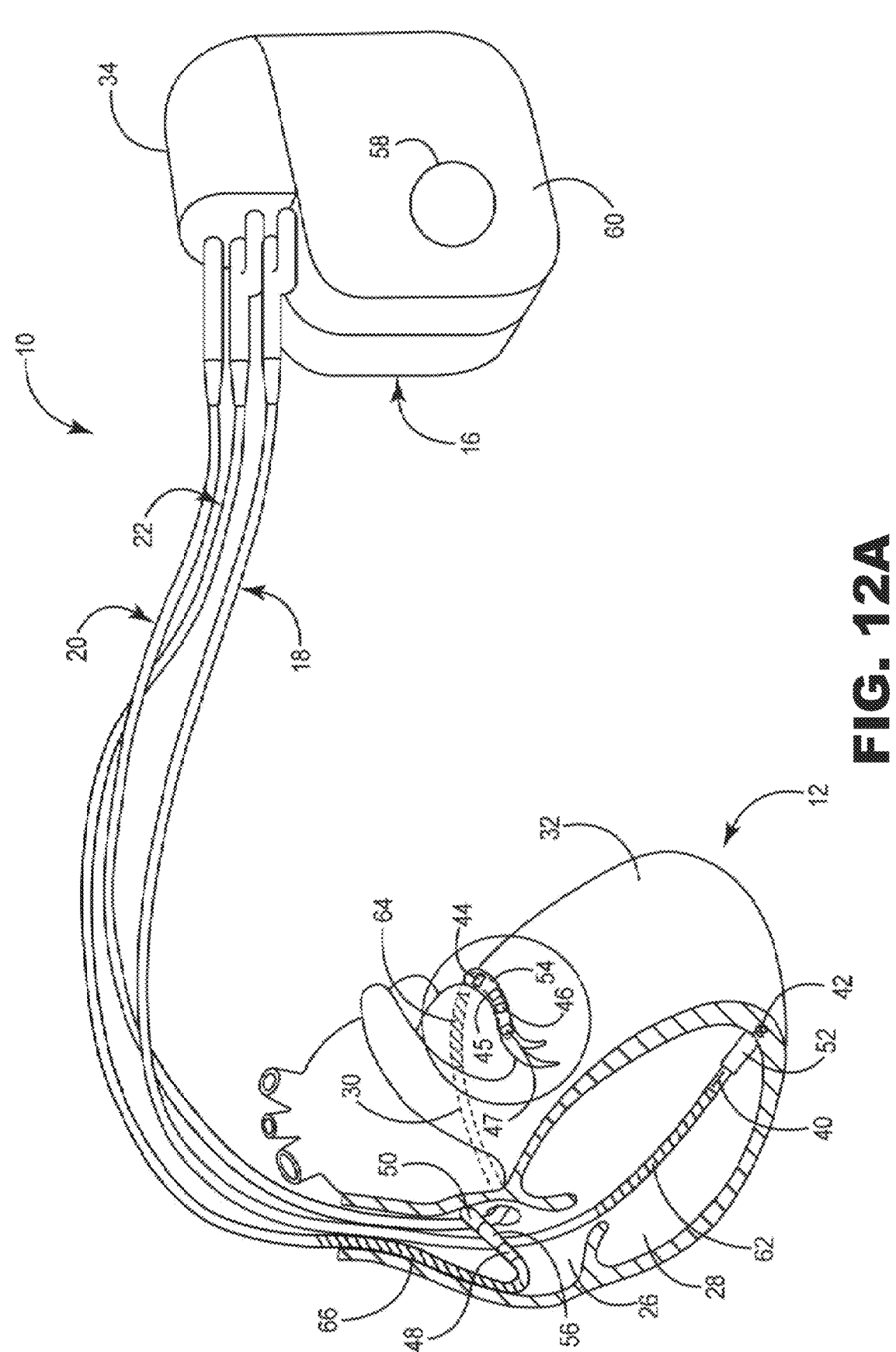
FIG. 12A is a diagram of the illustrative IMD of FIG. 11.
Figure 12B:
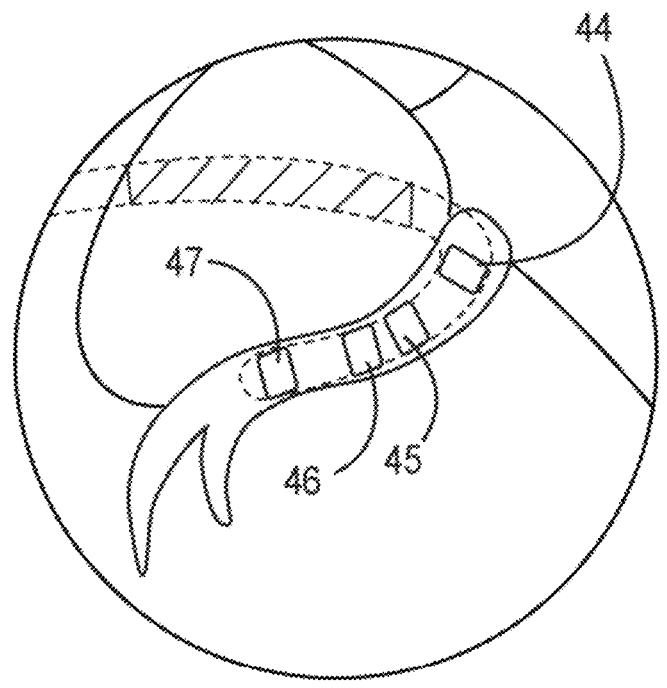
FIG. 12B is a diagram of an enlarged view of a distal end of the electrical lead disposed in the left ventricle of FIG. 12A.

FIGS. 12A-12B are conceptual diagrams illustrating the IMD 16 and the leads 18, 20, 22 of therapy system 10 of FIG. 11 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 12A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 12A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the illustrative therapy system 10 illustrated in FIGS. 11-13 is merely one example. In other examples, the therapy system may include epicardial leads and/or patch electrodes instead of or in addition to the transvenous leads 18, 20, 22 illustrated in FIG. 11. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 11). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 11-13. Still further, other therapy systems may include a single lead that extends from the IMD 16 into the right atrium 26 or the right ventricle 28, or two leads that extend into a respective one of the right atrium 26 and the right ventricle 28.

Figure 13A:
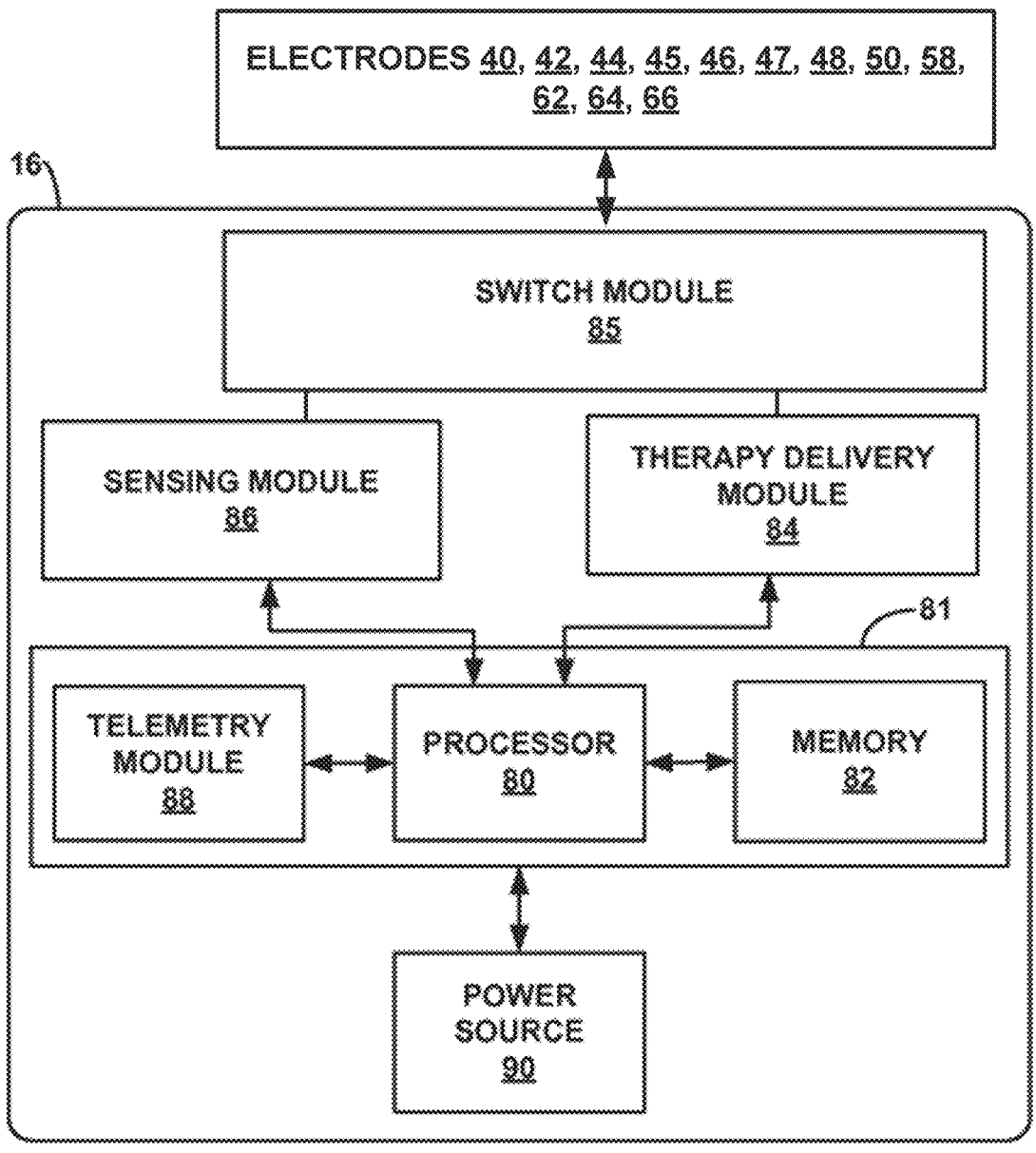
FIG. 13A is a block diagram of an illustrative IMD, e.g., of the systems of FIGS. 11-12.

FIG. 13A is a functional block diagram of one illustrative configuration of the IMD 16. As shown, the IMD 16 may include a control module 81, a therapy delivery module 84 (e.g., which may include a stimulation generator), a sensing module 86, and a power source 90.

The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An illustrative capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81

(e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 13B:
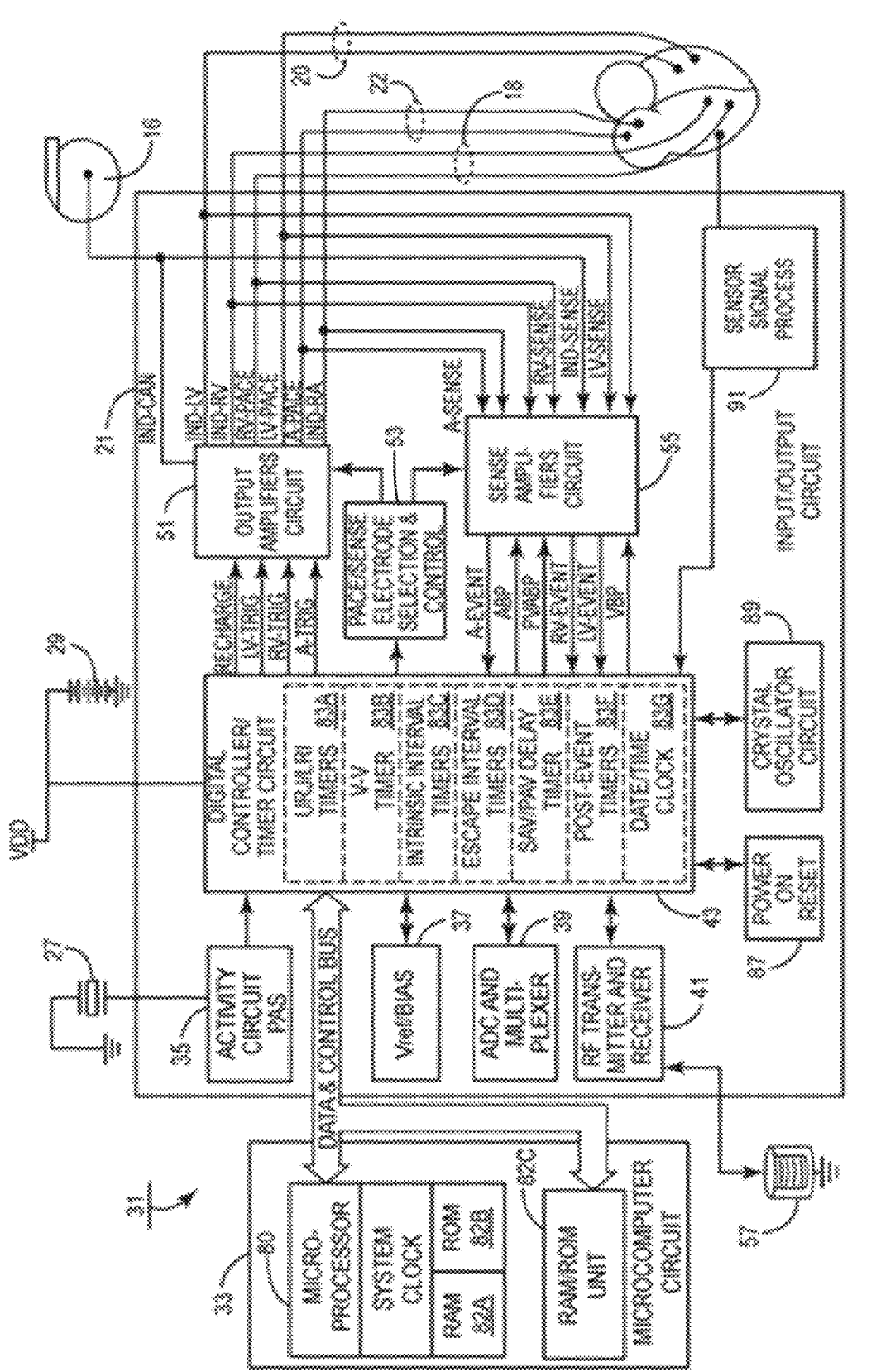
FIG. 13B is another block diagram of an illustrative IMD (e.g., an implantable pulse generator) circuitry and associated leads employed in the systems of FIGS. 11-12).

FIG. 13B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, illustrative IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the illustrative systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative A-V delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present disclosure. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, V-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by A-V delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

Embodiment 1. A system for use in cardiac evaluation comprising:
  an electrode apparatus comprising a plurality of external electrodes to be disposed proximate a patient's skin; and
  a computing apparatus comprising processing circuitry, the computing apparatus operably coupled to the electrode apparatus and configured to:
  monitor electrical activity from tissue of a patient using a plurality of external electrodes to generate a plurality of electrical signals over time;
  filter the plurality of electrical signals using a first filter having a first frequency range to generate a plurality of first filtered signals;
  filter the plurality of electrical signals using a second filter having a second frequency range different than the first frequency range to generate a plurality of second filtered signals;
  detect at least one QRS complex based on the plurality of first filtered signals; and
  detect a QRS peak of the at least one QRS complex based on the plurality of second filtered signals and the detected at least one QRS complex.

Embodiment 2. The system of embodiment 1, wherein the first filter is a bandpass filter configured to filter out frequencies outside of a range of about 10 Hz to about 32 Hz.

Embodiment 3. The system as in any one of embodiments 1-2, wherein the second filter is a bandpass filter configured to filter out frequencies outside of a range of about 0.5 Hz to about 20 Hz.

Embodiment 4. The system as in any one of embodiments 1-3, wherein detecting the at least one QRS complex comprises:
  generating a dispersion signal based on the plurality of first filtered signals, wherein the dispersion signal is representative of the dispersion of the plurality second filtered signals over time; and
  detecting the at least one QRS complex based on the dispersion signal.

Embodiment 5. The system as in any one of embodiments 1-4, wherein detecting the QRS peak comprises:
  determining a standard deviation of the plurality of second filtered signals;
  initializing a blanking window of a predetermined length based standard deviation; and
  detecting the peak amplitude of the plurality of second filtered signals within the blanking window.

Embodiment 6. The system as in any one of embodiments 1-5, wherein the computing device is further configured to:
  determine a threshold function based on the QRS peak, the threshold function configured to provide sensitivity for detecting at least one subsequent QRS complex; and
  detect the at least one subsequent QRS complex based on the threshold function.

Embodiment 7. The system as in any one of embodiments 1-6, wherein the computing apparatus is further configured to determine a QRS onset time value and a QRS offset time value corresponding to the at least one QRS complex.

Embodiment 8. The system of embodiment 7, wherein determining the QRS onset time value and the QRS offset time value comprises:

generating a dispersion signal from the plurality second filtered signals, wherein the dispersion signal is representative of the dispersion of the plurality second filtered signals over time, determining a first derivative signal based on the dispersion signal;

determining a first window of the first derivative signal within a first time period before a peak positive value of the first derivative signal;

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

Embodiment 9. The system of embodiment 7, wherein the computing apparatus is further configured to determine a plurality of activation times for the at least one QRS complex based on the plurality of cardiac signals within a QRS duration between the QRS onset time value and the QRS offset time value.

Embodiment 10. The system of embodiment 9, wherein the computing apparatus is further configured to determine at least one metric of electrical heterogeneity based on the plurality of activation times.

Embodiment 11. The system as in any one of embodiments 1-10, wherein the electrical activity is representative of depolarization of cardiac tissue that propagates through the torso of the patient.

Embodiment 12. The system as in any one of embodiments 1-11, wherein the plurality of external electrodes comprises a plurality of surface electrodes to be located proximate skin of the patient's torso.

Embodiment 13. A method for use in cardiac evaluation comprising:

monitoring electrical activity from tissue of a patient using a plurality of external electrodes to generate a plurality of electrical signals over time;

filtering the plurality of electrical signals using a first filter having a first frequency range to generate a plurality of first filtered signals;

filtering the plurality of electrical signals using a second filter having a second frequency range different than the first frequency range to generate a plurality of second filtered signals;

detecting at least one QRS complex based on the plurality of first filtered signals; and detecting a QRS peak based on the plurality of second filtered signals and the detected at least one QRS complex.

Embodiment 14. The method of embodiment 13, further comprising:

determining a threshold function based on the QRS peak; and detecting at least one subsequent QRS complex based on the threshold function.

Embodiment 15. The method as in any one of embodiments 13-14, further comprising determining a QRS onset time value and a QRS offset time value corresponding to the at least one QRS complex.

Embodiment 16. The method as in any one of embodiments 13-15, wherein determining a QRS onset time value and a QRS offset time value comprises:

generating a dispersion signal from the plurality second filtered signals, wherein the dispersion signal is representative of the dispersion of the plurality second filtered signals over time, determining a first derivative signal based on the dispersion signal;

determining a first window of the first derivative signal within a first time period before a peak positive value of the first derivative signal;

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

Embodiment 17. A system for use in cardiac evaluation comprising:

an electrode apparatus comprising a plurality of external electrodes to be disposed proximate a patient's skin; and a computing apparatus comprising processing circuitry, the computing apparatus operably coupled to the electrode apparatus and configured to:

monitor electrical activity from tissue of a patient using a plurality of external electrodes to generate a plurality of electrical signals over time;

filter the plurality of electrical signals using at least one filter to generate plurality of filtered signals;

detect a QRS peak based on the plurality of filtered signals;

determine a threshold function based on the QRS peak, the threshold function configured to provide sensitivity for detecting at least one subsequent QRS complex; and detect the at least one subsequent QRS complex based on the threshold function.

Embodiment 18. The method of embodiment 17, wherein the threshold function is configured to decrease from the at least one QRS complex until the at least one subsequent QRS complex is detected or a base threshold is reached.

Embodiment 19. The system of embodiment 18, wherein the base threshold is a base percentage of the QRS peak.

Embodiment 20. The system as in any one of embodiments 17-19, wherein at least a portion of the threshold function has a linear decrease.

Embodiment 21. The system as in any one of embodiments 17-20, wherein the threshold function is configured to linearly decrease from a first threshold to a second threshold, wherein the first threshold is a first percentage of the QRS peak and the second threshold is a second percentage of the QRS peak.

Embodiment 22. The system of embodiment 21, wherein the first percentage is about 60% and the second percentage is about 30%.

Embodiment 23. The system of embodiment 22, wherein the threshold function is configured to stay constant between a time that the second threshold is reached and until a predetermined amount of time after the detected QRS complex.

Embodiment 24. The system of embodiment 23, wherein the threshold function is configured to drop at the predetermined amount of time to a third threshold that is a third percentage of the QRS peak.

Embodiment 25. The system of embodiment 24, wherein the third percentage is about 15%.

Embodiment 26. The system of embodiment 24, wherein the threshold function is configured to drop linearly from the third threshold to a base threshold.

Embodiment 27. The system of embodiment 26, wherein the base percentage is about 3%.

Embodiment 28. A method for use in cardiac evaluation comprising:

monitoring electrical activity from tissue of a patient using a plurality of external electrodes to generate a plurality of electrical signals over time;

filtering the plurality of electrical signals using at least one filter to generate a plurality of filtered signals;

detecting a QRS peak based on the plurality of filtered signals.

determining a threshold function based on the QRS peak, the threshold function configured to provide sensitivity for detecting at least one subsequent QRS complex; and detecting the at least one subsequent QRS complex based on the threshold function.

Embodiment 29. The method of embodiment 28, wherein the threshold function is configured to decrease from the at least one QRS complex until the at least one subsequent QRS complex is detected or a base threshold is reached.

Embodiment 30. The system of embodiment 29, wherein the base threshold is a base percentage of the QRS peak.

Embodiment 31. A system for use in cardiac evaluation comprising:

an electrode apparatus comprising a plurality of external electrodes to be disposed proximate a patient's skin; and a computing apparatus comprising processing circuitry, the computing apparatus operably coupled to the electrode apparatus and configured to:

monitor electrical activity from tissue of a patient using a plurality of external electrodes to generate a plurality of electrical signals over time;

filter the plurality of electrical signals using a first filter and a second filter to generate a plurality of first filtered signals and plurality of second filtered signals, the first filter and the second filter having different frequency ranges;

detect a QRS peak based on the plurality of first and second filtered signals.

generate a dispersion signal from the plurality second filtered signals, wherein the dispersion signal is representative of the dispersion of the plurality second filtered signals over time, determine a first derivative signal based on the dispersion signal;

determine a QRS onset time value and a QRS offset time value corresponding to the at least one QRS complex based on the first derivative signal.

Embodiment 32. The system of embodiment 31, wherein determining the QRS onset time value and the QRS offset time value comprises:

determining a first window of the first derivative signal within a first time period before a peak positive value of the first derivative signal;

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

Embodiment 33. The system as in any one of embodiments 31-32, wherein the computing apparatus is further configured to determine an activation time for the at least one QRS complex within each of the plurality of cardiac signals within a QRS duration between the QRS onset time value and the QRS offset time value.

Embodiment 34. The system of embodiment 33, wherein the computing apparatus is further configured to determine at least one metric of electrical heterogeneity based on the activation time for each of the at least one QRS complex within each of the plurality of cardiac signals.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:

an electrode apparatus comprising a plurality of external electrodes to be disposed proximate a patient's skin; and a computing apparatus comprising processing circuitry, the computing apparatus operably coupled to the electrode apparatus and configured to:

monitor electrical activity from tissue of a patient using the plurality of external electrodes to generate a plurality of electrical signals over time;

filter the plurality of electrical signals using a first filter having a first frequency range to generate a plurality of first filtered signals;

filter the plurality of electrical signals using a second filter having a second frequency range different than the first frequency range to generate a plurality of second filtered signals;

detect at least one QRS complex based on the plurality of first filtered signals;

detect a QRS peak of the at least one QRS complex based on the plurality of second filtered signals and the detected at least one QRS complex;

generate a dispersion signal from the plurality second filtered signals, wherein the dispersion signal is representative of the dispersion of the plurality second filtered signals over time;

determine a first derivative signal based on the dispersion signal; and determine a QRS onset time value and a QRS offset time value corresponding to the at least one QRS complex based on the first derivative signal.

2. The system of claim 1, wherein the first filter is a bandpass filter configured to filter out frequencies outside of a range of about 10 Hz to about 32 Hz.

3. The system of claim 1, wherein the second filter is a bandpass filter configured to filter out frequencies outside of a range of about 0.5 Hz to about 20 Hz.

4. The system of claim 1, wherein detecting the at least one QRS complex comprises:

generating a first dispersion signal based on the plurality of first filtered signals, wherein the first dispersion signal is representative of the dispersion of the plurality first filtered signals over time; and detecting the at least one QRS complex based on the first dispersion signal.

5. The system of claim 1, wherein detecting the QRS peak comprises:

determining a standard deviation of the plurality of second filtered signals;

initializing a blanking window of a predetermined length based standard deviation; and detecting the peak amplitude of the plurality of second filtered signals within the blanking window.

6. The system of claim 1, wherein the computing apparatus is further configured to:

determine a threshold function based on the QRS peak, the threshold function configured to provide sensitivity for detecting at least one subsequent QRS complex; and detect the at least one subsequent QRS complex based on the threshold function.

7. The system of claim 1, wherein determining the QRS onset time value and the QRS offset time value comprises:

determining a first window of the first derivative signal within a first time period before a peak positive value of the first derivative signal;

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

8. The system of claim 1, wherein the computing apparatus is further configured to determine a plurality of activation times for the at least one QRS complex based on the plurality of cardiac signals within a QRS duration between the QRS onset time value and the QRS offset time value.

9. The system of claim 8, wherein the computing apparatus is further configured to determine at least one metric of electrical heterogeneity based on the plurality of activation times.

10. The system of claim 1, wherein the electrical activity is representative of depolarization of cardiac tissue that propagates through the torso of the patient.

11. The system of claim 1, wherein the plurality of external electrodes comprises a plurality of surface electrodes to be located proximate skin of the patient's torso.

12. A method for use in cardiac evaluation comprising:

monitoring electrical activity from tissue of a patient using a plurality of external electrodes to generate a plurality of electrical signals over time;

filtering the plurality of electrical signals using a first filter having a first frequency range to generate a plurality of first filtered signals;

filtering the plurality of electrical signals using a second filter having a second frequency range different than the first frequency range to generate a plurality of second filtered signals;

detecting at least one QRS complex based on the plurality of first filtered signals;

detecting a QRS peak based on the plurality of second filtered signals and the detected at least one QRS complex;

generating a dispersion signal from the plurality second filtered signals, wherein the dispersion signal is representative of the dispersion of the plurality second filtered signals over time;

determining a first derivative signal based on the dispersion signal; and determining a QRS onset time value and a QRS offset time value corresponding to the at least one QRS complex based on the first derivative signal.

13. The method of claim 12, further comprising:

determining a threshold function based on the QRS peak; and detecting at least one subsequent QRS complex based on the threshold function.

14. The method of claim 12, wherein determining a QRS onset time value and a QRS offset time value comprises:

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

15. A system for use in cardiac evaluation comprising:

an electrode apparatus comprising a plurality of external electrodes to be disposed proximate a patient's skin; and a computing apparatus comprising processing circuitry, the computing apparatus operably coupled to the electrode apparatus and configured to:

monitor electrical activity from tissue of a patient using the plurality of external electrodes to generate a plurality of electrical signals over time;

filter the plurality of electrical signals using a first filter and a second filter to generate a plurality of first filtered signals and plurality of second filtered signals, the first filter and the second filter having different frequency ranges;

detect a QRS peak based on the plurality of first and second filtered signals, generate a dispersion signal from the plurality second filtered signals, wherein the dispersion signal is representative of the dispersion of the plurality second filtered signals over time;

determine a first derivative signal based on the dispersion signal;

determine a QRS onset time value and a QRS offset time value corresponding to the at least one QRS complex based on the first derivative signal.

16. The system of claim 15, wherein determining the QRS onset time value and the QRS offset time value comprises:

determining a first window of the first derivative signal within a first time period before a peak positive value of the first derivative signal;

determining a second window of the first derivative signal within a second time period after a peak negative value of the first derivative signal;

determining the onset time value by determining a last point within the first window that is less than a first threshold; and determining the offset time value by determining a first point within the second window that is greater than a second threshold.

17. The system of claim 15, wherein the computing apparatus is further configured to determine an activation time for the at least one QRS complex within each of the plurality of cardiac signals within a QRS duration between the QRS onset time value and the QRS offset time value.

18. The system of claim 17, wherein the computing apparatus is further configured to determine at least one metric of electrical heterogeneity based on the activation time for each of the at least one QRS complex within each of the plurality of cardiac signals.

* * * * *